US012576162B2

(12) United States Patent
Choi et al.

(10) Patent No.: US 12,576,162 B2
(45) Date of Patent: Mar. 17, 2026

(54) CELL PENETRATING PEPTIDES AND USES THEREOF

(71) Applicant: IUCF-HYU (INDUSTRY-UNIVERSITY COOPERATION FOUNDATION HANYANG UNIVERSITY), Seoul (KR)

(72) Inventors: Je-Min Choi, Seoul (KR); Ja-Hyun Koo, Cheonan-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 785 days.

(21) Appl. No.: 17/827,055

(22) Filed: May 27, 2022

(65) Prior Publication Data

US 2022/0378946 A1    Dec. 1, 2022

(30) Foreign Application Priority Data

May 28, 2021    (KR) ........................ 10-2021-0069432

(51) Int. Cl.
| | |
|---|---|
| *A61K 48/00* | (2006.01) |
| *C07K 7/06* | (2006.01) |
| *C07K 14/435* | (2006.01) |
| *A61K 38/00* | (2006.01) |

(52) U.S. Cl.
CPC ............ *A61K 48/0075* (2013.01); *C07K 7/06* (2013.01); *C07K 14/43595* (2013.01); *A61K 38/00* (2013.01); *C07K 2319/10* (2013.01); *C07K 2319/60* (2013.01)

(58) Field of Classification Search
CPC ......... A61K 48/0075; C07K 7/06; C07K 7/08
See application file for complete search history.

(56) References Cited

FOREIGN PATENT DOCUMENTS

| | | | | |
|---|---|---|---|---|
| CA | 3132385 A1 * | 9/2020 | ............. | A61K 38/00 |
| KR | 10-2010-0011091 A | 2/2010 | | |
| WO | WO-2008116956 A2 * | 10/2008 | ......... | A61K 38/2066 |
| WO | WO-2020181235 A1 * | 9/2020 | ............. | C07K 16/10 |

OTHER PUBLICATIONS

Monali V. Sawai et al., Impact of single-residue mutations on the structure and function of ovispirin/novispirin antimicrobial peptides, Protein Engineering, Design and Selection, vol. 15, Issue 3, Mar. 2002, pp. 225-232, https://doi.org/10.1093/protein/15.3.225 (Year: 2002).*

O'Brien, C., Flower, D.R. & Feighery, C. Peptide length significantly influences in vitro affinity for MHC class II molecules. Immunome Res 4, 6 (2008). https://doi.org/10.1186/1745-7580-4-6 (Year: 2008).*

Cardozo et al., Cell-permeable peptides induce dose- and length-dependent cytotoxic effects, Biochimica et Biophysica Acta (BBA)—Biomembranes, vol. 1768, Issue 9, 2007, (Year: 2007).*

Xiaoying Chen, Jennica L. Zaro, Wei-Chiang Shen, Fusion protein linkers: Property, design and functionality, Advanced Drug Delivery Reviews, vol. 65, Issue 10, 2013, pp. 1357-1369, ISSN 0169-409X, https://doi.org/10.1016/j.addr.2012.09.039. (Year: 2013).*

Benedetta Bolognesi et al., Single Point Mutations Induce a Switch in the Molecular Mechanism of the Aggregation of the Alzheimer's Disease Associated Aβ42 Peptide, ACS Chemical Biology 2014 9 (2), 378-382 DOI: 10.1021/cb400616y (Year: 2014).*

Bahnsen et al., Biochimica et Biophysica Acta (BBA)—Biomembranes, vol. 1828, Issue 2, 2013, pp. 223-232, (Year: 2013).*

Koo, Ja-Hyun, et al. "LRR domain of NLRX1 protein delivery by dNP2 inhibits T cell functions and alleviates autoimmune encephalomyelitis." Theranostics 10.7 (2020): 3138. (Year: 2020).*

Sawai, Monali V., et al. "Impact of single-residue mutations on the structure and function of ovispirin/novispirin antimicrobial peptides." Protein engineering 15.3 (2002): 225-232. (Year: 2002).*

Bolognesi, Benedetta, et al. "Single point mutations induce a switch in the molecular mechanism of the aggregation of the Alzheimer's disease associated Aβ42 peptide." ACS Chemical Biology 9.2 (2014): 378-382. (Year: 2014).*

Wang, Xiaoling, et al. "Potential aggregation prone regions in biotherapeutics: a survey of commercial monoclonal antibodies." MAbs. vol. 1. No. 3. Taylor & Francis, 2009. (Year: 2009).*

Pirouz M Daftarian et al., "Rejection of Large HPV-16 expressing tumors in aged mice by a single immunization of VacciMax encapsulated CTL/T helper peptides", Journal of Translational Medicine, 2007,pp. 1-9.

Roger P. M. Sutmuller et al., "Adoptive T Cell Immunotherapy of Human Uveal Melanoma Targeting gp100", The Journal of Immunology, 2000, pp. 7308-7315.

Kim S. Kawamura et al., "In Vivo Generation of Cytotoxic T Cells from Epitopes Displayed on Peptide-Based Delivery Vehicles", The Journal of Immunology, 2002, pp. 5709-5715.

Seisuke Ota et al., Cellular Processing of a Multibranched Lysine Core with Tumor Antigen Peptides and Presentation of Peptide Epitopes Recognized by Cytotoxic T Lymphocytes on Antigen-presenting Cells, Cancer Research 62, Mar. 1, 2002, pp. 1471-1476.

Miguel Reyes et al., "An immune-cell signature of bacterial sepsis", Nature Medicine.

(Continued)

*Primary Examiner* — Lianko G Garyu
*Assistant Examiner* — David Paul Bowles
(74) *Attorney, Agent, or Firm* — Sughrue Mion, PLLC

(57) ABSTRACT

A novel cytokine-derived cell penetrating peptide and use thereof are provided. The cell penetrating peptide has the ability to effectively deliver a biologically active substance into phagocytes, particularly macrophages, both in vitro and in vivo. The cell penetrating peptide can deliver a biologically active substance into macrophages with high efficiency compared to TAT peptide and dNP2 peptide that are commercially available as cell penetrating peptides.

14 Claims, 35 Drawing Sheets

Specification includes a Sequence Listing.

(56)              References Cited

OTHER PUBLICATIONS

Ja-Hyun Koo, "Thesis for Doctor of Philosophy: Role of the NLRX1 in Regulation of Macrophage and T Cell Functions for Preventing Acute and Chronic Inflammation", Graduate School of Hanyang University, Aug. 2020, pp. 1-230 (252 pages total).
Ja-Hyun Koo, et al., "Macrophage-preferable delivery of the leucine-rich repeat domain of NLRX1 ameliorates lethal sepsis by regulating NF-κB and inflammasome signaling activation", Biomaterials, vol. 274, No. 120845, 2021, pp. 1-10.

* cited by examiner 5 mg of protein
Intraperitoneal injection

Harvest
organs

Slice frozen blocks
and antibody staining

;

Protein treatment scheme

Protein
or antibody
I.P injection 0 h
LPS
(2 mg/kg)
Priming

5 h
LPS
(5 mg/kg)
Challenge

168 h
Survival

SEQUENCE LISTING

```
<160> NUMBER OF SEQ ID NOS: 77

<210> SEQ ID NO 1
<211> LENGTH: 10
<212> TYPE: PRT
<213> ORGANISM: Artificial Sequence
<220> FEATURE:
<223> OTHER INFORMATION: C10, h

<400> SEQUENCE: 1

Leu Arg Leu Arg Leu Arg Arg Cys His Arg
1               5                   10

<210> SEQ ID NO 2
<211> LENGTH: 30
<212> TYPE: DNA
<213> ORGANISM: Artificial Sequence
<220> FEATURE:
<223> OTHER INFORMATION: C10, h

<400> SEQUENCE: 2
ctcaggctga ggctacggcg ctgtcatcga                                        30

<210> SEQ ID NO 3
<211> LENGTH: 10
<212> TYPE: PRT
<213> ORGANISM: Artificial Sequence
<220> FEATURE:
<223> OTHER INFORMATION: C10, m

<400> SEQUENCE: 3

Leu Arg Met Arg Leu Arg Arg Cys His Arg
1               5                   10

<210> SEQ ID NO 4
<211> LENGTH: 30
```

-continued

```
<212> TYPE: DNA
<213> ORGANISM: Artificial Sequence
<220> FEATURE:
<223> OTHER INFORMATION: C10, m

<400> SEQUENCE: 4
ctcaggatgc ggctgaggcg ctgtcatcga                                    30

<210> SEQ ID NO 5
<211> LENGTH: 10
<212> TYPE: PRT
<213> ORGANISM: Artificial Sequence
<220> FEATURE:
<223> OTHER INFORMATION: C10, C>A

<400> SEQUENCE: 5

Leu Arg Leu Arg Leu Arg Arg Ala His Arg
1               5                   10

<210> SEQ ID NO 6
<211> LENGTH: 30
<212> TYPE: DNA
<213> ORGANISM: Artificial Sequence
<220> FEATURE:
<223> OTHER INFORMATION: C10, C>A

<400> SEQUENCE: 6
ctcaggctga ggctacggcg cgctcatcga                                    30

<210> SEQ ID NO 7
<211> LENGTH: 9
<212> TYPE: PRT
<213> ORGANISM: Artificial Sequence
<220> FEATURE:
<223> OTHER INFORMATION: C10, L del

<400> SEQUENCE: 7

Arg Leu Arg Leu Arg Arg Cys His Arg
1               5

<210> SEQ ID NO 8
<211> LENGTH: 27
<212> TYPE: DNA
<213> ORGANISM: Artificial Sequence
<220> FEATURE:
<223> OTHER INFORMATION: C10, L del

<400> SEQUENCE: 8
aggctgaggc tacggcgctg tcatcga                                       27

<210> SEQ ID NO 9
<211> LENGTH: 9
<212> TYPE: PRT
<213> ORGANISM: Artificial Sequence
<220> FEATURE:
<223> OTHER INFORMATION: C10, R del

<400> SEQUENCE: 9

Leu Arg Leu Arg Leu Arg Arg Cys His
1               5

<210> SEQ ID NO 10
<211> LENGTH: 27
<212> TYPE: DNA
<213> ORGANISM: Artificial Sequence
<220> FEATURE:
<223> OTHER INFORMATION: C10, R del
```

-continued

<400> SEQUENCE: 10
ctcaggctga ggctacggcg ctgtcat                                                         27

<210> SEQ ID NO 11
<211> LENGTH: 10
<212> TYPE: PRT
<213> ORGANISM: Artificial Sequence
<220> FEATURE:
<223> OTHER INFORMATION: C10, L>R

<400> SEQUENCE: 11

Arg Arg Leu Arg Leu Arg Arg Cys His Arg
1               5                   10

<210> SEQ ID NO 12
<211> LENGTH: 27
<212> TYPE: DNA
<213> ORGANISM: Artificial Sequence
<220> FEATURE:
<223> OTHER INFORMATION: C10, L>R

<400> SEQUENCE: 12
aagaggctga ggctacggcg ctgtcat                                                         27

<210> SEQ ID NO 13
<211> LENGTH: 10
<212> TYPE: PRT
<213> ORGANISM: Artificial Sequence
<220> FEATURE:
<223> OTHER INFORMATION: C10, L>K

<400> SEQUENCE: 13

Lys Arg Leu Arg Leu Arg Arg Cys His Arg
1               5                   10

<210> SEQ ID NO 14
<211> LENGTH: 27
<212> TYPE: DNA
<213> ORGANISM: Artificial Sequence
<220> FEATURE:
<223> OTHER INFORMATION: C10, L>K

<400> SEQUENCE: 14
cggaggctga ggctacggcg ctgtcat                                                         27

<210> SEQ ID NO 15
<211> LENGTH: 7
<212> TYPE: PRT
<213> ORGANISM: Artificial Sequence
<220> FEATURE:
<223> OTHER INFORMATION: TP peptide

<400> SEQUENCE: 15

Lys Lys Arg Arg Lys Arg Lys
1               5

<210> SEQ ID NO 16
<211> LENGTH: 21
<212> TYPE: DNA
<213> ORGANISM: Artificial Sequence
<220> FEATURE:
<223> OTHER INFORMATION: a nucleic acid sequence encoding a TP peptide

<400> SEQUENCE: 16
aagaagagga gaaaaaggaa a                                                               21

```
<210> SEQ ID NO 17
<211> LENGTH: 9
<212> TYPE: PRT
<213> ORGANISM: Artificial Sequence
<220> FEATURE:
<223> OTHER INFORMATION: TB peptide

<400> SEQUENCE: 17

Leu Arg Leu Leu Arg Leu Lys Leu Lys
1               5

<210> SEQ ID NO 18
<211> LENGTH: 27
<212> TYPE: DNA
<213> ORGANISM: Artificial Sequence
<220> FEATURE:
<223> OTHER INFORMATION: a nucleic acid sequence encoding a TB peptide

<400> SEQUENCE: 18
ctgcgtctgc tgaggctcaa gttaaaa                                                    27

<210> SEQ ID NO 19
<211> LENGTH: 11
<212> TYPE: PRT
<213> ORGANISM: Artificial Sequence
<220> FEATURE:
<223> OTHER INFORMATION: TAT peptide

<400> SEQUENCE: 19

Tyr Gly Arg Lys Lys Arg Arg Gln Arg Arg Arg
1               5                   10

<210> SEQ ID NO 20
<211> LENGTH: 33
<212> TYPE: DNA
<213> ORGANISM: Artificial Sequence
<220> FEATURE:
<223> OTHER INFORMATION: a necleic acid sequence encoding a TAT peptide

<400> SEQUENCE: 20
tatggacgca agaagcgccg ccagcgccgc cgc                                             33

<210> SEQ ID NO 21
<211> LENGTH: 24
<212> TYPE: PRT
<213> ORGANISM: Artificial Sequence
<220> FEATURE:
<223> OTHER INFORMATION: dNP2 peptide

<400> SEQUENCE: 21

Lys Ile Lys Lys Val Lys Lys Lys Gly Arg Lys Gly Ser Lys Ile Lys
1               5                   10                  15

Lys Val Lys Lys Lys Gly Arg Lys
            20

<210> SEQ ID NO 22
<211> LENGTH: 72
<212> TYPE: DNA
<213> ORGANISM: Artificial Sequence
<220> FEATURE:
<223> OTHER INFORMATION: a necleic acid sequence encoding a dNP2 peptide

<400> SEQUENCE: 22
aaaattaaaa aagtcaagaa gaaaggaaga aaaggatcca aaattaaaaa agtcaagaag     60
```

-continued aaaggaagaa aa                                                              72

```
<210> SEQ ID NO 23
<211> LENGTH: 975
<212> TYPE: PRT
<213> ORGANISM: Artificial Sequence
<220> FEATURE:
<223> OTHER INFORMATION: NLRX1 protein

<400> SEQUENCE: 23

Met Arg Trp Gly Cys His Leu Pro Arg Thr Ser Trp Gly Ser Gly Leu
1               5                   10                  15

Gly Arg Thr Pro Gln Leu Pro Asp Glu His Ile Ser Phe Leu Ile Gln
            20                  25                  30

Trp Ser Trp Pro Phe Lys Gly Val His Pro Leu Arg Pro Pro Arg Ala
        35                  40                  45

Phe Ile Arg Tyr His Gly Asn Ser Ala Asp Ser Ala Pro Pro Pro Gly
    50                  55                  60

Arg His Gly Gln Leu Phe Arg Ser Ile Ser Ala Thr Glu Ala Ile Gln
65                  70                  75                  80

Arg His Arg Arg Asn Leu Thr Glu Trp Phe Ser Arg Leu Pro Arg Glu
                85                  90                  95

Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Ser Thr
            115                 120                 125

Glu Leu Ala Thr Gly His Gln Gln Thr Gln Ala Gly Leu Pro Pro Leu
        130                 135                 140

Ala Leu Ser Gln Leu Phe Asp Pro Asp Ser Cys Gly Arg Arg Val Gln
145                 150                 155                 160

Thr Val Val Leu Tyr Gly Thr Val Gly Thr Gly Lys Ser Thr Leu Val
                165                 170                 175

Arg Lys Met Val Leu Asp Trp Cys Tyr Gly Arg Leu Pro Ala Phe Glu
            180                 185                 190

Leu Leu Ile Pro Phe Ser Cys Glu Asp Leu Ser Ser Leu Gly Ser Thr
            195                 200                 205

Pro Ala Ser Leu Cys Gln Leu Val Thr Gln Arg Tyr Thr Pro Leu Lys
        210                 215                 220

Glu Val Leu Pro Leu Met Thr Ala Ala Gly Ser Arg Leu Leu Phe Val
225                 230                 235                 240

Leu His Gly Leu Glu Arg Leu Asn Leu Asp Phe Arg Leu Ala Gly Thr
                245                 250                 255

Gly Leu Cys Ser Asp Pro Glu Glu Pro Gly Pro Pro Ala Ala Ile Ile
            260                 265                 270

Val Asn Leu Leu Arg Lys Tyr Met Leu Pro Glu Ala Ser Ile Leu Val
        275                 280                 285

Thr Thr Arg Pro Ser Thr Ile Ser Arg Ile Pro Ser Lys Tyr Val Gly
        290                 295                 300

Arg Tyr Gly Glu Ile Cys Gly Phe Ser Asp Thr Asn Leu Gln Lys Leu
305                 310                 315                 320

Tyr Phe Gln Leu Arg Leu Asn Gln Pro Asp Cys Gly Tyr Gly Ala Gly
                325                 330                 335

Gly Ala Ser Val Ser Val Thr Pro Ala Gln Arg Asp Asn Leu Ile Gln
            340                 345                 350

Met Leu Ser Arg Asn Leu Glu Gly His His Gln Ile Ala Ala Ala Cys
```

-continued

```
          355                 360                 365

Phe Leu Pro Ser Tyr Cys Trp Leu Val Cys Ala Thr Leu His Phe Leu
    370                 375                 380

His Ala Pro Thr Pro Ala Gly Gln Thr Leu Thr Ser Ile Tyr Thr Ser
385                 390                 395                 400

Phe Leu Arg Leu Asn Phe Ser Gly Glu Thr Leu Asp Ser Thr His Thr
                405                 410                 415

Ser Asn Leu Ser Leu Met Ser Tyr Ala Ala Arg Thr Met Gly Lys Leu
                420                 425                 430

Ala Tyr Glu Gly Val Ser Ser Arg Lys Thr Tyr Phe Ser Glu Glu Asp
            435                 440                 445

Val Arg Gly Cys Leu Glu Ala Gly Ile Lys Thr Glu Glu Glu Phe Gln
        450                 455                 460

Leu Leu Gln Ile Phe Arg Arg Asp Ala Leu Arg Phe Phe Leu Ala Pro
465                 470                 475                 480

Cys Val Glu Pro Gly His Leu Gly Thr Phe Val Phe Thr Val Pro Ala
                485                 490                 495

Met Gln Glu Tyr Leu Ala Ala Leu Tyr Ile Val Leu Gly Leu Arg Lys
                500                 505                 510

Thr Ala Leu Gln Arg Val Gly Lys Glu Val Val Glu Phe Val Gly Arg
            515                 520                 525

Val Gly Glu Asp Val Ser Leu Val Leu Gly Ile Val Ala Lys Leu Leu
        530                 535                 540

Pro Leu Arg Ile Leu Pro Leu Leu Phe Asn Leu Leu Lys Val Val Pro
545                 550                 555                 560

Arg Val Phe Gly Arg Met Val Ser Lys Ser Arg Glu Ala Val Ala Gln
                565                 570                 575

Ala Met Val Leu Glu Met Phe Arg Glu Glu Asp Tyr Tyr Asn Asp Asp
                580                 585                 590

Val Leu Asp Gln Met Gly Ala Ser Ile Leu Gly Val Glu Gly Pro Arg
            595                 600                 605

Arg His Pro Asp Glu Pro Ser Glu Asp Glu Val Phe Glu Leu Phe Pro
        610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
                645                 650                 655

Ala Ile Lys Lys Lys Leu Gly Lys Leu Gly Arg Gln Val Leu Pro Pro
                660                 665                 670

Ser Glu Leu Leu Asp His Leu Phe Phe His Tyr Glu Phe Gln Asn Gln
            675                 680                 685

Arg Phe Ser Ala Glu Val Leu Gly Ser Leu Arg Gln Leu Asn Leu Ala
            690                 695                 700

Gly Val Arg Met Thr Pro Leu Lys Cys Thr Val Val Ala Ser Val Leu
705                 710                 715                 720

Gly Ser Gly Arg His Pro Leu Asp Glu Val Asn Leu Ala Ser Cys Gln
                725                 730                 735

Leu Asp Pro Ala Gly Leu His Thr Leu Met Pro Val Leu Leu Arg Ala
            740                 745                 750

Arg Lys Leu Gly Leu Gln Leu Asn Asn Leu Gly Pro Glu Ala Cys Arg
            755                 760                 765

Asp Leu Arg Asp Leu Leu Leu His Asp Gln Cys Gln Ile Thr Thr Leu
    770                 775                 780
```

```
Arg Leu Ser Asn Asn Pro Leu Thr Ala Ala Gly Val Gly Leu Leu Met
785                 790                 795                 800

Asp Gly Leu Ala Gly Asn Thr Ser Val Thr His Leu Ser Leu Leu His
                805                 810                 815

Thr Asp Leu Gly Asp Glu Gly Leu Glu Leu Leu Ala Ala Gln Leu Asp
            820                 825                 830

Arg Asn Lys Gln Leu Gln Glu Leu Asn Val Ala Tyr Asn Gly Ala Gly
            835                 840                 845

Asp Thr Val Ala Leu Ala Leu Ala Lys Ala Ala Arg Glu His Pro Ser
        850                 855                 860

Leu Glu Leu Leu His Leu Tyr Phe Asn Glu Leu Ser Ser Glu Gly Arg
865                 870                 875                 880

Gln Val Leu Arg Asp Leu Gly Gly Ser Gly Glu Gly Gly Ala Arg Val
                885                 890                 895

Val Ala Ser Leu Thr Glu Gly Thr Ala Val Ser Glu Tyr Trp Ser Val
            900                 905                 910

Ile Leu Ser Glu Val Gln Arg Asn Val His Ser Trp Asp Pro Leu Arg
            915                 920                 925

Val Gln Arg His Leu Lys Leu Leu Leu Arg Asp Leu Glu Asp Ser Arg
        930                 935                 940

Gly Ala Thr Leu Asn Pro Trp Arg Lys Ala Gln Leu Leu Arg Val Glu
945                 950                 955                 960

Gly Glu Val Lys Thr Leu Leu Glu Gln Leu Gly Gly Ser Gly His
                965                 970                 975

<210> SEQ ID NO 24
<211> LENGTH: 2928
<212> TYPE: DNA
<213> ORGANISM: Artificial Sequence
<220> FEATURE:
<223> OTHER INFORMATION: nucleic acid sequence encoding NLRX1 protein

<400> SEQUENCE: 24
atgaggtggg gctgccattt gcccaggacc tcttggggct ctggcctggg aagaacaccc       60
cagctaccag atgagcatat ctccttcttg atccagtgga gctggcccctt taaaggggtg      120 catcccctga ggcccccctag ggcctttatc cgttaccatg gaaactcggc agacagtgct      180
cccccaccag ggaggcatgg gcagctgttc aggagcatct ctgccacaga gctatccaa       240 aggcatcgcc ggaacctcac cgagtggttt agccgactgc ccagagagga gcgccagttt      300
ggaccaacct ttgctctaga cacagttcat gttgaccccg tgatccgaga gagcacccca      360
gatgagctgc ttcgcccgtc cacggagctg gccacggggc atcagcaaac ccaggcaggg      420 ctcccccac tggccctgtc tcagcttttt gaccccggatt cttgtgggcg ccgcgtgcag       480
accgtggtgt tgtatgggac cgtgggtact ggcaagagca cgttggtacg aagatggtc       540 ttagactggt gttacgggag actgcctgcc tttgagcttc tcatcccctt ctcctgtgag      600
gacttgtcat ccctgggctc cacccccagct tccctgtgcc aacttgtgac ccagcgttac      660 acaccccctga aagaggtgtt gcccctgatg actgctgcgg gatcccgcct gctctttgtg       720
ctccatggct tggagcgcct caaccttgac ttccggctgg caggcacagg ctttgcagt       780 gacccggagg aacccgggcc accagctgcc atcatagtca acctgctgcg caaatacatg       840
cttcccgagg ccagcattct ggtaaccacc cggccttcca ccattagccg aatccctagc      900
aagtatgtgg gccgctatgg tgagatctgt ggcttctctg ataccaacct gcagaagctc      960
```

-continued

```
tacttccagc tccgccttaa ccagcctgac tgtgggtacg gtgctggggg tgccagtgtc      1020
tcagtcacac cagctcagcg cgacaacctg attcaaatgc tctcccggaa cctggagggg      1080
caccaccaga ttgccgcagc ctgctttctg ccttcctatt gctggcttgt ctgtgctact      1140
ttgcacttcc tgcatgctcc cacacctgct ggtcagaccc tcacaagcat ctataccagc      1200
tttctacgcc tgaacttcag tggggaaaca ctggacagca cccacacgtc caatctatcc      1260
ctgatgtcct atgcagcccg gactatgggc aagctggcct acgagggcgt gtcatcccga      1320
aagacctact tctctgaaga ggatgtccgt ggctgcctgg aagctggcat caagacagag      1380
gaagagtttc aactgcttca gatcttccgc agggacgccc tgaggttttt cctggccccg      1440
tgtgtggaac cagggcacct gggtaccttc gtgttcaccg tgcccgccat gcaggagtat      1500
ctggctgccc tctacatcgt gcttggtttg cgcaagacag ccctgcagcg ggtgggcaaa      1560
gaagtggttg aatttgtggg ccgtgttggg gaagatgtca gcctggtatt gggcattgtg      1620
gccaagctgt tgcccctgcg gattctgcct ctgctcttca acttgctcaa ggtagttccg      1680
cgagtgtttg ggcgcatggt gagtaagagc cgggaggcag tggcccaggc catggtgctg      1740
gagatgttcc gggaggaaga ctactacaat gacgatgttc tggatcagat gggtgccagc      1800
atcctgggtg tggagggccc ccggcgccac ccagatgaac cctctgagga tgaagtcttt      1860
gagctcttcc ccatgttcat gggcggactt ctctctgccc acaaccgggc ggtgctggct      1920
cagcttggct gtcccatcaa gaacctggat gccctggaga atgcccaggc catcaagaag      1980
aagctgggga agctgggtcg gcaggtgctg ccccctcgg agcttcttga ccatctcttc      2040
ttccactatg agtccagaa ccagcgcttc tcagctgagg tgctgggctc cctacgccag      2100
ctcaatttag caggggtgcg catgacaccc ctcaagtgca cagtggtagc ctctgtactg      2160
ggaagtggaa ggcacccct ggatgaggtg aacttggcct cctgccagct ggatcccgct      2220
gggctacaca ctctcatgcc tgtcctcctg cgtgcccgga aactggggtt gcaactcaac      2280
aatctgggcc ccgaggcctg cagagacctc cgagacctgc tcttacacga tcaatgccag      2340
atcaccactc ttaggctctc caacaaccca ctgacagcag ctggtgtggg cttactgatg      2400
gacgggctgg caggaaacac ttcggtgaca cacctgtctc tgctgcacac tgaccttgga      2460
gacgagggac tggaactgct ggctgcccag ctggaccgaa acaaacaact gcaggagctg      2520
aacgtggcct acaacggtgc tggtgacaca gtggctctgg ccttggctaa ggctgctcgg      2580
gagcacccct ccctggagct gctgcacctc tacttcaatg agctgagttc agagggccgc      2640
caggtcctgc gggatttggg gggctctggt gaaggtggtg cccgggtcgt agcctcgctg      2700
acagaaggga cggcggtgtc tgagtactgg tcagtgatcc ttagtgaagt ccagcgcaac      2760
gtccacagct gggacccgct ccgggtccag aggcatctca agctgctgct ccgtgatctg      2820
gaggacagcc ggggcgccac ccttaatccc tggcgcaagg ctcagcttct gcgagtggag      2880
ggcgaggtca agactcttct ggagcagctg ggaggttctg acactga                     2928
```

<210> SEQ ID NO 25
<211> LENGTH: 301
<212> TYPE: PRT
<213> ORGANISM: Artificial Sequence
<220> FEATURE:
<223> OTHER INFORMATION: LRR domain

<400> SEQUENCE: 25

```
Leu Leu Asp His Leu Phe Phe His Tyr Glu Phe Gln Asn Gln Arg Phe
1               5                   10                  15
```

-continued

```
Ser Ala Glu Val Leu Gly Ser Leu Arg Gln Leu Asn Leu Ala Gly Val
            20                  25                  30

Arg Met Thr Pro Leu Lys Cys Thr Val Val Ala Ser Val Leu Gly Ser
        35                  40                  45

Gly Arg His Pro Leu Asp Glu Val Asn Leu Ala Ser Cys Gln Leu Asp
    50                  55                  60

Pro Ala Gly Leu His Thr Leu Met Pro Val Leu Leu Arg Ala Arg Lys
65                  70                  75                  80

Leu Gly Leu Gln Leu Asn Asn Leu Gly Pro Glu Ala Cys Arg Asp Leu
                85                  90                  95

Arg Asp Leu Leu Leu His Asp Gln Cys Gln Ile Thr Thr Leu Arg Leu
            100                 105                 110

Ser Asn Asn Pro Leu Thr Ala Ala Gly Val Gly Leu Leu Met Asp Gly
            115                 120                 125

Leu Ala Gly Asn Thr Ser Val Thr His Leu Ser Leu Leu His Thr Asp
    130                 135                 140

Leu Gly Asp Glu Gly Leu Glu Leu Leu Ala Ala Gln Leu Asp Arg Asn
145                 150                 155                 160

Lys Gln Leu Gln Glu Leu Asn Val Ala Tyr Asn Gly Ala Gly Asp Thr
                165                 170                 175

Val Ala Leu Ala Leu Ala Lys Ala Ala Arg Glu His Pro Ser Leu Glu
            180                 185                 190

Leu Leu His Leu Tyr Phe Asn Glu Leu Ser Ser Glu Gly Arg Gln Val
            195                 200                 205

Leu Arg Asp Leu Gly Gly Ser Gly Glu Gly Gly Ala Arg Val Val Ala
    210                 215                 220

Ser Leu Thr Glu Gly Thr Ala Val Ser Glu Tyr Trp Ser Val Ile Leu
225                 230                 235                 240

Ser Glu Val Gln Arg Asn Val His Ser Trp Asp Pro Leu Arg Val Gln
                245                 250                 255

Arg His Leu Lys Leu Leu Leu Arg Asp Leu Glu Asp Ser Arg Gly Ala
            260                 265                 270

Thr Leu Asn Pro Trp Arg Lys Ala Gln Leu Leu Arg Val Glu Gly Glu
            275                 280                 285

Val Lys Thr Leu Leu Glu Gln Leu Gly Gly Ser Gly His
    290                 295                 300
```

```
<210> SEQ ID NO 26
<211> LENGTH: 903
<212> TYPE: DNA
<213> ORGANISM: Artificial Sequence
<220> FEATURE:
<223> OTHER INFORMATION: nucleic acid sequence encoding LRR domain

<400> SEQUENCE: 26
cttcttgacc atctcttctt ccactatgag ttccagaacc agcgcttctc agctgaggtg      60
ctgggctccc tacgccagct caatttagca ggggtgcgca tgacacccct caagtgcaca     120
gtggtagcct ctgtactggg aagtggaagg caccccctgg atgaggtgaa cttggcctcc     180
tgccagctgg atcccgctgg ctacacact  ctcatgcctg tcctcctgcg tgcccggaaa     240
ctggggttgc aactcaacaa tctgggcccc gaggcctgca gagacctccg agacctgctc     300
ttacacgatc aatgccagat caccactctt aggctctcca acaacccact gacagcagct     360
ggtgtgggct actgatggga cgggctggca ggaaacactt cggtgacaca cctgtctctg     420
ctgcacactg accttggaga cgagggactg gaactgctgg ctgcccagct ggaccgaaac     480
```

-continued

```
aaacaactgc aggagctgaa cgtggcctac aacggtgctg gtgacacagt ggctctggcc      540
ttggctaagg ctgctcggga gcacccttcc ctggagctgc tgcacctcta cttcaatgag      600
ctgagttcag agggccgcca ggtcctgcgg gatttggggg gctctggtga aggtggtgcc      660
cgggtcgtag cctcgctgac agaagggacg gcggtgtctg agtactggtc agtgatcctt      720
agtgaagtcc agcgcaacgt ccacagctgg gacccgctcc gggtccagag gcatctcaag      780
ctgctgctcc gtgatctgga ggacagccgg ggcgccaccc ttaatccctg cgcgcaaggct      840 cagcttctgc gagtggaggg cgaggtcaag actcttctgg agcagctggg aggttctgga      900
cac                                                                   903
```

<210> SEQ ID NO 27
<211> LENGTH: 482
<212> TYPE: PRT
<213> ORGANISM: Artificial Sequence
<220> FEATURE:
<223> OTHER INFORMATION: NBD domain

<400> SEQUENCE: 27

```
Ala Thr Glu Ala Ile Gln Arg His Arg Arg Asn Leu Thr Glu Trp Phe
1               5                   10                  15

Ser Arg Leu Pro Arg Glu Glu Arg Gln Phe Gly Pro Thr Phe Ala Leu
            20                  25                  30

Asp Thr Val His Val Asp Pro Val Ile Arg Glu Ser Thr Pro Asp Glu
        35                  40                  45

Leu Leu Arg Pro Ser Thr Glu Leu Ala Thr Gly His Gln Gln Thr Gln
    50                  55                  60

Ala Gly Leu Pro Pro Leu Ala Leu Ser Gln Leu Phe Asp Pro Asp Ser
65                  70                  75                  80

Cys Gly Arg Arg Val Gln Thr Val Val Leu Tyr Gly Thr Val Gly Thr
                85                  90                  95

Gly Lys Ser Thr Leu Val Arg Lys Met Val Leu Asp Trp Cys Tyr Gly
            100                 105                 110

Arg Leu Pro Ala Phe Glu Leu Leu Ile Pro Phe Ser Cys Glu Asp Leu
        115                 120                 125

Ser Ser Leu Gly Ser Thr Pro Ala Ser Leu Cys Gln Leu Val Thr Gln
    130                 135                 140

Arg Tyr Thr Pro Leu Lys Glu Val Leu Pro Leu Met Thr Ala Ala Gly
145                 150                 155                 160

Ser Arg Leu Leu Phe Val Leu His Gly Leu Glu Arg Leu Asn Leu Asp
                165                 170                 175

Phe Arg Leu Ala Gly Thr Gly Leu Cys Ser Asp Pro Glu Glu Pro Gly
            180                 185                 190

Pro Pro Ala Ala Ile Ile Val Asn Leu Leu Arg Lys Tyr Met Leu Pro
        195                 200                 205

Glu Ala Ser Ile Leu Val Thr Thr Arg Pro Ser Thr Ile Ser Arg Ile
    210                 215                 220

Pro Ser Lys Tyr Val Gly Arg Tyr Gly Glu Ile Cys Gly Phe Ser Asp
225                 230                 235                 240

Thr Asn Leu Gln Lys Leu Tyr Phe Gln Leu Arg Leu Asn Gln Pro Asp
                245                 250                 255

Cys Gly Tyr Gly Ala Gly Gly Ala Ser Val Ser Val Thr Pro Ala Gln
            260                 265                 270

Arg Asp Asn Leu Ile Gln Met Leu Ser Arg Asn Leu Glu Gly His His
```

-continued

```
                275                 280                 285
Gln Ile Ala Ala Ala Cys Phe Leu Pro Ser Tyr Cys Trp Leu Val Cys
    290                 295                 300
Ala Thr Leu His Phe Leu His Ala Pro Thr Pro Ala Gly Gln Thr Leu
305                 310                 315                 320
Thr Ser Ile Tyr Thr Ser Phe Leu Arg Leu Asn Phe Ser Gly Glu Thr
                325                 330                 335
Leu Asp Ser Thr His Thr Ser Asn Leu Ser Leu Met Ser Tyr Ala Ala
                340                 345                 350
Arg Thr Met Gly Lys Leu Ala Tyr Glu Gly Val Pro Ser Arg Lys Thr
                355                 360                 365
Tyr Phe Ser Glu Glu Asp Val Arg Gly Cys Leu Glu Ala Gly Ile Lys
    370                 375                 380
Thr Glu Glu Glu Phe Gln Leu Leu Gln Ile Phe Arg Arg Asp Ala Leu
385                 390                 395                 400
Arg Phe Phe Leu Ala Pro Cys Val Glu Pro Gly His Leu Gly Thr Phe
                405                 410                 415
Val Phe Thr Val Pro Ala Met Gln Glu Tyr Leu Ala Ala Leu Tyr Ser
                420                 425                 430
Val Leu Gly Leu Arg Lys Thr Ala Leu Gln Arg Val Gly Lys Glu Val
                435                 440                 445
Val Glu Phe Val Gly Arg Val Gly Glu Asp Val Ser Leu Val Leu Gly
    450                 455                 460
Ile Val Ala Lys Leu Leu Pro Leu Arg Ile Leu Pro Leu Leu Phe Asn
465                 470                 475                 480
Leu Leu
```

```
<210> SEQ ID NO 28
<211> LENGTH: 1446
<212> TYPE: DNA
<213> ORGANISM: Artificial Sequence
<220> FEATURE:
<223> OTHER INFORMATION: nucleic acid sequence encoding NBD domain

<400> SEQUENCE: 28
gccacagaag ctatccaaag gcatcgccgg aacctcaccg agtggtttag ccgactgccc        60
agagaggagc gccagtttgg accaaccttt gctctagaca cagttcatgt tgaccccgtg       120
atccgagaga gcaccccaga tgagctgctt cgcccgtcca cggagctggc cacggggcat       180
cagcaaaccc aggcagggct ccccccactg gccctgtctc agcttttttga cccggattct       240 tgtgggcgcc gcgtgcagac cgtggtgttg tatgggaccg tgggtactgg caagagcacg       300
ttggtacgga agatggtctt agactggtgt tacgggagac tgcctgcctt tgagcttctc       360
atccccttct cctgtgagga cttgtcatcc ctgggctcca ccccagcttc cctgtgccaa       420
cttgtgaccc agcgttacac accctgaaa gaggtgttgc ccctgatgac tgctgcggga       480
tcccgcctgc tctttgtgct ccatggcttg gagcgcctca accttgactt ccggctggca       540
ggcacagggc tttgcagtga cccggaggaa cccgggccac cagctgccat catagtcaac       600
ctgctgcgca aatacatgct ccccgaggcc agcattctgg taaccacccg gccttccacc       660
attagccgaa tccctagcaa gtatgtgggc cgctatggtg agatctgtgg cttctctgat       720
accaacctgc agaagctcta cttccagctc cgccttaacc agcctgactg tgggtacggt       780 gctggggtg ccagtgtctc agtcacacca gctcagcgcg acaacctgat tcaaatgctc       840
tcccggaacc tggaggggca ccaccagatt gccgcagcct gctttctgcc ttcctattgc       900
```

```
tggcttgtct gtgctacttt gcacttcctg catgctccca cacctgctgg tcagaccctc      960
acaagcatct ataccagctt tctacgcctg aacttcagtg gggaaacact ggacagcacc     1020
cacacgtcca atctatccct gatgtcctat gcagcccgga ctatgggcaa gctggcctac     1080
gagggcgtgc catcccgaaa gacctacttc tctgaagagg atgtccgtgg ctgcctggaa     1140
gctggcatca agacagagga agagtttcaa ctgcttcaga tcttccgcag ggacgccctg     1200 aggttttttcc tggccccgtg tgtggaacca gggcacctgg taccttcgt gttcaccgtg      1260 cccgccatgc aggagtatct ggctgccctc tacagcgtgc ttggtttgcg caagacagcc     1320
ctgcagcggg tgggcaaaga agtggttgaa tttgtgggcc gtgttgggga agatgtcagc     1380
ctggtattgg gcattgtggc caagctgttg cccctgcgga ttctgcctct gctcttcaac     1440
ttgctc                                                                 1446
```

```
<210> SEQ ID NO 29
<211> LENGTH: 60
<212> TYPE: DNA
<213> ORGANISM: Artificial Sequence
<220> FEATURE:
<223> OTHER INFORMATION: Forward primer of C10-EGFP

<400> SEQUENCE: 29
ctagctagcc tcaggctgag gctacggcgc tgtcatcgag gatccgtgag caagggcgag      60
```

```
<210> SEQ ID NO 30
<211> LENGTH: 69
<212> TYPE: DNA
<213> ORGANISM: Artificial Sequence
<220> FEATURE:
<223> OTHER INFORMATION: reverse primer of C10-EGFP

<400> SEQUENCE: 30
cccaagcttt tattacttgt acagctcgtc catgccgaga gtgatcccgg cggcggtcac      60
gaactccag                                                              69
```

```
<210> SEQ ID NO 31
<211> LENGTH: 795
<212> TYPE: DNA
<213> ORGANISM: Artificial Sequence
<220> FEATURE:
<223> OTHER INFORMATION: nucleic acid sequence encoding Fusion protein
     C10-EGFP

<400> SEQUENCE: 31
atgcggggtt ctcatcatca tcatcatcat ggtatggcta gcctcaggct gaggctacgg      60
cgctgtcatc gaggatccgt gagcaagggc gaggagctgt tcaccggggt ggtgcccatc     120
ctggtcgagc tggacggcga cgtaaacggc cacaagttca gcgtgtccgg cgagggcgag     180
ggcgatgcca cctacggcaa gctgaccctg aagttcatct gcaccaccgg caagctgccc     240
gtgccctggc ccaccctcgt gaccaccctg acctacggcg tgcagtgctt cagccgctac     300
cccgaccaca tgaagcagca cgacttcttc aagtccgcca tgcccgaagg ctacgtccag     360
gagcgcacca tcttcttcaa ggacgacggc aactacaaga cccgcgccga ggtgaagttc     420
gagggcgaca ccctggtgaa ccgcatcgag ctgaagggca tcgacttcaa ggaggacggc     480
aacatcctgg ggcacaagct ggagtacaac tacaacagcc acaacgtcta tatcatggcc     540
gacaagcaga agaacggcat caaggtgaac ttcaagatcc gccacaacat cgaggacggc     600
agcgtgcagc tcgccgacca ctaccagcag aacacccacca tcggcgacgg ccccgtgctg      660
```

-continued

```
ctgcccgaca accactacct gagcacccag tccgccctga gcaaagaccc caacgagaag    720
cgcgatcaca tggtcctgct ggagttcgtg accgccgccg ggatcactct cggcatggac    780
gagctgtaca agtaa                                                      795

<210> SEQ ID NO 32
<211> LENGTH: 60
<212> TYPE: DNA
<213> ORGANISM: Artificial Sequence
<220> FEATURE:
<223> OTHER INFORMATION: forward primer of C10-LRR

<400> SEQUENCE: 32
ctagctagcc tcaggctgag gctacggcgc tgtcatcgag tcgaccttct tgaccatctc     60

<210> SEQ ID NO 33
<211> LENGTH: 22
<212> TYPE: DNA
<213> ORGANISM: Artificial Sequence
<220> FEATURE:
<223> OTHER INFORMATION: reverse primer of C10-LRR

<400> SEQUENCE: 33
aggttctgga cacgaattcc gg                                              22

<210> SEQ ID NO 34
<211> LENGTH: 1065
<212> TYPE: DNA
<213> ORGANISM: Artificial Sequence
<220> FEATURE:
<223> OTHER INFORMATION: nucleic acid sequence encoding C10-LRR

<400> SEQUENCE: 34
atgggcagca gccatcatca tcatcatcac agcagcggcc tggtgccgcg cggcagccat     60
atggctagcc tcaggctgag gctacggcgc tgtcatcgag tcgaccttct tgaccatctc    120
ttcttccact atgagttcca gaaccagcgc ttctcagctg aggtgctggg ctccctacgc    180
cagctcaatt tagcaggggt gcgcatgaca cccctcaagt gcacagtggt agcctctgta    240
ctgggaagtg gaaggcaccc cctggatgag gtgaacttgg cctcctgcca gctggatccc    300
gctgggctac acactctcat gcctgtcctc ctgcgtgccc ggaaactggg gttgcaactc    360
aacaatctgg gccccgaggc ctgcagagac tccgagacc tgctcttaca cgatcaatgc    420
cagatcacca ctcttaggct ctccaacaac ccactgacag cagctggtgt gggcttactg    480
atggacgggc tggcaggaaa cacttcggtg acacacctgt ctctgctgca cactgacctt    540
ggagacgagg gactggaact gctggctgcc cagctggacc gaaacaaaca actgcaggag    600
ctgaacgtgg cctacaacgg tgctggtgac acagtggctc tggccttggc taaggctgct    660
cgggagcacc cttccctgga gctgctgcac ctctacttca tgagctgag ttcagagggc    720 cgccaggtcc tgcgggattt ggggggctct ggtgaaggtg gtgcccgggt cgtagcctcg    780
ctgacagaag ggacggcggt gtctgagtac tggtcagtga tccttagtga agtccagcgc    840
aacgtccaca gctgggaccc gctccgggtc cagaggcatc tcaagctgct gctccgtgat    900
ctggaggaca gccggggcgc caccccttaat ccctggcgca aggctcagct tctgcgagtg    960
gagggcgagg tcaagactct tctggagcag ctgggaggtt ctggacacga attcgattac   1020
aaggatgacg atgacaagct cgagcaccac caccaccacc actga                  1065

<210> SEQ ID NO 35
```

```
<211> LENGTH: 27
<212> TYPE: DNA
<213> ORGANISM: Artificial Sequence
<220> FEATURE:
<223> OTHER INFORMATION: forward primer of C10-NBD

<400> SEQUENCE: 35
ctagtcgacg ccacagaagc tatccaa                                         27

<210> SEQ ID NO 36
<211> LENGTH: 27
<212> TYPE: DNA
<213> ORGANISM: Artificial Sequence
<220> FEATURE:
<223> OTHER INFORMATION: reverse primer of C10-NBD

<400> SEQUENCE: 36
ccggaattcg agcaagttga agagcag                                         27

<210> SEQ ID NO 37
<211> LENGTH: 1608
<212> TYPE: DNA
<213> ORGANISM: Artificial Sequence
<220> FEATURE:
<223> OTHER INFORMATION: nucleic acid sequence encoding C10-NBD

<400> SEQUENCE: 37
atgggcagca gccatcatca tcatcatcac agcagcggcc tggtgccgcg cggcagccat      60
atggctagcc tcaggctgag gctacggcgc tgtcatcgag tcgacgccac agaagctatc     120
caaaggcatc gccggaacct caccgagtgg tttagccgac tgcccagaga ggagcgccag     180
tttggaccaa cctttgctct agacacagtt catgttgacc ccgtgatccg agagagcacc     240
ccagatgagc tgcttcgccc gtccacggag ctggccacgg ggcatcagca aacccaggca     300
gggctccccc cactggccct gtctcagctt tttgacccgg attcttgtgg gcgccgcgtg     360
cagaccgtgg tgttgtatgg gaccgtgggg actggcaaga gcacgttggt acggaagatg     420
gtcttagact ggtgttacgg gagactgcct gcctttgagc ttctcatccc cttctcctgt     480
gaggacttgt catccctggg ctccacccca gcttccctgt gccaacttgt gacccagcgt     540
tacacacccc tgaaagaggt gttgcccctg atgactgctg cgggatcccg cctgctcttt     600
gtgctccatg gcttggagcg cctcaacctt gacttccggc tggcaggcac agggctttgc     660
agtgacccgg aggaacccgg gccaccagct gccatcatag tcaacctgct gcgcaaatac     720
atgcttcccg aggccagcat tctggtaacc acccggcctt ccaccattag ccgaatccct     780
agcaagtatg tgggccgcta tggtgagatc tgtggcttct ctgataccaa cctgcagaag     840
ctctacttcc agctccgcct taaccagcct gactgtgggt acggtgctgg gggtgccagt     900
gtctcagtca caccagctca gcgcgacaac ctgattcaaa tgctctcccg gaacctggag     960
gggcaccacc agattgccgc agcctgcttt ctgccttcct attgctggct tgtctgtgct    1020
actttgcact tcctgcatgc tcccacacct gctggtcaga ccctcacaag catctatacc    1080
agctttctac gcctgaactt cagtggggaa acactggaca gcacccacac gtccaatcta    1140
tccctgatgt cctatgcagc ccggactatg ggcaagctgg cctacgaggg cgtgccatcc    1200
cgaaagacct acttctctga agaggatgtc cgtggctgcc tggaagctgg catcaagaca    1260
gaggaagagt ttcaactgct tcagatcttc cgcagggacg ccctgaggtt tttcctggcc    1320
ccgtgtgtgg aaccagggca cctgggtacc ttcgtgttca ccgtgcccgc catgcaggag    1380
tatctggctg ccctctacag cgtgcttggt ttgcgcaaga cagccctgca gcgggtgggc    1440
```

-continued

```
aaagaagtgg ttgaatttgt gggccgtgtt ggggaagatg tcagcctggt attgggcatt    1500
gtggccaagc tgttgcccct gcggattctg cctctgctct tcaacttgct cgaattcgat    1560
tacaaggatg acgatgacaa gctcgagcac caccaccacc accactga                1608

<210> SEQ ID NO 38
<211> LENGTH: 23
<212> TYPE: DNA
<213> ORGANISM: Artificial Sequence
<220> FEATURE:
<223> OTHER INFORMATION: forward primer of C10-dTomato

<400> SEQUENCE: 38
cgcggatcca tggtgagcaa ggg                                              23

<210> SEQ ID NO 39
<211> LENGTH: 27
<212> TYPE: DNA
<213> ORGANISM: Artificial Sequence
<220> FEATURE:
<223> OTHER INFORMATION: reverse primer of C10-dTomato

<400> SEQUENCE: 39
cccaagcttt cactacttgt acagctc                                         27

<210> SEQ ID NO 40
<211> LENGTH: 783
<212> TYPE: DNA
<213> ORGANISM: Artificial Sequence
<220> FEATURE:
<223> OTHER INFORMATION: nucleic acid sequence encoding C10-dTomato

<400> SEQUENCE: 40
atgcggggtt ctcatcatca tcatcatcat ggtatggcta gcctcaggct gaggctacgg      60
cgctgtcatc gaggatccat ggtgagcaag ggcgaggagg tcatcaaaga gttcatgcgc     120
ttcaaggtgc gcatggaggg ctccatgaac ggccacgagt cgagatcga gggcgagggc      180 gagggccgcc cctacgaggg cacccagacc gccaagctga aggtgaccaa gggcggcccc     240
ctgcccttcg cctgggacat cctgtccccc cagttcatgt acggctccaa ggcgtacgtg     300 aagcacccg ccgacatccc cgattacaag aagctgtcct tccccgaggg cttcaagtgg      360
gagcgcgtga tgaacttcga ggacggcggt ctggtgaccg tgacccagga ctcctccctg     420
caggacggca cgctgatcta caaggtgaag atgcgcggca ccaacttccc ccccgacggc     480
cccgtaatgc agaagaagac catgggctgg gaggcctcca ccgagcgcct gtaccccgc      540 gacggcgtgc tgaagggcga gatccaccag gccctgaagc tgaaggacgg cggccactac     600
ctggtggagt tcaagaccat ctacatggcc aagaagcccg tgcaactgcc cggctactac     660
tacgtggaca ccaagctgga catcacctcc cacaacgagg actacaccat cgtggaacag     720
tacgagcgct ccgagggccg ccaccacctg ttcctgtacg gcatggacga gctgtacaag     780
tag                                                                   783

<210> SEQ ID NO 41
<211> LENGTH: 60
<212> TYPE: DNA
<213> ORGANISM: Artificial Sequence
<220> FEATURE:
<223> OTHER INFORMATION: forward primer of C10(m)-EGFP

<400> SEQUENCE: 41
```

```
ctagctagcc tcaggatgcg gctgaggcgc tgtcatcgag gatccgtgag caagggcgag      60

<210> SEQ ID NO 42
<211> LENGTH: 69
<212> TYPE: DNA
<213> ORGANISM: Artificial Sequence
<220> FEATURE:
<223> OTHER INFORMATION: reverse primer of C10(m)-EGFP

<400> SEQUENCE: 42
cccaagcttt tattacttgt acagctcgtc catgccgaga gtgatcccgg cggcggtcac      60
gaactccag                                                             69

<210> SEQ ID NO 43
<211> LENGTH: 795
<212> TYPE: DNA
<213> ORGANISM: Artificial Sequence
<220> FEATURE:
<223> OTHER INFORMATION: nucleic acid sequence encoding C10(m)-EGFP

<400> SEQUENCE: 43
atgcggggtt ctcatcatca tcatcatcat ggtatggcta gcctcaggat gaggctacgg      60
cgctgtcatc gaggatccgt gagcaagggc gaggagctgt tcaccggggt ggtgcccatc     120
ctggtcgagc tggacggcga cgtaaacggc cacaagttca gcgtgtccgg cgagggcgag     180
ggcgatgcca cctacggcaa gctgaccctg aagttcatct gcaccaccgg caagctgccc     240
gtgccctggc ccaccctcgt gaccaccctg acctacggcg tgcagtgctt cagccgctac     300
cccgaccaca tgaagcagca cgacttcttc aagtccgcca tgcccgaagg ctacgtccag     360
gagcgcacca tcttcttcaa ggacgacggc aactacaaga cccgcgccga ggtgaagttc     420
gagggcgaca ccctggtgaa ccgcatcgag ctgaagggca tcgacttcaa ggaggacggc     480
aacatcctgg ggcacaagct ggagtacaac tacaacagcc acaacgtcta tatcatggcc     540
gacaagcaga agaacggcat caaggtgaac ttcaagatcc gccacaacat cgaggacggc     600
agcgtgcagc tcgccgacca ctaccagcag aacacccca tcggcgacgg ccccgtgctg     660
ctgcccgaca accactacct gagcacccag tccgccctga gcaaagaccc caacgagaag     720
cgcgatcaca tggtcctgct ggagttcgtg accgccgccg ggatcactct cggcatggac     780
gagctgtaca agtaa                                                      795

<210> SEQ ID NO 44
<211> LENGTH: 60
<212> TYPE: DNA
<213> ORGANISM: Artificial Sequence
<220> FEATURE:
<223> OTHER INFORMATION: forward primer of C10(C>A)-EGFP

<400> SEQUENCE: 44
ctagctagcc tcaggctgag gctacggcgc gctcatcgag gatccgtgag caagggcgag      60

<210> SEQ ID NO 45
<211> LENGTH: 69
<212> TYPE: DNA
<213> ORGANISM: Artificial Sequence
<220> FEATURE:
<223> OTHER INFORMATION: reverse primer of C10(C>A)-EGFP

<400> SEQUENCE: 45
cccaagcttt tattacttgt acagctcgtc catgccgaga gtgatcccgg cggcggtcac      60
gaactccag                                                             69
```

-continued

```
<210> SEQ ID NO 46
<211> LENGTH: 795
<212> TYPE: DNA
<213> ORGANISM: Artificial Sequence
<220> FEATURE:
<223> OTHER INFORMATION: nucleic acid sequence encoding C10(C>A)-EGFP

<400> SEQUENCE: 46
atgcggggtt ctcatcatca tcatcatcat ggtatggcta gcctcaggct gaggctacgg      60
cgcgctcatc gaggatccgt gagcaagggc gaggagctgt tcaccggggt ggtgcccatc     120
ctggtcgagc tggacggcga cgtaaacggc cacaagttca gcgtgtccgg cgagggcgag     180
ggcgatgcca cctacggcaa gctgaccctg aagttcatct gcaccaccgg caagctgccc     240
gtgccctggc ccaccctcgt gaccaccctg acctacggcg tgcagtgctt cagccgctac     300
cccgaccaca tgaagcagca cgacttcttc aagtccgcca tgcccgaagg ctacgtccag     360
gagcgcacca tcttcttcaa ggacgacggc aactacaaga cccgcgccga ggtgaagttc     420
gagggcgaca ccctggtgaa ccgcatcgag ctgaagggca tcgacttcaa ggaggacggc     480
aacatcctgg ggcacaagct ggagtacaac tacaacagcc acaacgtcta tatcatggcc     540
gacaagcaga agaacggcat caaggtgaac ttcaagatcc gccacaacat cgaggacggc     600
agcgtgcagc tcgccgacca ctaccagcag aacacccca tcggcgacgg ccccgtgctg     660
ctgcccgaca ccactacct gagcacccag tccgccctga gcaaagaccc caacgagaag     720
cgcgatcaca tggtcctgct ggagttcgtg accgccgccg ggatcactct cggcatggac     780
gagctgtaca agtaa                                                     795

<210> SEQ ID NO 47
<211> LENGTH: 57
<212> TYPE: DNA
<213> ORGANISM: Artificial Sequence
<220> FEATURE:
<223> OTHER INFORMATION: forward primer of C10(L del)-EGFP

<400> SEQUENCE: 47
ctagctagca ggctgaggct acggcgctgt catcgaggat ccgtgagcaa gggcgag        57

<210> SEQ ID NO 48
<211> LENGTH: 69
<212> TYPE: DNA
<213> ORGANISM: Artificial Sequence
<220> FEATURE:
<223> OTHER INFORMATION: reverse primer of C10(L del)-EGFP

<400> SEQUENCE: 48
cccaagcttt tattacttgt acagctcgtc catgccgaga gtgatcccgg cggcggtcac      60
gaactccag                                                             69

<210> SEQ ID NO 49
<211> LENGTH: 792
<212> TYPE: DNA
<213> ORGANISM: Artificial Sequence
<220> FEATURE:
<223> OTHER INFORMATION: nucleic acid sequence encoding C10(L del)-EGFP

<400> SEQUENCE: 49
atgcggggtt ctcatcatca tcatcatcat ggtatggcta gcaggctgag gctacggcgc      60
tgtcatcgag gatccgtgag caagggcgag gagctgttca ccggggtggt gcccatcctg     120
```

-continued

```
gtcgagctgg acggcgacgt aaacggccac aagttcagcg tgtccggcga gggcgagggc    180
gatgccacct acggcaagct gaccctgaag ttcatctgca ccaccggcaa gctgcccgtg    240
ccctggccca ccctcgtgac caccctgacc tacggcgtgc agtgcttcag ccgctacccc    300
gaccacatga gcagcacga  cttcttcaag tccgccatgc ccgaaggcta cgtccaggag    360
cgcaccatct tcttcaagga cgacggcaac tacaagaccc gcgccgaggt gaagttcgag    420
ggcgacaccc tggtgaaccg catcgagctg aagggcatcg acttcaagga ggacggcaac    480
atcctggggc acaagctgga gtacaactac aacagccaca cgtctatat  catggccgac    540 aagcagaaga acggcatcaa ggtgaacttc aagatccgcc acaacatcga ggacggcagc    600
gtgcagctcg ccgaccacta ccagcagaac acccccatcg gcgacggccc cgtgctgctg    660
cccgacaacc actacctgag cacccagtcc gccctgagca agacccccaa cgagaagcgc    720
gatcacatgg tcctgctgga gttcgtgacc gccgccggga tcactctcgg catggacgag    780
ctgtacaagt aa                                                        792

<210> SEQ ID NO 50
<211> LENGTH: 57
<212> TYPE: DNA
<213> ORGANISM: Artificial Sequence
<220> FEATURE:
<223> OTHER INFORMATION: forward primer of C10(R del)-EGFP

<400> SEQUENCE: 50
ctagctagcc tcaggctgag gctacggcgc tgtcatggat ccgtgagcaa gggcgag       57

<210> SEQ ID NO 51
<211> LENGTH: 69
<212> TYPE: DNA
<213> ORGANISM: Artificial Sequence
<220> FEATURE:
<223> OTHER INFORMATION: reverse primer of C10(R del)-EGFP

<400> SEQUENCE: 51
cccaagcttt tattacttgt acagctcgtc catgccgaga gtgatcccgg cggcggtcac     60
gaactccag                                                             69

<210> SEQ ID NO 52
<211> LENGTH: 792
<212> TYPE: DNA
<213> ORGANISM: Artificial Sequence
<220> FEATURE:
<223> OTHER INFORMATION: nucleic acid sequence encoding C10(R del)-EGFP

<400> SEQUENCE: 52
atgcggggtt ctcatcatca tcatcatcat ggtatggcta gcctcaggct gaggctacgg     60
cgctgtcatg gatccgtgag caagggcgag gagctgttca ccggggtggt gcccatcctg    120
gtcgagctgg acggcgacgt aaacggccac aagttcagcg tgtccggcga gggcgagggc    180
gatgccacct acggcaagct gaccctgaag ttcatctgca ccaccggcaa gctgcccgtg    240
ccctggccca ccctcgtgac caccctgacc tacggcgtgc agtgcttcag ccgctacccc    300
gaccacatga gcagcacga  cttcttcaag tccgccatgc ccgaaggcta cgtccaggag    360
cgcaccatct tcttcaagga cgacggcaac tacaagaccc gcgccgaggt gaagttcgag    420
ggcgacaccc tggtgaaccg catcgagctg aagggcatcg acttcaagga ggacggcaac    480
atcctggggc acaagctgga gtacaactac aacagccaca cgtctatat  catggccgac    540 aagcagaaga acggcatcaa ggtgaacttc aagatccgcc acaacatcga ggacggcagc    600
```

-continued

```
gtgcagctcg ccgaccacta ccagcagaac acccccatcg gcgacggccc cgtgctgctg        660
cccgacaacc actacctgag cacccagtcc gccctgagca agacccccaa cgagaagcgc        720
gatcacatgg tcctgctgga gttcgtgacc gccgccggga tcactctcgg catggacgag        780
ctgtacaagt aa        792

<210> SEQ ID NO 53
<211> LENGTH: 57
<212> TYPE: DNA
<213> ORGANISM: Artificial Sequence
<220> FEATURE:
<223> OTHER INFORMATION: forward primer of C10(L>R)-EGFP

<400> SEQUENCE: 53
ctagctagca agaggctgag gctacggcgc tgtcatggat ccgtgagcaa gggcgag        57

<210> SEQ ID NO 54
<211> LENGTH: 69
<212> TYPE: DNA
<213> ORGANISM: Artificial Sequence
<220> FEATURE:
<223> OTHER INFORMATION: reverse primer of C10(L>R)-EGFP

<400> SEQUENCE: 54
cccaagcttt tattacttgt acagctcgtc catgccgaga gtgatcccgg cggcggtcac        60
gaactccag        69

<210> SEQ ID NO 55
<211> LENGTH: 795
<212> TYPE: DNA
<213> ORGANISM: Artificial Sequence
<220> FEATURE:
<223> OTHER INFORMATION: nucleic acid sequence encoding C10(L>R)-EGFP

<400> SEQUENCE: 55
atgcggggtt ctcatcatca tcatcatcat ggtatggcta gcaagaggct gaggctacgg        60
cgctgtcatc gaggatccgt gagcaagggc gaggagctgt tcaccggggt ggtgcccatc       120
ctggtcgagc tggacggcga cgtaaacggc cacaagttca gcgtgtccgg cgagggcgag       180
ggcgatgcca cctacggcaa gctgaccctg aagttcatct gcaccaccgg caagctgccc       240
gtgccctggc ccaccctcgt gaccaccctg acctacggcg tgcagtgctt cagccgctac       300
cccgaccaca tgaagcagca cgacttcttc aagtccgcca tgcccgaagg ctacgtccag       360
gagcgcacca tcttcttcaa ggacgacggc aactacaaga cccgcgccga ggtgaagttc       420
gagggcgaca ccctggtgaa ccgcatcgag ctgaagggca tcgacttcaa ggaggacggc       480
aacatcctgg ggcacaagct ggagtacaac tacaacagcc acaacgtcta tatcatggcc       540
gacaagcaga agaacggcat caaggtgaac ttcaagatcc gccacaacat cgaggacggc       600
agcgtgcagc tcgccgacca ctaccagcag aacaccccca tcggcgacgg ccccgtgctg       660
ctgcccgaca accactacct gagcacccag tccgccctga gcaaagaccc caacgagaag       720
cgcgatcaca tggtcctgct ggagttcgtg accgccgccg ggatcactct cggcatggac       780
gagctgtaca agtaa        795

<210> SEQ ID NO 56
<211> LENGTH: 57
<212> TYPE: DNA
<213> ORGANISM: Artificial Sequence
<220> FEATURE:
```

<223> OTHER INFORMATION: forward primer of C10(L>K)-EGFP

<400> SEQUENCE: 56
ctagctagcc ggaggctgag gctacggcgc tgtcatggat ccgtgagcaa gggcgag          57

<210> SEQ ID NO 57
<211> LENGTH: 69
<212> TYPE: DNA
<213> ORGANISM: Artificial Sequence
<220> FEATURE:
<223> OTHER INFORMATION: reverse primer of C10(L>K)-EGFP

<400> SEQUENCE: 57
cccaagcttt tattacttgt acagctcgtc catgccgaga gtgatcccgg cggcggtcac          60
gaactccag                                                               69

<210> SEQ ID NO 58
<211> LENGTH: 795
<212> TYPE: DNA
<213> ORGANISM: Artificial Sequence
<220> FEATURE:
<223> OTHER INFORMATION: nucleic acid sequence encoding C10(L>K)-EGFP

<400> SEQUENCE: 58
atgcggggtt ctcatcatca tcatcatcat ggtatggcta gccggaggct gaggctacgg          60
cgctgtcatc gaggatccgt gagcaagggc gaggagctgt tcaccggggt ggtgcccatc          120
ctggtcgagc tggacggcga cgtaaacggc cacaagttca gcgtgtccgg cgagggcgag          180
ggcgatgcca cctacggcaa gctgaccctg aagttcatct gcaccaccgg caagctgccc          240
gtgccctggc ccaccctcgt gaccaccctg acctacggcg tgcagtgctt cagccgctac          300
cccgaccaca tgaagcagca cgacttcttc aagtccgcca tgcccgaagg ctacgtccag          360
gagcgcacca tcttcttcaa ggacgacggc aactacaaga cccgcgccga ggtgaagttc          420
gagggcgaca ccctggtgaa ccgcatcgag ctgaagggca tcgacttcaa ggaggacggc          480
aacatcctgg ggcacaagct ggagtacaac tacaacagcc acaacgtcta tatcatggcc          540
gacaagcaga agaacggcat caaggtgaac ttcaagatcc gccacaacat cgaggacggc          600
agcgtgcagc tcgccgacca ctaccagcag aacacccca tcggcgacgg ccccgtgctg          660
ctgcccgaca accactacct gagcacccag tccgccctga gcaaagaccc caacgagaag          720
cgcgatcaca tggtcctgct ggagttcgtg accgccgccg ggatcactct cggcatggac          780
gagctgtaca agtaa                                                        795

<210> SEQ ID NO 59
<211> LENGTH: 51
<212> TYPE: DNA
<213> ORGANISM: Artificial Sequence
<220> FEATURE:
<223> OTHER INFORMATION: forward primer of TP-EGFP

<400> SEQUENCE: 59
ctagctagca agaagaggag aaaaaggaaa ggatccgtga gcaagggcga g                   51

<210> SEQ ID NO 60
<211> LENGTH: 69
<212> TYPE: DNA
<213> ORGANISM: Artificial Sequence
<220> FEATURE:
<223> OTHER INFORMATION: reverse primer of TP-EGFP

<400> SEQUENCE: 60

-continued

```
cccaagcttt tattacttgt acagctcgtc catgccgaga gtgatcccgg cggcggtcac      60
gaactccag                                                             69

<210> SEQ ID NO 61
<211> LENGTH: 786
<212> TYPE: DNA
<213> ORGANISM: Artificial Sequence
<220> FEATURE:
<223> OTHER INFORMATION: nucleic acid sequence encoding TP-EGFP

<400> SEQUENCE: 61
atgcggggtt ctcatcatca tcatcatcat ggtatggcta gcaagaagag gagaaaaagg      60
aaaggatccg tgagcaaggg cgaggagctg ttcaccgggg tggtgcccat cctggtcgag     120
ctggacggcg acgtaaacgg ccacaagttc agcgtgtccg gcgagggcga gggcgatgcc     180
acctacggca agctgaccct gaagttcatc tgcaccaccg gcaagctgcc cgtgccctgg     240
cccaccctcg tgaccaccct gacctacggc gtgcagtgct tcagccgcta ccccgaccac     300
atgaagcagc acgacttctt caagtccgcc atgcccgaag ctacgtcca ggagcgcacc      360 atcttcttca aggacgacgg caactacaag acccgcgccg aggtgaagtt cgagggcgac     420
accctggtga accgcatcga gctgaagggc atcgacttca aggaggacgg caacatcctg     480
gggcacaagc tggagtacaa ctacaacagc cacaacgtct atatcatggc cgacaagcag     540
aagaacggca tcaaggtgaa cttcaagatc cgccacaaca tcgaggacgg cagcgtgcag     600
ctcgccgacc actaccagca gaacacccc atcggcgacg gccccgtgct gctgcccgac      660
aaccactacc tgagcaccca gtccgccctg agcaaagacc ccaacgagaa gcgcgatcac     720
atggtcctgc tggagttcgt gaccgccgcc gggatcactc tcggcatgga cgagctgtac     780
aagtaa                                                                786

<210> SEQ ID NO 62
<211> LENGTH: 58
<212> TYPE: DNA
<213> ORGANISM: Artificial Sequence
<220> FEATURE:
<223> OTHER INFORMATION: forward primer of TB-EGFP

<400> SEQUENCE: 62
ctagctagcc tgcgtctgct gaggctcaag ttaaaaagga tccgtgagca agggcgag        58

<210> SEQ ID NO 63
<211> LENGTH: 69
<212> TYPE: DNA
<213> ORGANISM: Artificial Sequence
<220> FEATURE:
<223> OTHER INFORMATION: reverse primer of TB-EGFP

<400> SEQUENCE: 63
cccaagcttt tattacttgt acagctcgtc catgccgaga gtgatcccgg cggcggtcac      60
gaactccag                                                             69

<210> SEQ ID NO 64
<211> LENGTH: 792
<212> TYPE: DNA
<213> ORGANISM: Artificial Sequence
<220> FEATURE:
<223> OTHER INFORMATION: nucleic acid sequence encoding TB-EGFP

<400> SEQUENCE: 64
```
atgcggggtt ctcatcatca tcatcatcat ggtatggcta gcctgcgtct gctgaggctc    60
aagttaaaag gatccgtgag caagggcgag gagctgttca ccggggtggt gcccatcctg   120
gtcgagctgg acggcgacgt aaacggccac aagttcagcg tgtccggcga gggcgagggc   180
gatgccacct acggcaagct gaccctgaag ttcatctgca ccaccggcaa gctgcccgtg   240
ccctggccca ccctcgtgac caccctgacc tacggcgtgc agtgcttcag ccgctacccc   300
gaccacatga gcagcacga cttcttcaag tccgccatgc ccgaaggcta cgtccaggag   360
cgcaccatct tcttcaagga cgacggcaac tacaagaccc gcgccgaggt gaagttcgag   420
ggcgacaccc tggtgaaccg catcgagctg aagggcatcg acttcaagga ggacggcaac   480
atcctggggc acaagctgga gtacaactac aacagccaca cgtctatat catggccgac   540 aagcagaaga acggcatcaa ggtgaacttc aagatccgcc acaacatcga ggacggcagc   600
gtgcagctcg ccgaccacta ccagcagaac accccatcg gcgacggccc cgtgctgctg   660
cccgacaacc actacctgag cacccagtcc gccctgagca agacccccaa cgagaagcgc   720
gatcacatgg tcctgctgga gttcgtgacc gccgccggga tcactctcgg catggacgag   780
ctgtacaagt aa                                                        792

<210> SEQ ID NO 65
<211> LENGTH: 63
<212> TYPE: DNA
<213> ORGANISM: Artificial Sequence
<220> FEATURE:
<223> OTHER INFORMATION: forward primer of TAT-EGFP

<400> SEQUENCE: 65
ctagctagct atggacgcaa gaagcgccgc cagcgccgcc gcggatccgt gagcaagggc    60
gag                                                                   63

<210> SEQ ID NO 66
<211> LENGTH: 69
<212> TYPE: DNA
<213> ORGANISM: Artificial Sequence
<220> FEATURE:
<223> OTHER INFORMATION: reverse primer of TAT-EGFP

<400> SEQUENCE: 66
cccaagcttt tattacttgt acagctcgtc catgccgaga gtgatcccgg cggcggtcac    60
gaactccag                                                             69

<210> SEQ ID NO 67
<211> LENGTH: 798
<212> TYPE: DNA
<213> ORGANISM: Artificial Sequence
<220> FEATURE:
<223> OTHER INFORMATION: nucleic acid sequence encoding TAT-EGFP

<400> SEQUENCE: 67
atgcggggtt ctcatcatca tcatcatcat ggtatggcta gctatggacg caagaagcgc    60
cgccagcgcc gccgcggatc cgtgagcaag ggcgaggagc tgttcaccgg ggtggtgccc   120
atcctggtcg agctggacgg cgacgtaaac ggccacaagt tcagcgtgtc cggcgagggc   180
gagggcgatg ccacctacgg caagctgacc ctgaagttca tctgcaccac cggcaagctg   240
cccgtgccct ggcccaccct cgtgaccacc ctgacctacg gcgtgcagtg cttcagccgc   300
taccccgacc acatgaagca gcacgacttc ttcaagtccg ccatgcccga aggctacgtc   360
caggagcgca ccatcttctt caaggacgac ggcaactaca gacccgcgc cgaggtgaag   420

-continued

```
ttcgagggcg acaccctggt gaaccgcatc gagctgaagg gcatcgactt caaggaggac      480
ggcaacatcc tggggcacaa gctggagtac aactacaaca gccacaacgt ctatatcatg      540
gccgacaagc agaagaacgg catcaaggtg aacttcaaga tccgccacaa catcgaggac      600
ggcagcgtgc agctcgccga ccactaccag cagaacaccc ccatcggcga cggccccgtg      660
ctgctgcccg acaaccacta cctgagcacc cagtccgccc tgagcaaaga ccccaacgag      720
aagcgcgatc acatggtcct gctggagttc gtgaccgccg ccgggatcac tctcggcatg      780
gacgagctgt acaagtaa                                                    798
```

<210> SEQ ID NO 68
<211> LENGTH: 23
<212> TYPE: DNA
<213> ORGANISM: Artificial Sequence
<220> FEATURE:
<223> OTHER INFORMATION: forward primer of TAT-dTomato

<400> SEQUENCE: 68

```
cgcggatcca tggtgagcaa ggg                                               23
```

<210> SEQ ID NO 69
<211> LENGTH: 27
<212> TYPE: DNA
<213> ORGANISM: Artificial Sequence
<220> FEATURE:
<223> OTHER INFORMATION: reverse primer of TAT-dTomato

<400> SEQUENCE: 69

```
cccaagcttt cactacttgt acagctc                                           27
```

<210> SEQ ID NO 70
<211> LENGTH: 786
<212> TYPE: DNA
<213> ORGANISM: Artificial Sequence
<220> FEATURE:
<223> OTHER INFORMATION: nucleic acid sequence encoding TAT-dTomato

<400> SEQUENCE: 70

```
atgcggggtt ctcatcatca tcatcatcat ggtatggcta gctatggacg caagaagcgc       60
cgccagcgcc gccgcggatc catggtgagc aagggcgagg aggtcatcaa agagttcatg      120
cgcttcaagg tgcgcatgga gggctccatg aacggcacg agttcgagat cgagggcgag      180
ggcgagggcc gcccctacga gggcacccag accgccaagc tgaaggtgac caagggcggc      240
cccctgccct tcgcctggga catcctgtcc ccccagttca tgtacggctc caaggcgtac      300
gtgaagcacc ccgccgacat ccccgattac aagaagctgt ccttccccga gggcttcaag      360
tgggagcgcg tgatgaactt cgaggacggc ggtctggtga ccgtgaccca ggactcctcc      420
ctgcaggacg gcacgctgat ctacaaggtg aagatgcgcg gcaccaactt cccccccgac      480
ggccccgtaa tgcagaagaa gaccatgggc tgggaggcct ccaccgagcg cctgtacccc      540
cgcgacggcg tgctgaaggg cgagatccac caggccctga gctgaagga cggcggccac      600 tacctggtgg agttcaagac catctacatg gccaagaagc ccgtgcaact gcccggctac      660
tactacgtgg acaccaagct ggacatcacc tcccacaacg aggactacac catcgtggaa      720
cagtacgagc gctccgaggg ccgccaccac ctgttcctgt acggcatgga cgagctgtac      780
aagtag                                                                 786
```

<210> SEQ ID NO 71

```
<211> LENGTH: 102
<212> TYPE: DNA
<213> ORGANISM: Artificial Sequence
<220> FEATURE:
<223> OTHER INFORMATION: forward primer of dNP2-EGFP

<400> SEQUENCE: 71
ctagctagca aaattaaaaa agtcaagaag aaaggaagaa aaggatccaa aattaaaaaa      60
gtcaagaaga aaggaagaaa aggatccgtg agcaagggcg ag                       102

<210> SEQ ID NO 72
<211> LENGTH: 69
<212> TYPE: DNA
<213> ORGANISM: Artificial Sequence
<220> FEATURE:
<223> OTHER INFORMATION: reverse primer of dNP2-EGFP

<400> SEQUENCE: 72
cccaagcttt tattacttgt acagctcgtc catgccgaga gtgatcccgg cggcggtcac      60
gaactccag                                                             69

<210> SEQ ID NO 73
<211> LENGTH: 837
<212> TYPE: DNA
<213> ORGANISM: Artificial Sequence
<220> FEATURE:
<223> OTHER INFORMATION: nucleic acid sequence encoding dNP2-EGFP

<400> SEQUENCE: 73
atgcggggtt ctcatcatca tcatcatcat ggtatggcta gcaaaattaa aaaagtcaag      60
aagaaaggaa gaaaaggatc caaaattaaa aaagtcaaga agaaaggaag aaaaggatcc     120
gtgagcaagg gcgaggagct gttcaccggg gtggtgccca tcctggtcga gctggacggc     180
gacgtaaacg gccacaagtt cagcgtgtcc ggcgagggcg agggcgatgc cacctacggc     240
aagctgaccc tgaagttcat ctgcaccacc ggcaagctgc ccgtgccctg cccaccctc      300 gtgaccaccc tgacctacgg cgtgcagtgc ttcagccgct accccgacca catgaagcag     360
cacgacttct tcaagtccgc catgcccgaa ggctacgtcc aggagcgcac catcttcttc     420
aaggacgacg gcaactacaa gacccgcgcc gaggtgaagt tcgagggcga caccctggtg     480
aaccgcatcg agctgaaggg catcgacttc aaggaggacg gcaacatcct ggggcacaag     540
ctggagtaca actacaacag ccacaacgtc tatatcatgg ccgacaagca gaagaacggc     600
atcaaggtga acttcaagat ccgccacaac atcgaggacg gcagcgtgca gctcgccgac     660
cactaccagc agaacacccc catcggcgac ggccccgtgc tgctgcccga caaccactac     720
ctgagcaccc agtccgccct gagcaaagac cccaacgaga gcgcgatca catggtcctg      780 ctggagttcg tgaccgccgc cgggatcact ctcggcatgg acgagctgta caagtaa        837

<210> SEQ ID NO 74
<211> LENGTH: 63
<212> TYPE: DNA
<213> ORGANISM: Artificial Sequence
<220> FEATURE:
<223> OTHER INFORMATION: forward primer of TAT-LRR

<400> SEQUENCE: 74
ctagctagct atggacgcaa gaagcgccgc cagcgccgcc gcgtcgacct tcttgaccat      60
ctc                                                                   63
```

-continued

```
<210> SEQ ID NO 75
<211> LENGTH: 22
<212> TYPE: DNA
<213> ORGANISM: Artificial Sequence
<220> FEATURE:
<223> OTHER INFORMATION: reverse primer of TAT-LRR

<400> SEQUENCE: 75
aggttctgga cacgaattcc gg                                                   22

<210> SEQ ID NO 76
<211> LENGTH: 1068
<212> TYPE: DNA
<213> ORGANISM: Artificial Sequence
<220> FEATURE:
<223> OTHER INFORMATION: necleic acid sequence encoding TAT-LRR

<400> SEQUENCE: 76
atgggcagca gccatcatca tcatcatcac agcagcggcc tggtgccgcg cggcagccat      60
atggctagct atggacgcaa gaagcgccgc cagcgccgcc gcgtcgacct tcttgaccat     120
ctcttcttcc actatgagtt ccagaaccag cgcttctcag ctgaggtgct gggctcccta     180
cgccagctca atttagcagg ggtgcgcatg acacccctca agtgcacagt ggtagcctct     240
gtactgggaa gtggaaggca cccctggat gaggtgaact tggcctcctg ccagctggat     300
cccgctgggc tacacactct catgcctgtc ctcctgcgtg cccggaaact ggggttgcaa     360
ctcaacaatc tgggccccga ggcctgcaga gacctccgag acctgctctt acacgatcaa     420
tgccagatca ccactcttag gctctccaac aacccactga cagcagctgg tgtgggctta     480
ctgatggacg ggctggcagg aaacacttcg gtgacacacc tgtctctgct gcacactgac     540
cttggagacg agggactgga actgctggct gcccagctgg accgaaacaa acaactgcag     600
gagctgaacg tggcctacaa cggtgctggt gacacagtgg ctctggcctt ggctaaggct     660
gctcgggagc acccttccct ggagctgctg cacctctact tcaatgagct gagttcagag     720
ggccgccagg tcctgcggga tttggggggc tctggtgaag gtggtgcccg ggtcgtagcc     780
tcgctgacag aagggacggc ggtgtctgag tactggtcag tgatccttag tgaagtccag     840
cgcaacgtcc acagctggga cccgctccgg gtccagaggc atctcaagct gctgctccgt     900
gatctggagg acagccgggg cgccacccttt aatccctggc gcaaggctca gcttctgcga     960
gtggagggcg aggtcaagac tcttctggag cagctgggag gttctggaca cgaattcgat    1020
tacaaggatg acgatgacaa gctcgagcac caccaccacc accactga                  1068

<210> SEQ ID NO 77
<211> LENGTH: 18
<212> TYPE: PRT
<213> ORGANISM: Artificial Sequence
<220> FEATURE:
<223> OTHER INFORMATION: Cell penetrating peptide of formula 1
<220> FEATURE:
<221> NAME/KEY: MISC_FEATURE
<222> LOCATION: (1)..(5)
<223> OTHER INFORMATION: Xaa = absent or any one of leucine, arginine,
      or lysine
<220> FEATURE:
<221> NAME/KEY: MISC_FEATURE
<222> LOCATION: (7)
<223> OTHER INFORMATION: Xaa = any one of alanine, glycine, proline,
      tryptophan, phenylalanine, leucine, isoleucine, methionine, or
      valine
<220> FEATURE:
<221> NAME/KEY: MISC_FEATURE
<222> LOCATION: (12)
<223> OTHER INFORMATION: Xaa = any one of alanine, glycine, proline,
```

-continued

```
        tryptophan, phenylalanine, leucine, isoleucine, methionine,
        valine, serine, threonine, cysteine, tyrosine, asparagine, or
        glutamine
<220> FEATURE:
<221> NAME/KEY: MISC_FEATURE
<222> LOCATION: (14)..(18)
<223> OTHER INFORMATION: Xaa = absent or any one of arginine, lysine, or
        histidine

<400> SEQUENCE: 77

Xaa Xaa Xaa Xaa Xaa Arg Xaa Arg Leu Arg Arg Xaa His Xaa Xaa Xaa
1               5                   10                  15

Xaa Xaa
```

CELL PENETRATING PEPTIDES AND USES THEREOF

CROSS-REFERENCE TO RELATED APPLICATIONS

This application claims priority under 35 U.S.C. § 119 to Korean Patent Application No. 10-2021-0069432 filed on May 28, 2021 in the Korean Intellectual Property Office, the disclosure of which is incorporated herein by reference in its entirety.

INCORPORATION BY REFERENCE OF SEQUENCE LISTING

The content of the electronically submitted sequence listing, file name: Q276288 Substitute_Sequence_Listing_As_Filed.xml; size: 55.7 KB; and date of creation: May 11, 2025, filed herewith, is incorporated herein by reference in its entirety.

BACKGROUND OF THE INVENTION

1. Field of the Invention

The present invention relates to novel cell penetrating peptides, and more specifically to cytokine-derived cell penetrating peptides and uses thereof.

2. Description of the Related Art

Macrophages are one of the important innate immune cells that make up our body and are distributed in various types in all tissues. Macrophages play a role in protecting the body through phagocytosis against invading foreign pathogens and toxic substances under normal conditions. In addition, the function of macrophages is very important for major immune responses such as adaptive immunity, wound healing, and inflammatory response. The morphology and role of macrophages are very diverse; they can be divided into macrophages that specifically reside in tissues (microglial cells in the brain or Kupffer cells in the liver) and monocytes that circulate through blood. Both types of macrophages can regulate their activity through interactions with other adjacent cells, and on the contrary, activated macrophages may affect the surrounding environment. As such, macrophages perform important functions for maintaining homeostasis in our body, and abnormalities in the function of macrophages can cause various diseases, so studies to understand macrophages are being actively conducted.

Cell permeable peptide (or cell penetrating peptide) is a type of signal peptide and refers to a combination of specific amino acid sequences that is used for the purpose of delivering macromolecules (for example, proteins, DNA, and RNA) into cells. Cell penetrating peptides are composed of about 7 to about 30 amino acid sequences.

TAT peptide, well known as a cell penetrating peptide, is a β-galactosidase (120 kDa) consisting of 11 amino acid sequences present in the TAT protein derived from HIV. TAT peptide is currently used in various applications such as cellular therapeutics and diagnostic reagents. Other representative first-generation cell penetrating peptides include antennapedia (Penetratin) derived from *Drosophila* protein, VP22 derived from HSV-1, and Pep-1 derived from Simian Virus 40 large antigen T. Simple peptides, including polyarginines and polylysines in which several cationic amino acids such as arginine and lysine residues are repeatedly linked in sequence, respectively, have also been reported to have high cell permeability. However, most cell penetrating peptides are not sequences derived from human proteins, involve the possibility of immunogenicity and toxicity, and have the disadvantage of poor delivery efficacy to human cells. Under these circumstances, research has been conducted on novel cell penetrating peptides derived from human proteins. Cell penetrating peptides such as Hph-1, Vectocell, Lactoferrin, Sim-2, LPIN3, 21L-1a, and dNP2 are sequences derived from human proteins and they are considered second-generation ones.

Such conventional cell penetrating peptides are sequences derived from viral proteins such as HIV-1 or proteins expressed by other species such as *Drosophila* or are amino acid sequences artificially synthesized from characteristic amino acid sequences selected by amino acid sequencing of already known cell penetrating peptides. For these reasons, conventional cell penetrating peptides may cause side effects such as immune responses when applied to the human body.

Since these conventional cell penetrating peptides consist of relatively long amino acid chains, they are more likely to cause unwanted immune responses and affect the structure and function of proteins to be delivered, losing their efficiency when linked to biologically active substances to be delivered into cells.

The inventors of the present invention have demonstrated that peptide sequences derived from human cytokines exhibit potent delivery efficiency to macrophages compared to TAT, a cell penetrating peptide, and previously known skin penetrating peptides, thereby completing the present invention.

PRIOR ART DOCUMENTS

Patent Documents

Patent Document 1. Korean Patent Publication No. 10-2010-00011091

SUMMARY OF THE INVENTION

It is one object of the present invention to provide a cell penetrating peptide that has a high affinity for immune cells, particularly macrophages, unlike conventional cell penetrating peptides, achieving potent delivery efficiency of a biologically active substance to macrophages.

It is another object of the present invention to provide a composition for delivering a biologically active substance, a composition for gene therapy, a method for delivering a biologically active substance, and a method for gene therapy that use the cell penetrating peptide.

The present invention provides a cell penetrating peptide including an amino acid sequence represented by the following formula 1:

$$(Xaa1)_a\text{-Arg-Xaa2-Arg-Leu-Arg-Arg-Xaa3-His-}(Xaa4)_b \quad \text{(1) (SEQ ID NO: 77)}$$

wherein each Xaa1 is independently an amino acid selected from the group consisting of leucine, arginine, and lysine, Xaa2 is an amino acid selected from the group consisting of alanine, glycine, proline, tryptophan, phenylalanine, leucine, isoleucine, methionine, and valine, Xaa3 is an amino acid selected from the group consisting of alanine, glycine, proline, tryptophan, phenylalanine, leucine, isoleucine, methionine, valine, serine, threonine, cysteine, tyrosine, asparagine, and glutamine, each Xaa4 is independently an amino acid selected from the group consisting of arginine, lysine, and histidine, a is an integer from 0 to 5, and b is an integer from 0 to 5.

The cell penetrating peptide may be composed of 8 to 12 amino acids.

Each Xaa1 may be independently leucine.

Xaa3 may be alanine or cysteine and Xaa4 may be arginine.

Xaa2 may be selected from leucine and methionine.

The cell penetrating peptide may include the amino acid sequence set forth in SEQ ID NO: 1.

The present invention also provides a fusion product of the cell penetrating peptide and a biologically active substance.

The fusion product may target one or more types of immune cells selected from the group consisting of macrophages, B lymphocytes, T lymphocytes, mast cells, monocytes, dendritic cells, eosinophils, natural killer cells, basophils, and neutrophils.

The cell penetrating peptide may allow the fusion product to act specifically on macrophages such that the biologically active substance is efficiently delivered into macrophages.

The biologically active substance may be selected from the group consisting of proteins, nucleic acids, peptides, lipids, glycolipids, minerals, sugars, nanoparticles, biological agents, contrast materials, fluorescent materials, drugs, compounds, and combinations thereof.

The biologically active substance may be selected from the group consisting of agents inhibiting NF-κB signaling, agents inhibiting inflammasome signaling, and combinations thereof.

The biologically active substance may be linked to the N- or C-terminus of the cell penetrating peptide.

The present invention also provides a composition for delivering a biologically active substance into immune cells, the composition including the fusion product as an active ingredient.

The composition may be intended for local delivery of the biologically active substance to macrophages.

The present invention also provides a composition for use as a drug adjuvant, the composition including the fusion product as an active ingredient.

The present invention also provides a recombinant expression vector expressing a recombinant protein in which the cell penetrating peptide is fused to a biologically active substance.

The present invention also provides a recombinant expression vector including a DNA encoding the cell penetrating peptide and a DNA encoding a biologically active protein.

The present invention also provides a method for delivering a biologically active substance, the method including binding the cell penetrating peptide to the biologically active substance to prepare a delivery complex and injecting the delivery complex into the living body or cells of a non-human mammal.

The present invention also provides a method for gene therapy, the method including binding the cell penetrating peptide to a genetic material to prepare a delivery complex and injecting the delivery complex into the living body or cells of a non-human mammal.

The cell penetrating peptide of the present invention has the ability to effectively deliver a biologically active substance into phagocytes, particularly macrophages, both in vitro and in vivo. The cell penetrating peptide of the present invention can deliver a biologically active substance into macrophages with high efficiency compared to TAT peptide and dNP2 peptide that are commercially available as cell penetrating peptides.

In addition, the cell penetrating peptide of the present invention can be co-administered with a conventional therapeutic drug to macrophages to enhance the effect of the drug.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 45 shows the weights of animal models in Group 1 (PBS), Group 2 (C10-LRR), Group 3 ($\alpha$TNF$\alpha$Ab), and Group 4 (C10-LRR+$\alpha$TNF$\alpha$Ab), which were measured for 7 days;

FIG. 46 schematically shows an experimental design for determining the therapeutic effect of a combination of C10-LRR recombinant protein and $\alpha$TNF$\alpha$Ab on sepsis when the combination was administered once;

DETAILED DESCRIPTION OF THE INVENTION

Figure 1:
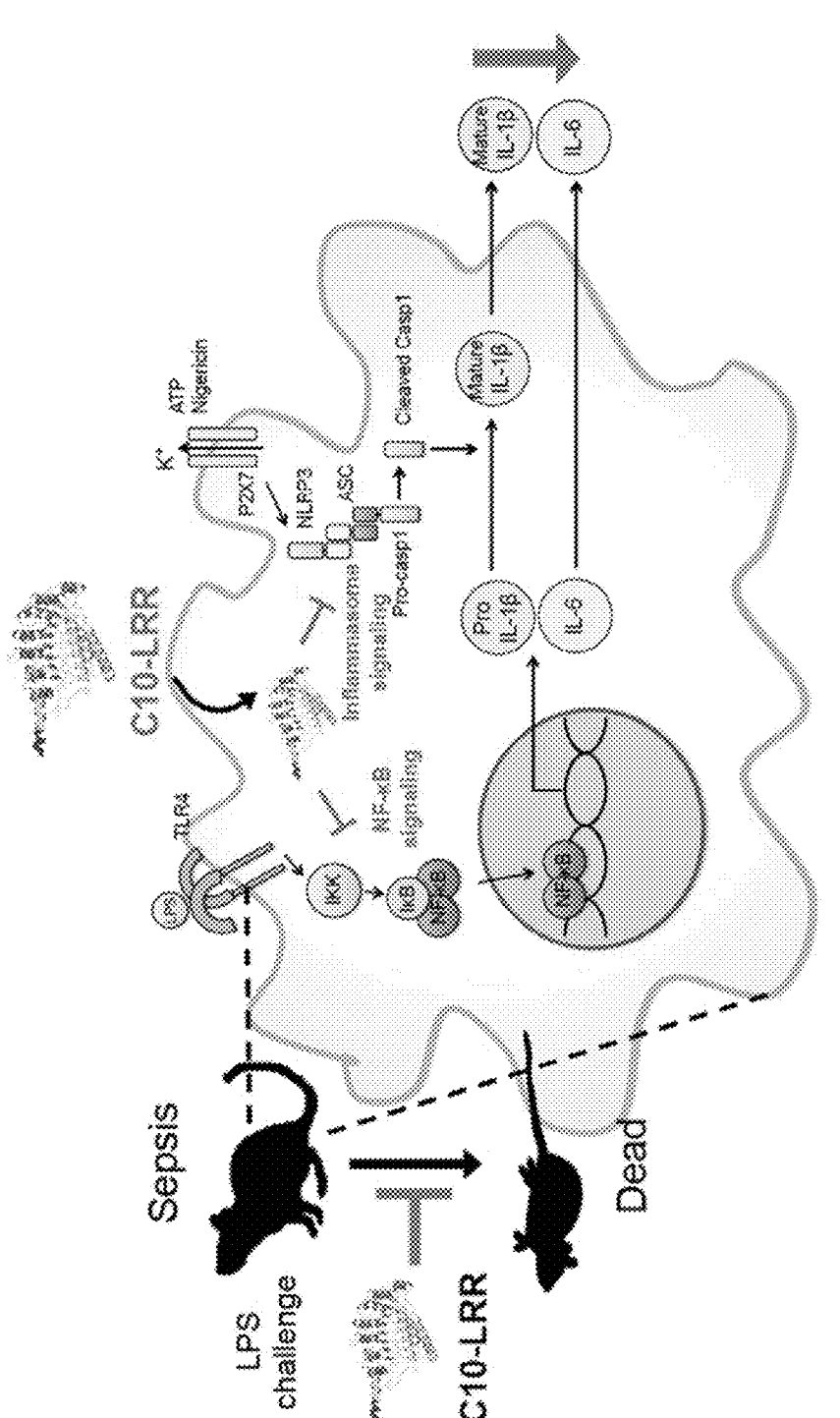
FIGS. 1 and 2 are a schematic diagram showing the pharmacological mechanism of C10-LRR against sepsis (FIG. 1) and a diagram showing the mechanism (FIG. 2)

The present invention will now be described in detail.

As used herein, the term "peptide" refers to a chained polymer of 4 to 1000 amino acid residues bonded together by peptide bonds. This term is used interchangeably with the term "polypeptide".

As used herein, the term "polynucleotide" refers to a polymer molecule composed of nucleotide monomers linked together in a chain via phosphate ester bonds. Here, each nucleotide monomer is made up of three units: a base, a sugar, and a phosphate.

As used herein, the term "cell penetrating peptide (CPP)" refers to a peptide capable of carrying a cargo of interest into cells in vitro or in vivo. This term is used interchangeably with the term "cell membrane penetrating domain" or "cell membrane penetrating peptide".

As used herein, the term "cargo" refers to a function regulating substance that is bound to the cell penetrating peptide and is delivered into cells where it has a biological activity to regulate all physiological phenomena in vivo. The cargo is meant to include all materials whose enhanced cell penetration efficiency is desired. The term "cargo" is used interchangeably herein to mean a "biologically active substance". Specifically, the biologically active substance may be selected from the group consisting of proteins, nucleic acids, peptides, lipids, glycolipids, minerals, sugars, nanoparticles, minerals, biological agents, contrast materials, drugs, compounds, and combinations thereof. More specifically, the biologically active substance may be a substance that is not easily transferred into cells via general routes.

As used herein, the term "biological activity" means an activity related to a physiological phenomenon or an activity related to a therapeutic purpose after intracellular or in vivo delivery.

As used herein, the term "recombinant cargo" refers to a complex in which a cell penetrating peptide and one or more cargos recombine with each other by genetic fusion or chemical bonding.

As used herein, the term "contact" means that the cargo or recombinant cargo is in contact with eukaryotic or prokaryotic cells. As a result of this contact, the cargo or recombinant cargo is delivered into the eukaryotic or prokaryotic cells.

The "introduction" of proteins, peptides, organic compounds, etc. into cells is used interchangeably with the expressions "transfer", "penetration", "transport", "delivery", "permeation", and "passage".

The present invention is directed to a cell penetrating peptide including an amino acid sequence represented by the following formula 1:

$$(Xaa1)_a\text{-Arg-Xaa2-Arg-Leu-Arg-Arg-Xaa3-His-}(Xaa4)_b \quad (1) \text{ (SEQ ID NO: 77)}$$

wherein each Xaa1 is independently an amino acid selected from the group consisting of leucine, arginine, and lysine, Xaa2 is an amino acid selected from the group consisting of alanine, glycine, proline, tryptophan, phenylalanine, leucine, isoleucine, methionine, and valine, Xaa3 is an amino acid selected from the group consisting of alanine, glycine, proline, tryptophan, phenylalanine, leucine, isoleucine, methionine, valine, serine, threonine, cysteine, tyrosine, asparagine, and glutamine, each Xaa4 is independently an amino acid selected from the group consisting of arginine, lysine, and histidine, and a and b are each independently an integer from 0 to 5, more preferably an integer of 0 or 1, most preferably 1.

The cell penetrating peptide is a sequence derived from human cytokine IL-10. The cell penetrating peptide is less likely to cause side effects such as immune responses when applied to the human body and enables efficient delivery to cells even when unique amino acids derived from human cytokine IL-10 are further added to the N- and C-termini of the amino acid sequence. Not only unique amino acids derived from human cytokine IL-10 but also other amino acids may be added to the cell penetrating peptide.

In the cell penetrating peptide, each Xaa1 is independently a non-polar or positively charged amino acid selected from alanine (Ala, A), glycine (Gly, G), proline (Pro, P), tryptophan (Trp, W), phenylalanine (Phe, F), leucine (Leu, L), isoleucine (Ile, I), methionine (Met, M), valine (Val, V), arginine (Arg, R), lysine (Lys, K), and histidine (His, H). Preferably, each Xaa1 is independently selected from leucine, arginine, and lysine. Each Xaa1 is most preferably leucine.

In the cell penetrating peptide, Xaa2 is a non-polar amino acid selected from alanine (Ala, A), glycine (Gly, G), proline (Pro, P), tryptophan (Trp, W), phenylalanine (Phe, F), leucine (Leu, L), isoleucine (Ile, I), methionine (Met, M), and valine (Val, V). Xaa2 is preferably selected from leucine and methionine.

In the cell penetrating peptide, Xaa3 is a non-polar or polar amino acid selected from alanine (Ala, A), glycine (Gly, G), proline (Pro, P), tryptophan (Trp, W), phenylalanine (Phe, F), leucine (Leu, L), isoleucine (Ile, I), methionine (Met, M), valine (Val, V), serine (Ser, S), threonine (Thr, T), cysteine (Cys, C), tyrosine (Tyr, Y), asparagine (Asn, N), and glutamine (Gln, Q). Xaa3 is preferably selected from alanine and cysteine. Xaa3 is most preferably cysteine.

In the cell penetrating peptide, each Xaa4 is independently a positively charged amino acid selected from arginine (Arg, R), lysine (Lys, K), and histidine (His, H). Preferably, each Xaa4 is arginine.

$(Xaa1)_a$ is a chain of a amino acids corresponding to Xaa1. The a amino acids may be identical to or different from each other. Likewise, $(Xaa4)_b$ may also include the presence of b different amino acids.

The cell penetrating peptide is composed of 8 to 30 amino acids, 8 to 20 amino acids, more preferably 8 to 12 amino acids, most preferably 10 amino acids.

The cell penetrating peptide is very small in size enough to minimize any possible biological interference with an active substance. The cell penetrating peptide can penetrate in vivo and enables in vivo delivery into cells, preferably phagocytes, most preferably macrophages, when administered via a suitable route. Examples of such routes of administration include intravenous, intraperitoneal, intramuscular, subcutaneous, intradermal, nasal, mucosal, inhalation, and oral routes.

The cell penetrating peptide can efficiently and specifically deliver a biologically active substance to specific cells, tissues or organs, particularly immune cells, most preferably macrophages, avoiding the need for separate components such as ligands and receptors.

The cell penetrating peptide may be linked to a biologically active substance. In this case, the cell penetrating peptide may be indirectly linked to the biologically active substance by a cloning technique using an expression vector at the nucleotide level. Alternatively, the cell penetrating peptide may be directly linked with the biologically active substance by chemical or physical covalent or non-covalent bonding therebetween.

The cell penetrating peptide may include one or more of the amino acid sequences set forth in SEQ ID NOS: 1, 3, 5, 7, 9, 11, and 13, preferably one or more of the amino acid sequences set forth in SEQ ID NOS: 1, 3, 5, and 9, more preferably the amino acid sequence set forth in SEQ ID NO: 1 or 3, most preferably the amino acid sequence set forth in SEQ ID NO: 1.

The cell penetrating peptide may be naturally extracted or artificially synthesized or may be produced by a genetic recombination technique based on DNA sequences.

A further aspect of the present invention is directed to a fusion product of the cell penetrating peptide and a biologically active substance.

The fusion product of the present invention allows the biologically active substance to pass through cell membranes, through which biologically active substances could not easily enter cells, and act directly in cells. In addition, the fusion product of the present invention can deliver the biologically active substance to target immune cells selected from the group consisting of macrophages, B lymphocytes, T lymphocytes, mast cells, monocytes, dendritic cells, eosinophils, natural killer cells, basophils, and neutrophils such that the biologically active substance acts in the immune cells. Therefore, the fusion product is expected to provide a breakthrough in the development of drug delivery systems.

The cell penetrating peptide allows the fusion product to act with high affinity on macrophages as immune cells so that the biologically active substance can be specifically and efficiently delivered into macrophages.

As mentioned earlier, the biologically active substance refers to a function regulating substance that is bound to the cell penetrating peptide and is delivered into cells where it has a biological activity to regulate all physiological phenomena in vivo. The biologically active substance is meant to include all materials whose enhanced cell penetration efficiency, particularly enhanced specific delivery efficiency to macrophages, is desired. Specifically, the biologically active substance may be selected from the group consisting of proteins, nucleic acids, peptides, lipids, glycolipids, minerals, sugars, nanoparticles, minerals, biological agents, contrast materials, drugs, compounds, and combinations thereof. More specifically, the biologically active substance may be a substance that is not easily transferred into cells via general routes or has low specific delivery efficiency to macrophages even though it is easily transferred into cells.

The biologically active substance may be a peptide or a protein. Such peptides and proteins include, but are not limited to, hormones, hormone analogs, cytokines, signal transduction peptides, vaccines, antibodies, antibody fragments, enzymes, enzyme inhibitors, soluble receptors, signal transduction proteins, transcription factors, coactivators, transcription inhibitory proteins, and mitochondrial proteins. In this case, a DNA expressing the cell penetrating peptide according to the present invention is allowed to bind to a DNA expressing a peptide as the biologically active substance and the DNAs are expressed simultaneously so that the biologically active substance and the cell penetrating peptide can be bound together to form a fusion protein.

The biologically active substance may be a nucleic acid. The nucleic acid may be a naturally occurring or artificial DNA or RNA molecule and may be single- or double-stranded. The biologically active substance may be a combination of one or more nucleic acid molecules. In this case, the nucleic acid molecules may be of the same type (for example, they may have the same nucleotide sequence) or different types. Specific examples of such nucleic acids include, but are not limited to, cDNAs, decoy DNAs, cfDNAs, ctDNAs, RNAs, siRNAs, miRNAs, shRNAs, stRNAs, snoRNAs, snRNAs, PNAs, antisense oligomers, plasmids, and other modified nucleic acids.

The biologically active substance may be a fluorescent material. The fluorescent material may be fluorescein isothiocyanate (FITC) or green fluorescent protein (GFP).

The biologically active substance may be a contrast material. The contrast material is meant to include all materials that are used to image in vivo structures or fluids in medical imaging. Examples of such contrast materials include, but are not limited to, radiopaque contrast materials, paramagnetic contrast materials, superparamagnetic contrast materials, CT contrast materials, and other contrast materials.

The use of the contrast material or fluorescent material is advantageous in that the presence or absence of macrophages in vivo and in vitro can be determined or the locations of macrophages can be efficiently labeled.

The biologically active substance is not particularly limited as long as it has a therapeutic or prophylactic effect on macrophage-mediated diseases. The biologically active substance is preferably an agent that can inhibit inflammasome activity or NF-κB activity, specifically NF-κB signaling or inflammasome signaling.

The inhibition of NF-kB signaling means to inhibit the activation of nuclear factor κ-light-chain-enhancer of activated B cells (NF-κB) in target cells, preferably immune cells, particularly macrophages. Any agent that can inhibit NF-κB activation or transcription may be used without particular limitation. Specifically, the agent inhibiting NF-κB signaling refers to a substance that inhibits or interferes with the NF-κB essential modulator (NEMO), the nuclear localization sequence (NLS) of NF-κB or the function of p65. Such inhibition or interference can be achieved by interfering with the transcription of the NEMO, NLS or p65 gene or inhibiting the mRNA translation of the NEMO, NLS or p65 gene. Alternatively, the agent inhibiting NF-κB signaling may be one that specifically binds to active sites of NEMO, NLS or p65 protein or cause structural modification of the protein to reduce the activity of the protein or inactivate the protein. Examples of substances that reduce or interfere with the activity of NEMO, NLS or p65 include, but are not particularly limited to, compounds, proteins, amino acids, peptides, viruses, sugars, lipids, and nucleic acids.

The inhibition of inflammasome signaling means to decrease or inhibit inflammasome activity in target cells, preferably immune cells, particularly macrophages. Specifically, any agent that can inhibit inflammasome production, cytokine production induced by inflammasomes or adaptor protein apoptosis-associated speck-like protein containing a caspase-recruitment domain (ASC) oligomer formation may be used without particular limitation. Specifically, the agent inhibiting inflammasome signaling may be an agent that inhibits inflammasome activity by suppressing ASC oligomer formation before inflammasome production.

The agent inhibiting inflammasome activity refers to a substance that inhibits or interferes with the function of the ASC gene or ASC protein. Such inhibition or interference can be achieved by interfering with the transcription of the ASC gene or inhibiting the mRNA translation of the ASC gene. Alternatively, the agent inhibiting inflammasome activity may be one that specifically binds to active sites of ASC protein or cause structural modification of the protein to reduce the activity of the protein or inactivate the protein. Examples of substances that reduce or interfere with the expression of the ASC gene or the activity of ASC protein include, but are not particularly limited to, compounds, proteins, amino acids, peptides, viruses, sugars, lipids, and nucleic acids.

The agent may include an antisense oligonucleotide, miRNA, dsRNA, siRNA, or shRNA that complementarily binds to the ASC gene.

The substance inhibiting the expression of the ASC gene may be a substance that inhibits the mRNA translation of the ASC gene. The mRNA translation of the ASC gene can be inhibited using a small molecule compound or RNA, siRNA or shRNA available for antisense nucleic acid sequence preparation or RNAi technique. The expression of the ASC gene can be inhibited using a protein or compound binding to a promoter, enhancer or transcriptional regulator known to regulate the transcription of the ASC gene.

The agent may include an antibody, antibody fragment, peptide or aptamer that specifically binds to the ASC protein. More specifically, the substance inhibiting the activity of the ASC protein may be, for example, selected from the group consisting of antibodies specifically binding to the ASC protein, their fragments having antigen-binding properties, their polypeptides having binding activity, and combinations thereof. The substance may include an aptamer, compound, peptide or peptide mimetic that complementarily binds to the ASC protein.

The substance inhibiting the activity of the ASC protein is more preferably a substance that blocks the interaction between NLRP3 PYD and ASC PYD and may be, for example, an antibody, antibody fragment, peptide or aptamer that specifically binds to the ASC PYD domain.

The biologically active substance is more preferably NLRX1 protein, specifically leucine-rich repeat (LRR) domain derived from NLRX1 protein. The LRR domain has the amino acid sequence set forth in SEQ ID NO: 25.

The NLRX1 protein or its genetic information can be obtained from a known database such as GenBank of the U.S. National Center for Biotechnology Information (NCBI). Specifically, the NLRX1 protein has the sequence set forth in SEQ ID NO: 23. The LRR domain derived from the NLRX1 protein is a fragment of the NLRX1 protein that has the amino acid sequence set forth in SEQ ID NO: 25. More specifically, the LRR domain derived from the NLRX1 protein may have the amino acid sequence set forth in SEQ ID NO: 25 or may have a homology of at least 50% to the sequence while possessing the activity of the sequence. The LRR domain derived from the NLRX1 protein may have a homology of at least 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% to the sequence set forth in SEQ ID NO: 25. However, the LRR domain derived from the NLRX1 protein is not limited to the characteristics described above.

The biologically active substance may be a drug. The drug is not limited to a particular type but is preferably one that is applicable to macrophage-related diseases. Examples of such drugs include non-steroidal anti-inflammatory drugs (NSAIDs) and anticancer drugs. The non-steroidal anti-inflammatory drugs may be selected from the group consisting of aspirin, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, and aceclofenac. The anticancer agents may be selected from the group consisting of cisplatin, vinblastine, vincristine, actinomycin-D, 5-fluouracil, docetaxel, cabazitaxel, paclitaxel, and pembrolizumab.

The biologically active substance may be bound covalently or non-covalently to the N- or C-terminus of the cell penetrating peptide.

The cell penetrating peptide may be indirectly linked to the biologically active substance by a cloning technique using an expression vector at the nucleotide level. Alternatively, the cell penetrating peptide may be directly linked to the biologically active substance by chemical or physical covalent or non-covalent bonding therebetween.

Figure 5A:
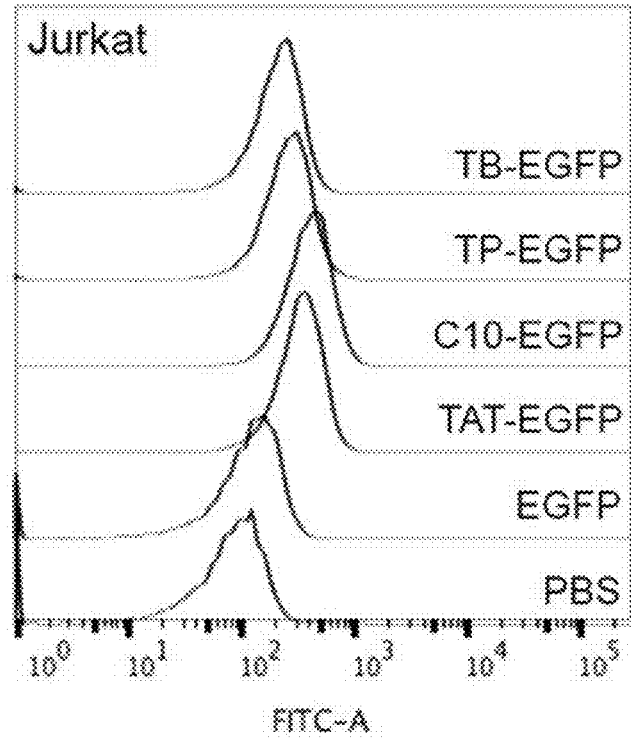
FIGS. 5A and 5B show the results of flow cytometry for Jurkat cells after treatment with C10-EGFP, TP-EGFP, TB-EGFP, and TAT-EGFP and culture for 1 hour.
Figure 5B:
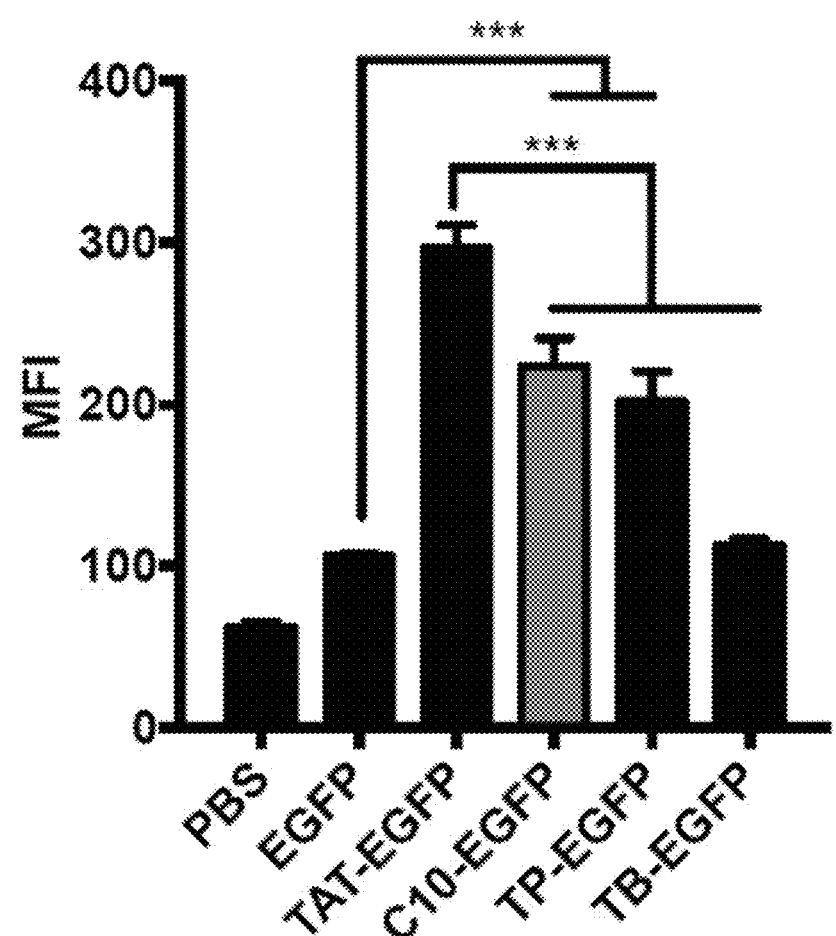

In the Examples section that follows, cell penetrating peptides of various types and lengths were selected by an in silico approach (Experimental Example 1) and enhanced green fluorescent protein (EGFP) was linked to candidate sequences of the selected cell penetrating peptides to prepare recombinant proteins. The recombinant proteins were demonstrated to have significantly improved permeability to specific cells compared to conventional cell penetrating peptides (FIGS. 5A to 5B and 6). The fusion product of the present invention has a high preference for immune cells, particularly macrophages, compared to conventional cell penetrating peptides. In addition, the fusion product of the present invention has greatly improved delivery efficiency to cells compared to conventional cell penetrating peptides.

The newly identified significant cell penetrating effects of the cell penetrating peptide according to the present invention can be explained as follows.

Figure 8:
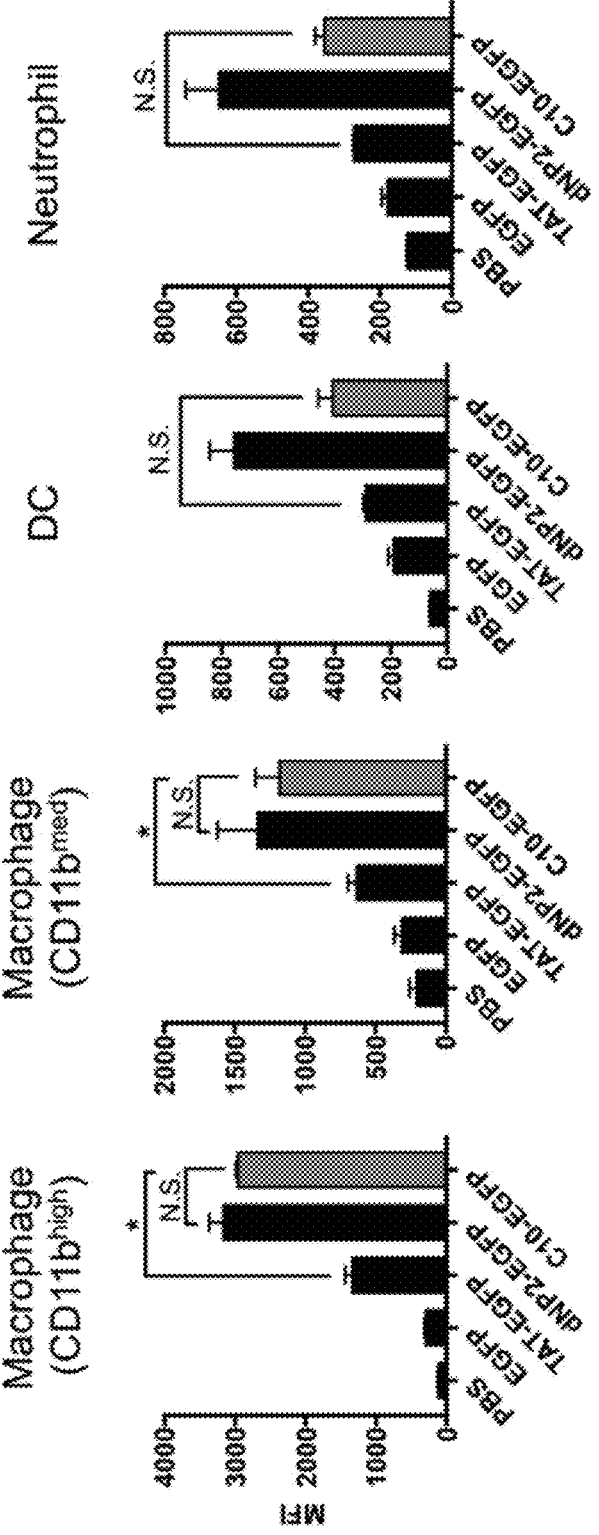
FIG. 8 shows the results of flow cytometry for $CD11b^{high}F4/80^+$ macrophages, $CD11b^{mod}F4/80^+$ macrophages, $MHCII^{high}CD11c^+$ classical dendritic cells (cDCs), and $Ly6G^+$ neutrophils sorted from splenocytes after treatment with recombinant proteins (C10-EGFP, TAT-EGFP, and dNP2-EGFP), EGFP (comparative), and PBS (control)
Figure 9:
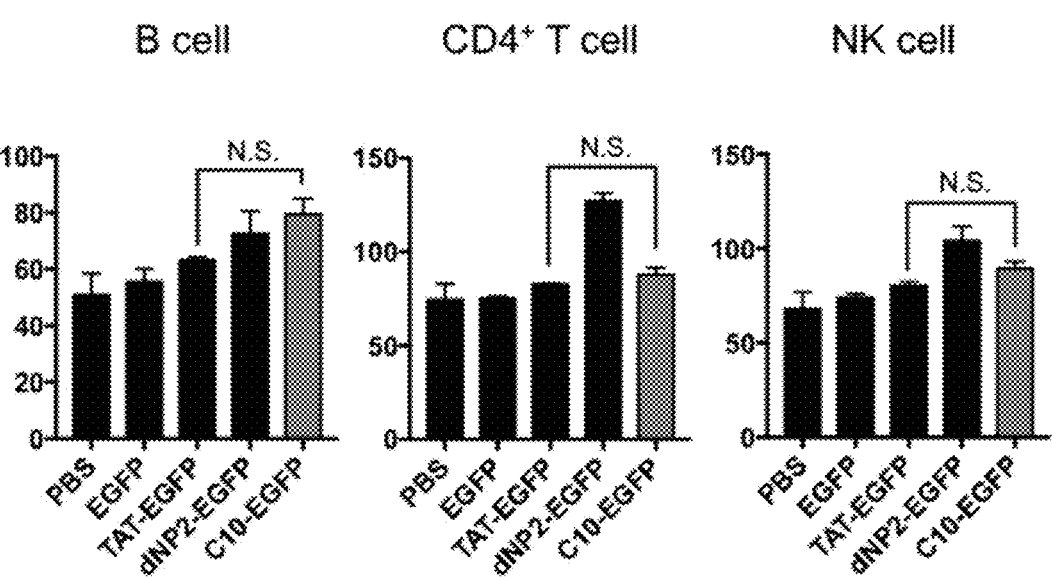
FIG. 9 shows the results of flow cytometry for $CD19^+$ B cells, $CD4^+$ T cells, and $NK1.1^+$ cells as lymphocytes sorted from splenocytes after treatment with recombinant proteins (C10-EGFP, TAT-EGFP, and dNP2-EGFP), EGFP (comparative), and PBS (control)

Since conventional cell penetrating peptides are derived from cell membrane penetrating domains, they exhibit general levels of delivery efficiency to immune cells, including macrophages, as well as general cells such as skin cells. In contrast, the cell penetrating peptide of the present invention enables effective delivery to immune cells, including lymphocytes, as well as myeloid cells such as macrophages, dendritic cells, and neutrophils regardless of in vivo or in vitro space compared to conventional cell penetrating peptides, which was confirmed in the Examples section that follows. Particularly, the cell penetrating peptide of the present invention enables specific delivery to macrophages with significantly higher efficiency than conventional cell penetrating peptides, which was also confirmed in the Examples section that follows (FIGS. 8 and 9). That is, the cell penetrating peptide of the present invention enables specific delivery to cells, particularly macrophages, with high efficiency, unlike conventional cell penetrating peptides.

Figure 12:
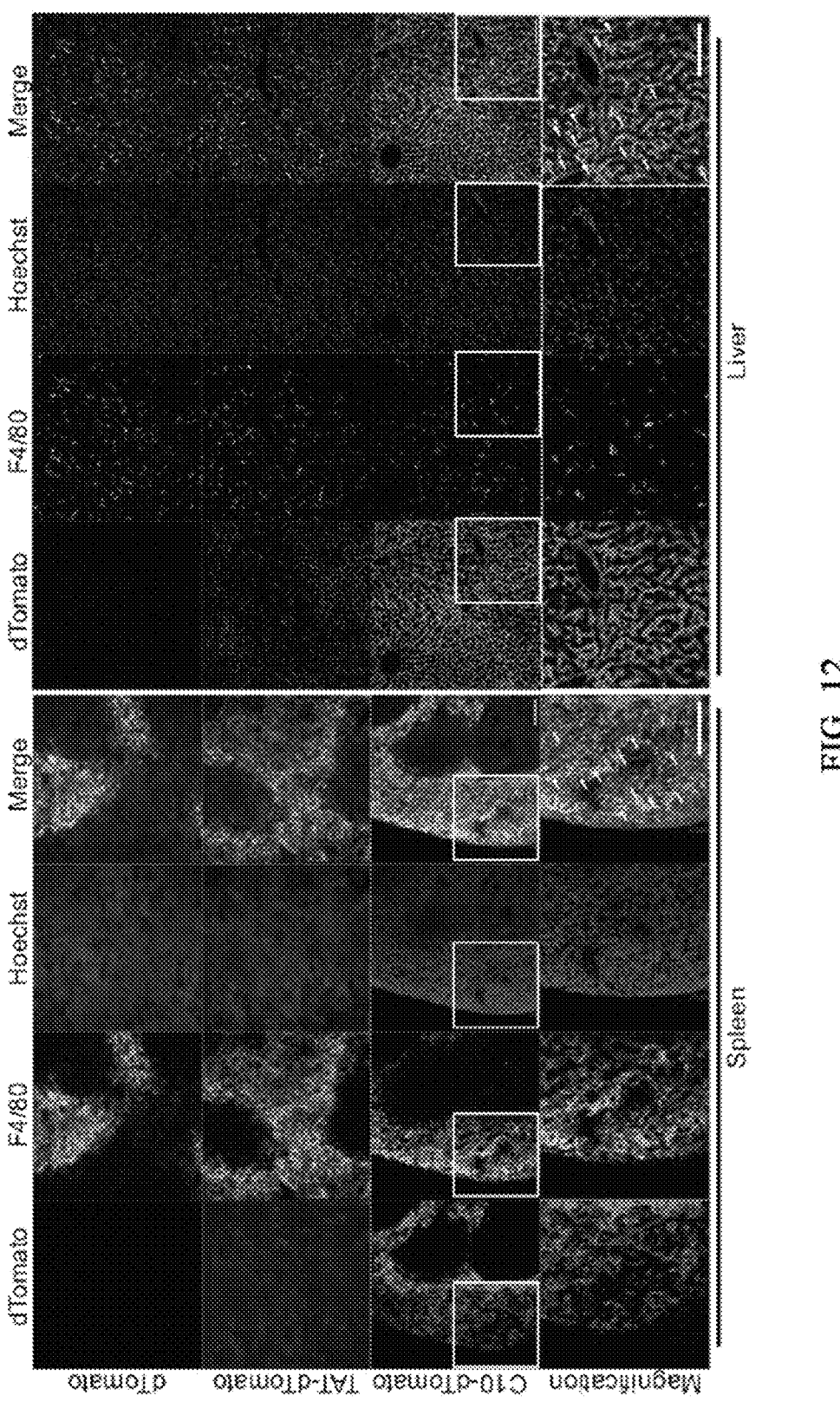
FIG. 12 shows confocal microscopy images of tissues isolated from mice after intraperitoneal injection of C10-dTomato, TAT-dTomato, and dTomato and staining with α-F4/80 antibody 2 hours after the injection.

In the Examples section that follows, the cell penetrating peptide of the present invention was investigated for in vivo distribution, and as a result, its delivery efficiency to macrophages was significantly high, unlike conventional cell penetrating peptides (FIG. 12).

Therefore, the fusion product using the cell penetrating peptide of the present invention and a system for the delivery of a biologically active substance using the fusion product as an active ingredient have greatly improved characteristics in vivo or in clinical conditions (including improved specificities to macrophages and delivery efficiencies to cells) compared to conventional cell penetrating peptides, fusion products thereof or delivery systems using the fusion products.

The present invention also provides a composition for delivering a biologically active substance into cells, the composition including the fusion product of the cell penetrating peptide and the biologically active substance as an active ingredient. The present invention also provides use of the composition for gene therapy. The composition may be for therapeutic or non-therapeutic use.

The composition may further include at least one active ingredient whose function is identical or similar to that of the fusion product. For example, when the biologically active substance of the fusion product is an anti-inflammatory substance, the active ingredient may be any substance that inhibits the function of inflammatory cytokines. Examples of such substances include, but are not particularly limited to, anti-IL-6, IL-1β, and anti-inflammatory antibodies.

The composition may further include one or more pharmaceutically acceptable carriers for administration in addition to the above-described active ingredients. The pharmaceutically acceptable carriers may be selected from the group consisting of saline, sterilized water, Ringer's solution, buffered saline, dextrose solution, maltodextrin solution, glycerol, ethanol, liposomes, and mixtures thereof. The composition may optionally further include other general additives such as antioxidants, buffers, and bacteriostatic agents. Diluents, dispersants, surfactants, binders, and lubricants may be further added to prepare injectable formulations (such as aqueous solutions, suspensions, and emulsions), pills, capsules, granules, and tablets. Antibodies or other ligands specific to a target organ may be bound to the carriers for specific action on the target organ. Furthermore, the composition is preferably formulated according to the type of diseases or the kind of ingredients in accordance with any suitable method known in the art, preferably any of the methods disclosed in Remington's Pharmaceutical Science (the newest edition), Mack Publishing Company, Easton PA.

The composition can be administered via suitable routes for in vivo delivery, for example, intravenous, intraperitoneal, intramuscular, subcutaneous, intradermal, nasal, mucosal, inhalation, and oral routes. The dose of the composition may vary depending on the body weight, age, sex, health and diet of subjects, the time and mode of administration, the rate of excretion, the severity of disease, and other relevant factors. A daily dose of the composition may range from about 0.01 to about 100 mg/kg, preferably 0.5 to 10 mg/kg, and is more preferably administered in a single dose or divided doses.

The present invention also provides a composition for use as a drug adjuvant, the composition including the fusion product as an active ingredient. The composition may be for therapeutic or non-therapeutic use.

As used herein, the term "use as a drug adjuvant" means the use the composition as an adjuvant in combination with a conventional drug to maximize the effect of the drug. When co-administered with a drug, the fusion product of the present invention greatly improves the efficacy of the drug although the medicinal effect of the drug is relatively poor.

The fusion product of the present invention can be used to markedly enhance the therapeutic efficacy of an immunomodulatory drug for sepsis, indicating that the fusion product of the present invention is suitable for practical use as a macrophage-targeting drug adjuvant.

The drug is not limited to a particular type. The function of the drug may be identical or similar to that of the fusion product. For example, when the biologically active substance of the fusion product is an anti-inflammatory substance, the drug may be any substance that inhibits the function of inflammatory cytokines. Examples of such substances include, but are not particularly limited to, anti-IL-6, IL-1β, and anti-inflammatory antibodies. The anti-inflammatory antibodies may be non-steroidal anti-inflammatory drugs (NSAIDs). The non-steroidal anti-inflammatory drugs may be selected from the group consisting of aspirin, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, and aceclofenac.

The biologically active substance of the fusion product may be an anticancer drug. The anticancer drug is not particularly limited as long as it has anticancer activity. The anticancer drug is preferably selected from the group consisting of cisplatin, vinblastine, vincristine, actinomycin-D, 5-fluouracil, docetaxel, cabazitaxel, paclitaxel, pembrolizumab, and mixtures thereof.

The composition may further include one or more pharmaceutically acceptable carriers for administration in addition to the above-described active ingredients. The pharmaceutically acceptable carriers may be selected from the group consisting of saline, sterilized water, Ringer's solution, buffered saline, dextrose solution, maltodextrin solution, glycerol, ethanol, liposomes, and mixtures thereof. The composition may optionally further include other general additives such as antioxidants, buffers, and bacteriostatic agents. Diluents, dispersants, surfactants, binders, and lubricants may be further added to prepare injectable formulations (such as aqueous solutions, suspensions, and emulsions), pills, capsules, granules, and tablets. Antibodies or other ligands specific to a target organ may be bound to the carriers for specific action on the target organ. Furthermore, the composition is preferably formulated according to the type of diseases or the kind of ingredients in accordance with any suitable method known in the art, preferably any of the methods disclosed in Remington's Pharmaceutical Science (the newest edition), Mack Publishing Company, Easton PA.

The composition can be administered via suitable routes for in vivo delivery, for example, intravenous, intraperitoneal, intramuscular, subcutaneous, intradermal, nasal, mucosal, inhalation, and oral routes.

The composition of the present invention can be administered in such an amount that its medicinal effect is exerted when administered alone or in combination with one more other drugs. A suitable total daily dose can be determined according to a physician's correct medical judgment. A therapeutically effective amount of the composition administered to a patient may vary depending on various factors, including the type and extent of the desired response, the type and amount of the concomitant drug, the specific amount of other optional agents, the age, body weight, health, sex, and diet of the patient, the time and route of administration, the treatment period, and the radiation dose, and similar factors well known in the pharmaceutical field.

The present invention also provides a recombinant expression vector expressing a recombinant protein in which the cell penetrating peptide is fused to a biologically active substance. The present invention also provides a recombinant expression vector including a DNA encoding the cell penetrating peptide and a DNA encoding a biologically active protein.

The biologically active protein may be a protein that is delivered intracellularly or in vivo to exhibit an activity related to a physiological phenomenon or an activity related to a therapeutic purpose.

The recombinant expression vector may include the sequences of the cell penetrating peptide and the biologically active protein and tag sequences facilitating purification of the fusion protein, for example, consecutive histidine codons, maltose binding protein codons, and Myc codons, and may optionally further include a fusion partner to enhance the solubility of the fusion product. The recombinant expression vector may further include spacer amino acid or polynucleotide sequences for the overall structural and functional stabilization of the recombinant protein or the flexibility of proteins encoded by respective genes. Examples of the spacers include, but are not limited to, AAY (P. M. Daftarian et al., J Trans Med 2007, 5:26), AAA, NKRK (R. P. M. Sutmuller et al., J Immunol. 2000, 165: 7308-7315), and one or more lysine residues (S. Ota et al., Can Res. 62, 1471-1476, K. S. Kawamura et al., J Immunol. 2002, 168: 5709-5715).

The recombinant expression vector may include a sequence specifically cleaved by an enzyme to remove an unnecessary portion of the recombinant protein, an expression regulatory sequence, and a marker or reporter gene sequence to confirm intracellular delivery but is not limited thereto.

The expression regulatory sequence used in the recombinant expression vector may be composed of a regulatory domain including a promoter specific to a cell, tissue or organ where target DNA and/or RNA is selectively delivered or expressed.

The present invention also provides a method for delivering a biologically active substance, the method including binding the cell penetrating peptide to the biologically active substance to prepare a delivery complex and injecting the delivery complex in vivo or intracellularly.

The cell penetrating peptide may be indirectly bound to the biologically active substance by a cloning technique using an expression vector at the nucleotide level. Alternatively, the cell penetrating peptide may be directly bound to the biologically active substance by chemical or physical covalent or non-covalent bonding therebetween. The in vivo or intracellular injection of the delivery complex can be performed by administration via suitable routes, for example, intravenous, intraperitoneal, intramuscular, subcutaneous, intradermal, nasal, mucosal, inhalation, and oral routes. The method can be sufficiently extended to the delivery to culture cells as well as general in vivo delivery, that is, delivery to cells, tissues, and bodies of animals.

The present invention also provides a method for gene therapy, the method including binding the cell penetrating peptide to a genetic material to prepare a delivery complex and injecting the delivery complex into cells.

The cell penetrating peptide can be directly bound to the genetic material by chemical or physical covalent or non-covalent bonding therebetween. The in vivo or intracellular injection of the delivery complex of the genetic material can be performed by administration via the same routes as described above. The method can be sufficiently extended to the delivery to culture cells as well as general in vivo delivery, that is, delivery to cells, tissues, and bodies of animals.

The delivery complex of the genetic material is nonimmunogenic and noninfectious and is not limited by the size of plasmids because the DNA is not packaged in a vector organism such as retrovirus or adenovirus. Therefore, the delivery complex can be used in recombinant gene expression constructs of any practical size.

The present invention will be more specifically explained with reference to the following examples. However, it will be obvious to those skilled in the art that these examples are provided for illustrative purposes only and are not intended to limit the scope of the invention.

Example 1. Production of C10-EGFP Recombinant Protein

Generation of Polynucleotide Sequence Encoding C10-EGFP Recombinant Protein

C10-EGFP recombinant protein was produced by the following procedure. First, a forward primer of SEQ ID NO: 29 (Bionics) was synthesized in which (1) a NheI restriction enzyme recognition site, (2) the polynucleotide sequence set forth in SEQ ID NO: 2 encoding the C10 polypeptide (SEQ ID NO: 1), (3) a BamHI restriction enzyme recognition site, and (4) a polynucleotide sequence encoding a portion of the N-terminus of EGFP were sequentially arranged in the 5' to 3' direction. A reverse primer of SEQ ID NO: 30 (Bionics) was synthesized in which (1) a HindIII restriction enzyme recognition site and (2) a polynucleotide sequence encoding a portion of the C-terminus of EGFP were sequentially arranged in the 5' to 3' direction. In the forward primer of SEQ ID NO: 29, the NheI restriction enzyme recognition site (1) is for DNA cloning and the BamHI restriction enzyme recognition site (3) is to connect the polynucleotide sequence (SEQ ID NO: 2) (2) and the polynucleotide sequence encoding a portion of the N-terminus of EGFP (4). In the reverse primer of SEQ ID NO: 30, the HindIII restriction enzyme recognition site (1) is for DNA cloning.

PCR was performed using pRSET-b vector containing the EGFP gene as a template and the primer pair (SEQ ID NOS: 29 and 30) to generate the polynucleotide sequence of SEQ ID NO: 31 encoding a fusion protein of the C10 polypeptide derived from human IL-10 and EGFP. The PCR was repeated 35 cycles in a PCR reactor (Biorad). Each cycle consisted of initial thermal denaturation at 95° C. for 3 min, thermal denaturation of the template at 95° C. for 20 sec, binding of the primers and the template at 50° C. for 20 sec, and extension at 72° C. for 30 sec.

Construction of Recombinant Expression Vector

In order to express the C10-EGFP fusion protein, the gene (DNA) fragment prepared above was digested with restriction enzymes and inserted into the protein expression vector pRSETb using ligase. The amplified DNA fragment was allowed to react with NheI and HindIII (NEB) to make the 5'/3' ends of the DNA sticky. pRSETb was allowed to react with the same two restriction enzymes to construct a linear pRSETb vector having NheI and HindIII insertion sites. After each enzymatic reaction, the product was isolated using a PCR purification kit (Cosmogene Tech).

The isolated C10-EGFP fusion protein double-stranded DNA fragment and pRSET-b vector were allowed to react with T4 ligase (NEB) for ligation at 25° C. for 2 h.

The resulting C10-EGFP-inserted circular pRSETb vector was transformed into E. coli strain DH5a and cultured in an LB plate medium supplemented with 50 μg/ml ampicillin as an antibiotic. Colony-forming transformed E. coli cells were selected. The selected E. coli colonies were inoculated into and cultured in a liquid LB medium supplemented with 50 μg/ml ampicillin. Then, the plasmid vector was separated using a plasmid mini preparation kit (Cosmogene Tech).

PCR was performed using the recombinant C10-EGFP-_pRSET-b vector as a template and the primer pair (SEQ ID NOS: 29 and 30) to generate a polynucleotide sequence encoding a fusion protein of the C10 polypeptide derived from human IL-10 and EGFP. DNA sequencing of the polynucleotide was requested to Cosmogene Tech to determine whether the vector was constructed accurately.

Isolation and Purification of Recombinant Protein

A 6-His-tagged recombinant protein was expressed from the obtained E. coli. To this end, each colony was inoculated into an LB liquid medium supplemented with 50 μg/ml ampicillin and cultured at 37° C. for 10 h. The culture was transferred to a fresh 500 ml LB liquid medium and IPTG was added until a concentration of 0.2 mM was reached. The temperature was lowered to 20° C. and further culture was performed at 150 rpm for 14 h. After completion of the culture, the culture medium was collected.

Ni-NTA affinity chromatography was used to isolate and purify a 6-His-tagged recombinant protein expressed from the E. coli. The E. coli culture medium was centrifuged to obtain pellets. The pellets were treated with a lysis buffer (50 mM $NaH_2PO_4$, 300 mM NaCl, 10 mM imidazole, pH 8.0) and the cell walls were disrupted by sonication. The cell lysate was centrifuged. The resulting supernatant was collected and cultured on Ni-NTA agarose (Qiagen) beads.

The recombinant protein-bound beads were washed with a wash buffer (50 mM $NaH_2PO_4$, 300 mM NaCl, 20 mM imidazole, pH 8.0) and treated with an eluent buffer (50 mM $NaH_2PO_4$, 300 mM NaCl, 250 mM imidazole, pH 8.0). The recovered solution was desalted on a PD-10 SEPHADEX® G-25 column (GE Healthcare). To evaluate microbial endotoxin contamination of the recombinant protein after purification, the desalted recombinant protein was incubated in 1% Triton X-114 at 4° C. for 30 min. Aggregates were separated from the solution by centrifugation. This procedure was repeated 4 times. Then, desalting was performed on a PD-10 SEPHADEX® G-25 column (GE Healthcare). The protein concentration was quantitatively measured by Bradford assay. The purified protein was stored in a HBSS solution containing 10% glycerol at 80° C. prior to starting experiments.

Example 2. Production of C10-LRR Recombinant Protein

C10-LRR recombinant protein was produced in the same manner as in Example 1, except that the polynucleotide sequence of SEQ ID NO: 34 encoding a fusion protein of C10 polypeptide derived from human IL-10 and LRR was generated using a forward primer of SEQ ID NO: 32 including the polynucleotide sequence of SEQ ID NO: 26 encoding an NRR domain (903 bp) (SEQ ID NO: 25) with depletion of 2022 bp at the N-terminus of NLRX1 protein in the 5' to 3' direction and a reverse primer of SEQ ID NO: 33 instead of the forward primer of SEQ ID NO: 29 and the reverse primer of SEQ ID NO: 30, respectively. The recombinant protein was identified by 12% SDS-PAGE.

Example 3. Production of C10-NBD Recombinant Protein

C10-NBD recombinant protein was produced in the same manner as in Example 1, except that the polynucleotide sequence of SEQ ID NO: 37 encoding a fusion protein of C10 polypeptide derived from human IL-10 and LBD was generated using a forward primer of SEQ ID NO: 35 including the polynucleotide sequence of SEQ ID NO: 28 encoding a NACHT domain (SEQ ID NO: 27) with depletion of some base pairs at the C-terminus of NLRX1 protein in the 5' to 3' direction and a reverse primer of SEQ ID NO: 36 instead of the forward primer of SEQ ID NO: 29 and the reverse primer of SEQ ID NO: 30, respectively. The recombinant protein was identified by 12% SDS-PAGE.

Example 4. Production of C10-dTomato Recombinant Protein

C10-dTomato recombinant protein was produced in the same manner as in Example 1, except that the polynucleotide sequence of SEQ ID NO: 40 encoding a fusion protein of C10 polypeptide derived from human IL-10 and dTomato was generated using a forward primer of SEQ ID NO: 38 including dTomato and a reverse primer of SEQ ID NO: 39 instead of the forward primer of SEQ ID NO: 29 and the reverse primer of SEQ ID NO: 30, respectively. The recombinant protein was identified by 12% SDS-PAGE.

Examples 5 to 10. Production of Recombinant Proteins of C10 Variants and EGFP Various variants for comparative analysis were generated to investigate the roles of the amino acids constituting C10.

First, cysteine (C), leucine (L), and arginine (R) constituting C10 were substituted or deleted to generate variants having the amino acid sequences set forth in SEQ ID NOS: 3, 5, 7, 9, 11, and 13. The variants were compared with EGFP, C10-EGFP, and TAT-EGFP as controls. Specific experiments were conducted in Experimental Examples 3-5. The results can be seen from FIGS. 5-10.

Recombinant proteins of the variants and EGFP were produced in the same manner as in Example 1, except that the polynucleotide sequences set forth in SEQ ID NOS: 43, 46, 49, 52, 55, and 58 were generated using forward primers of SEQ ID NOS: 41, 44, 47, 50, 53, and 56 and reverse primers of SEQ ID NOS: 42, 45, 48, 51, 54, and 57, respectively. The forward primers of SEQ ID NOS: 41, 44, 47, 50, 53, and 56 were synthesized using the polynucleotide sequences set forth in SEQ ID NOS: 4, 6, 8, 10, 12, and 14 encoding the variants (SEQ ID NOS: 3, 5, 7, 9, 11, and 13) instead of (2), respectively. The recombinant proteins were identified by 12% SDS-PAGE.

Comparative Example 1. Production of TP-EGFP Recombinant Protein

TP-EGFP recombinant protein was produced in the same manner as in Example 1, except that the polynucleotide sequence set forth in SEQ ID NO: 61 was generated using a forward primer of SEQ ID NO: 59 and a reverse primer of SEQ ID NO: 60. The forward primer of SEQ ID NO: 59 was synthesized using the polynucleotide sequence set forth in SEQ ID NO: 16 encoding TP polypeptide (SEQ ID NO: 15) instead of (2). The recombinant protein was identified by 12% SDS-PAGE.

Comparative Example 2. Production of TB-EGFP Recombinant Protein

TB-EGFP recombinant protein was produced in the same manner as in Example 1, except that the polynucleotide sequence set forth in SEQ ID NO: 64 was generated using a forward primer of SEQ ID NO: 62 and a reverse primer of SEQ ID NO: 63. The forward primer of SEQ ID NO: 62 was synthesized using the polynucleotide sequence set forth in SEQ ID NO: 18 encoding TB polypeptide (SEQ ID NO: 17) instead of (2). The recombinant protein was identified by 12% SDS-PAGE.

Comparative Example 3. Production of TAT-EGFP Recombinant Protein

TAT-EGFP recombinant protein was produced in the same manner as in Example 1, except that the polynucleotide sequence set forth in SEQ ID NO: 67 was generated using a forward primer of SEQ ID NO: 65 and a reverse primer of SEQ ID NO: 66. The forward primer of SEQ ID NO: 65 was synthesized using the polynucleotide sequence set forth in SEQ ID NO: 20 encoding TAT polypeptide (SEQ ID NO: 19) instead of (2). The recombinant protein was identified by 12% SDS-PAGE.

Comparative Example 4. Production of TAT-dTomato Recombinant Protein

TAT-dTomato recombinant protein was produced in the same manner as in Example 3, except that the polynucleotide sequence set forth in SEQ ID NO: 70 was generated using a forward primer of SEQ ID NO: 68 including dTomato and a reverse primer of SEQ ID NO: 69 instead of the forward primer of SEQ ID NO: 65 and the reverse primer of SEQ ID NO: 66, respectively. The recombinant protein was identified by 12% SDS-PAGE.

Comparative Example 5. Production of dNP2-EGFP Recombinant Protein dNP2-EGFP recombinant protein was produced in the same manner as in Example 1, except that the polynucleotide sequence set forth in SEQ ID NO: 73 was generated using a forward primer of SEQ ID NO: 71 and a reverse primer of SEQ ID NO: 72. The forward primer of SEQ ID NO: 71 was synthesized using the polynucleotide sequence set forth in SEQ ID NO: 22 encoding dNP2 polypeptide (SEQ ID NO: 21) instead of (2). The recombinant protein was identified by 12% SDS-PAGE.

Comparative Example 6. Production of TAT-LRR Recombinant Protein

TAT-LRR recombinant protein was produced in the same manner as in Example 1, except that the polynucleotide sequence of SEQ ID NO: 76 encoding a fusion protein of TAT polypeptide and LRR was generated using a forward primer of SEQ ID NO: 74 including the polynucleotide sequence of SEQ ID NO: 26 encoding an NRR domain (903 bp) (SEQ ID NO: 25) with depletion of 2022 bp at the N-terminus of NLRX1 protein in the 5' to 3' direction and a reverse primer of SEQ ID NO: 75 instead of the forward primer of SEQ ID NO: 29 and the reverse primer of SEQ ID NO: 30, respectively. The recombinant protein was identified by 12% SDS-PAGE.

Experimental Example 1. Screening of CPP candidate sequences Cell penetrating peptides (CPPs) of human origin were discovered by amino acid sequencing of various human cytokines. To this end, all sequences were filtered using support vector machine (SVM) scores and arginine, lysine or leucine proportions. The SVM scores were analyzed using CellPPD (available online: webs.iiitd.edu.in/raghava/cellppd/), an in silico CPP prediction tool.

As a result of the screening, 10,000 sequences were obtained from 47 human cytokines. 47 sequences with the highest SVM scores were primarily selected from each cytokine by comparison of the SVM scores. Out of the 47 primarily selected sequences, 27 sequences with an SVM score of ≥0.6 and an R, K or L proportion of 60% or an R or K proportion of 50% were secondarily selected. Finally, out of the 27 sequences, 3 candidate sequences with an SVM score of ≥0.6, an R, K or L proportion of 80%, and an R or K proportion of 50% were tertiarily selected. The CPP candidate sequences were IL-10-derived C10 (SEQ ID NO: 1), TSLP-derived TP (SEQ ID NO: 15), and TGFβ-derived TB (SEQ ID NO: 17).

Figures 2, 3:
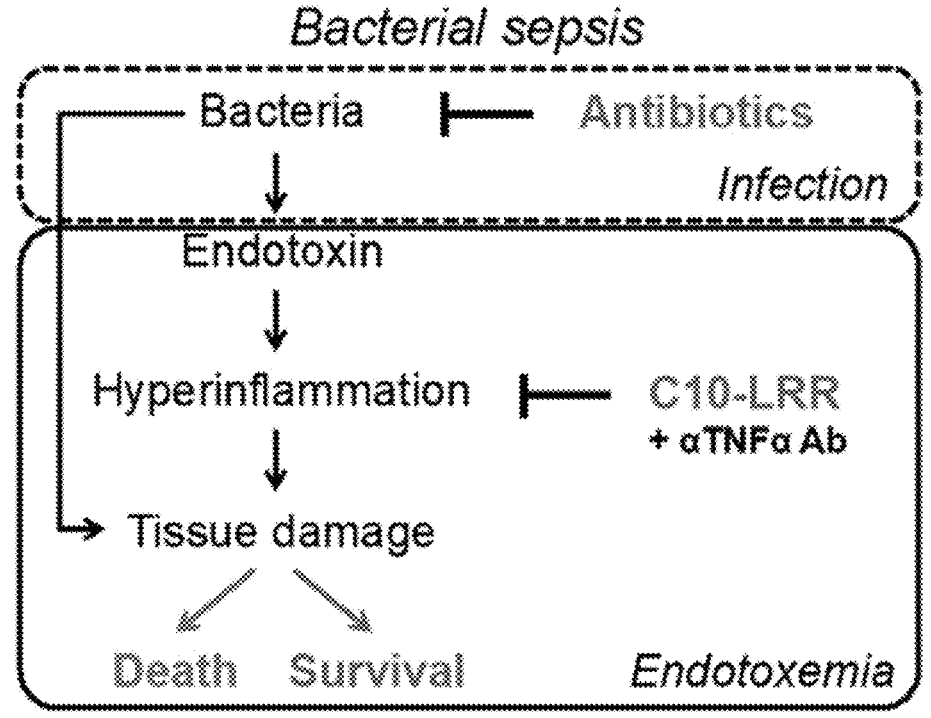
FIG. 3 shows designed DNA structures of C10-EGFP, TP-EGFP, TB-EGFP, and TAT-EGFP.

Experimental Example 2. Isolation and Purification of Recombinant Proteins of the CPP Candidate Sequences Selected by Screening DNAs encoding the three CPP candidate sequences selected by screening in Experimental Example 1 and having 6×His tag and green fluorescent protein (EGFP) were designed (C10-EGFP, TP-EGFP, TB-EGFP, and TAT-EGFP). FIG. 3 shows the designed DNA structures of C10-EGFP, TP-EGFP, TB-EGFP, and TAT-EGFP. Recombinant proteins were isolated and purified using the designed DNAs in according to Example 1 and Comparative Examples 1, 2, and 3.

Figure 4:
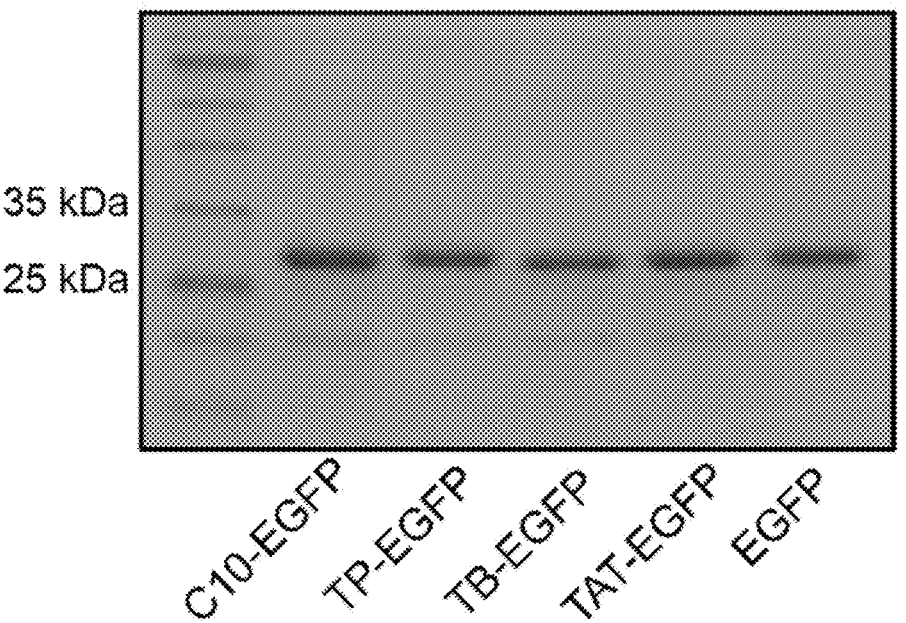
FIG. 4 shows the results of SDS-PAGE for recombinant proteins (C10-EGFP, TP-EGFP, TB-EGFP, and TAT-EGFP) produced in Example 1 and Comparative Examples 1, 2, and 3 and EGFP.

FIG. 4 shows the results of SDS-PAGE for the recombinant proteins (C10-EGFP, TP-EGFP, TB-EGFP, and TAT-EGFP) produced in Example 1 and Comparative Examples 1, 2, and 3 and EGFP. The SDS-PAGE revealed that all recombinant proteins were effectively produced and purified and each had a size of 25-35 kDa.

Experimental Example 3. Analysis of Cell Penetration Efficiency of C10-EGFP, TP-EGFP, TB-EGFP and TAT-EGFP Cell Lines and Culture HeLa and Jurkat cells were purchased from ATCC and stored in DMEM or RPMI (Corning) media. Culture media supplemented with 10% fetal bovine serum and 1% penicillin/streptomycin were used. Cells were cultured in a 5% $CO_2$ incubator at 37° C.

Flow Cytometry

Jurkat or HeLa cells were seeded into 96-well or 12-well plates at a density of $2 \times 10^5$ cells/well. The recombinant proteins (C10-EGFP, TP-EGFP, TB-EGFP, and TAT-EGFP) (each 5 µM) were added to the wells and cultured in a 5% $CO_2$ incubator at 37° C. for 1 h. Thereafter, cells were harvested by centrifugation and washed twice with PBS buffer. The washed cells were treated with trypsin at 37° C.

for 10 min to eliminate proteins attached to the cell membrane. Next, DMEM culture media supplemented with 10% FBS were added to the cells to neutralize the trypsin. Cells were harvested, washed with PBS, and subjected to flow cytometry (FACS Canto II, BD Bioscience). Data were analyzed using FLOWJO™ software (Tree Star).

Statistics

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

Figure 6A:
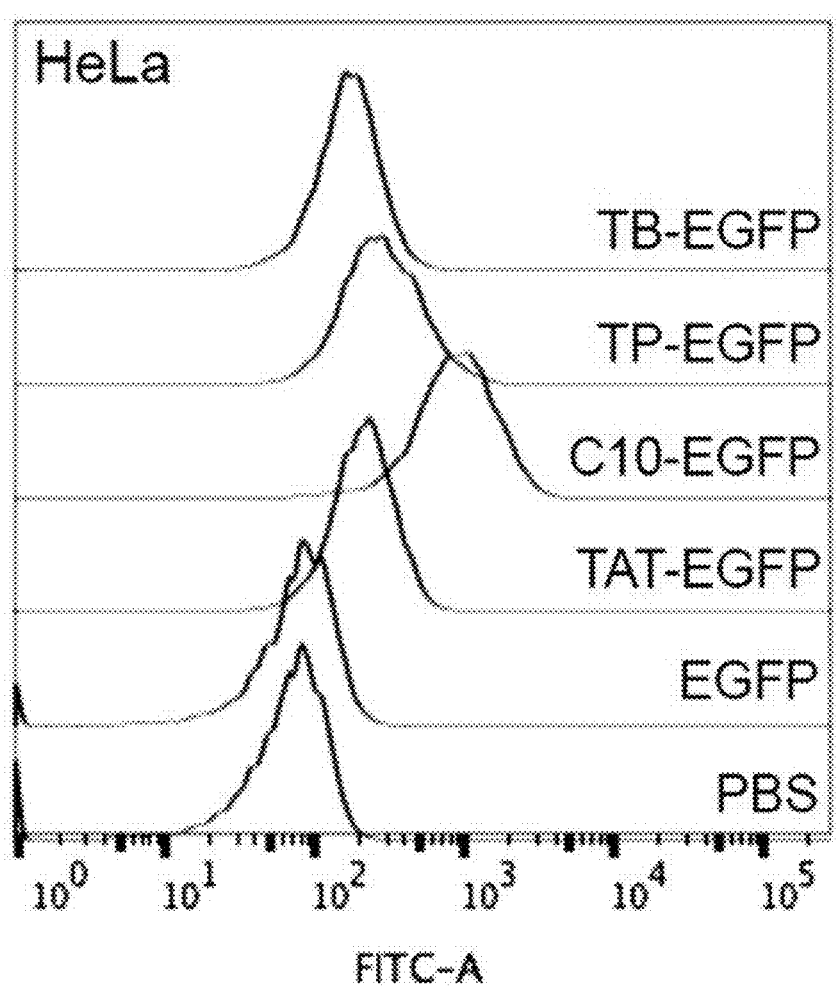
FIGS. 6A and 6B show the results of flow cytometry for Hela cells after treatment with C10-EGFP, TP-EGFP, TB-EGFP, and TAT-EGFP and culture for 1 hour.
Figure 6B:
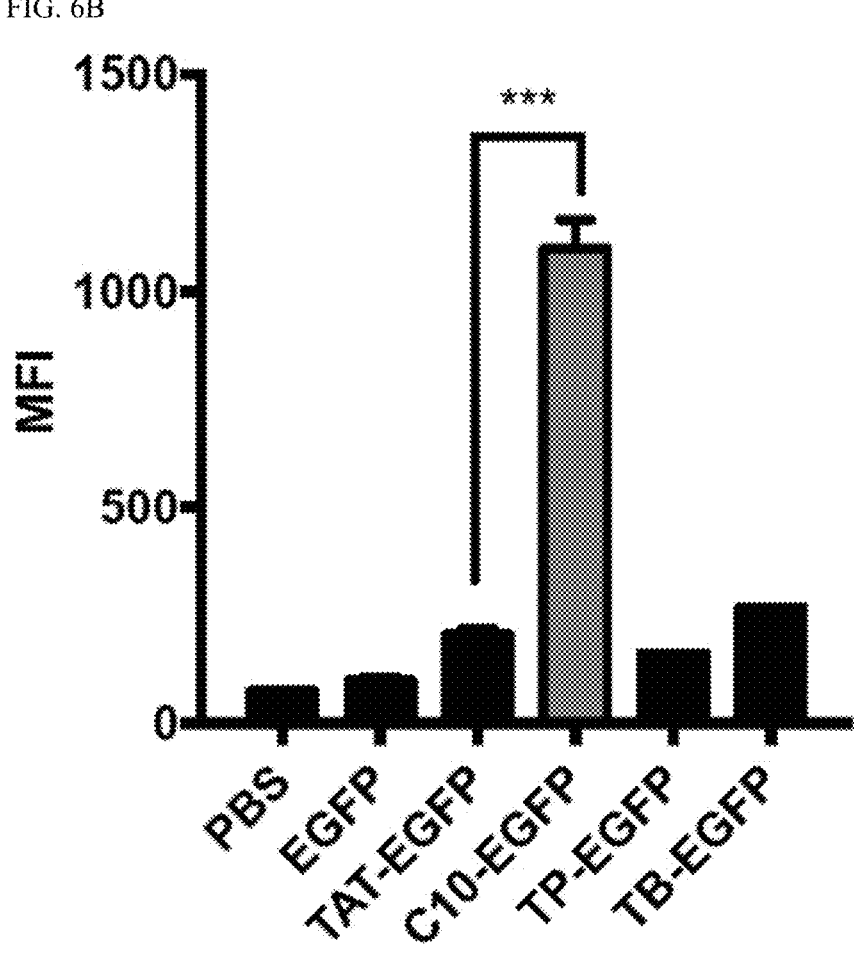

FIGS. 5A and 5B show the results of flow cytometry for the Jurkat cells after treatment with C10-EGFP, TP-EGFP, TB-EGFP, and TAT-EGFP and culture for 1 h and FIGS. 6A and 6B show the results of flow cytometry for the Hela cells after treatment with C10-EGFP, TP-EGFP, TB-EGFP, and TAT-EGFP and culture for 1 h.

As shown in FIGS. 5A to 5B and 6, cell penetration efficiencies were determined based on intracellular fluorescence intensities. Cells treated with the C10-EGFP and TP-EGFP recombinant proteins were found to have significantly higher cell penetration efficiencies than cells treated with PBS, TB-EGFP, and EGFP. For Junkat cells, the cell penetration efficiency of TAT-EGFP was significantly higher than that of the C10-EGFP recombinant protein. However, for Hela cells, the cell penetration efficiency of the C10-EGFP recombinant protein was significantly higher than that of the TAT-EGFP.

In conclusion, the inventive C10 cell penetrating peptide has a remarkably high preference for Hela cells. Based on this conclusion, the C10 cell penetrating peptide was finally selected.

Figure 7:
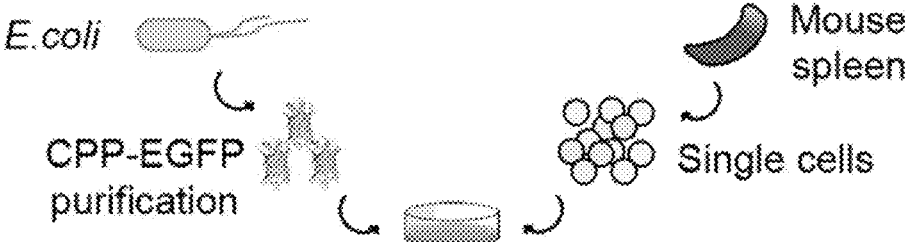
FIG. 7 schematically shows an experimental procedure for analyzing the cell preference of a cell penetrating peptide (C10) by treating mouse splenocytes with a recombinant protein and determining the delivery of the proteins to the splenocytes.

Experimental Example 4. Analysis of Cell Preference of the C10 Cell Penetrating Peptide The following experiment was conducted to analyze the cell preference of the C10 cell penetrating peptide (FIG. 7).

7- to 8-week-old male or female C57BL/6 mice were housed and bred in a specific pathogen-free animal facility at Hanyang University. The mice were acclimatized for two weeks before the experiment. The mice were housed in the facility maintained at a temperature of 21±2° C. and a humidity of 40-60% on a 12-h light/dark cycle and were given water and food ad libitum over the entire experimental period. All animal experiments were conducted in accordance with the Animal Care and Use Protocol approved by the Institutional Animal Care and Use Committee of Hanyang University. Spleen tissues were excised from the mice and splenocytes were isolated as single cells from the tissues by filtration through a 40 µm cell strainer (SPL).

The mouse splenocytes were seeded into 24-well plates at a density of $1 \times 10^6$ cells/well, treated with the recombinant proteins (C10-EGFP, TAT-EGFP, and dNP2-EGFP), EGFP (comparative), and PBS (control) (5 µM), and cultured for 1 h. Cells were harvested, washed with PBS, and stained with α-CD11c, MHCII, CD11b, F4/80, CD4, NK1.1 or CD19 (Biolegend, 1:1000 diluted). Intracellular fluorescence was analyzed by flow cytometry (FACS Canto II, BD Bioscience). Data were analyzed using FLOWJO™ software (Tree Star).

Statistics

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

FIG. 7 schematically shows an experimental procedure for analyzing the cell preference of the C10 cell penetrating peptide for cells by treating the mouse splenocytes with the recombinant proteins and determining the delivery of the proteins to the splenocytes.

FIG. 8 shows the results of flow cytometry for $CD11b^{high}F4/80^+$ macrophages, $CD11^{mod}F4/80^+$ macrophages, $MHCII^{high}CD11c^+$ classical dendritic cells (cDCs), and $Ly6G^+$ neutrophils sorted from splenocytes after treatment with the recombinant proteins (C10-EGFP, TAT-EGFP, and dNP2-EGFP), EGFP (comparative), and PBS (control).

As shown in FIGS. 7 and 8, the dNP2 cell penetrating peptide had overall delivery efficiencies to all immune cells while the inventive C10 cell penetrating peptide had a significant effect only on macrophages. The inventive C10 cell penetrating peptide was found to exhibit a specific delivery effect on macrophages, unlike the dNP2 cell penetrating peptide. This in vivo macrophage-specific function is very useful for treating diseases based on in vivo macrophage function. For diseases such as acute sepsis caused by problems associated with macrophage function, it is important to regulate inflammatory cytokines in macrophages. A drug delivered in vivo to irrelevant cells such as T cells may cause unexpected side effects. That is, for macrophage-associated diseases, the dNP2 cell penetrating peptide is delivered to all immune cells, increasing the risk of unexpected side effects, and the TAT cell penetrating peptide fails to obtain sufficient efficacy due to its low delivery efficiency to all immune cells. In contrast, the inventive C10 cell penetrating peptide can exhibit high efficacy due to its high delivery efficiency specific to macrophages even when treated with a lower concentration of a drug compared to the dNP2 cell penetrating peptide and can prevent, block, suppress, reduce or minimize side effects on other immune cells.

FIG. 9 shows the results of flow cytometry for $CD19^+$ B cells, $CD4^+$ T cells, and $NK1.1^+$ cells as lymphocytes sorted from splenocytes after treatment with the recombinant proteins (C10-EGFP, TAT-EGFP, and dNP2-EGFP), EGFP (comparative), and PBS (control).

As shown in FIGS. 8 and 9, the C10 cell penetrating peptide showed superior delivery efficiency to all types of lymphocytes as well as myeloid cells such as macrophages, dendritic cells, and neutrophils compared to the TAT cell penetrating peptide. The C10 cell penetrating peptide showed the highest delivery efficiency to macrophages and had lower delivery efficiencies to lymphocytes, dendritic cells, and neutrophils than to macrophages. In conclusion, the inventive C10 cell penetrating peptide has a higher preference for macrophages than other cells.

The C10 cell penetrating peptide also showed a delivery efficiency comparable to that of the dNP2 cell penetrating peptide, which is known to have high delivery efficiency to macrophages.

Experimental Example 5. Comparison of Delivery Efficiencies of the Recombinant Proteins in Macrophages The accurate intracellular delivery efficiency of the C10 cell penetrating peptide was compared with those of dNP2 and TAT. To this end, the intracellular delivery efficiencies in macrophages compared to dendritic cells were analyzed based on the results of Experimental Example 3. The results of the analysis are shown in FIGS. 10A to 10c.

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. Error bars indicate S.D.

Figure 10A:
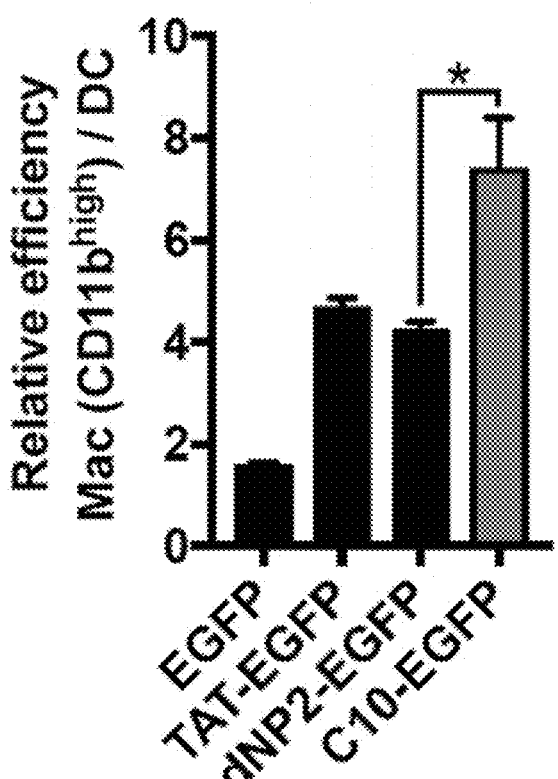
FIGS. 10A to 10C shows delivery efficiencies in $CD11b^{high}$ macrophages compared to dendritic cells (FIG. 10A), delivery efficiencies in $CD11b^{med}$ macrophages compared to dendritic cells (FIG. 10B), and delivery efficiencies in neutrophils compared to dendritic cells (FIG. 10C)
Figure 10B:
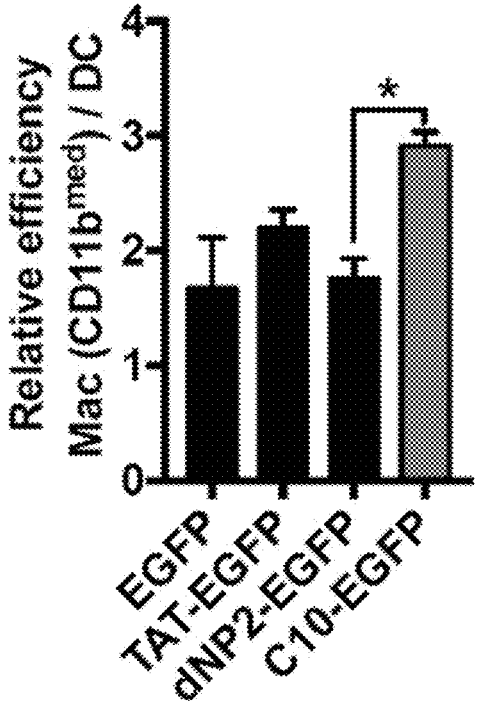
Figure 10C:
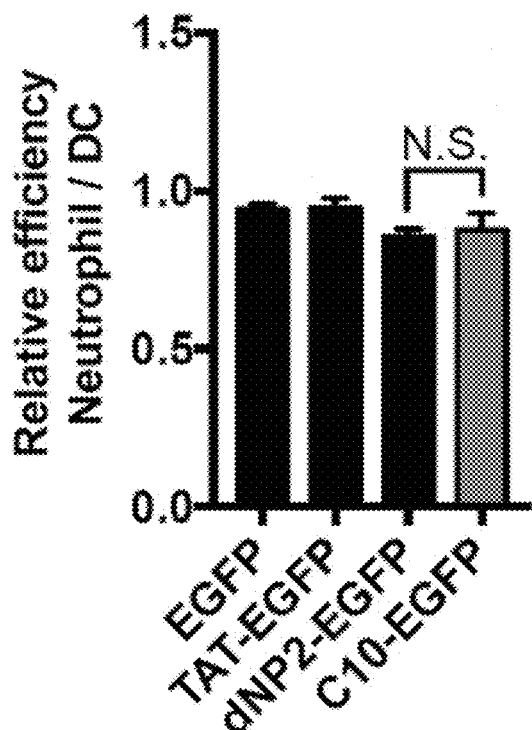

FIGS. 10A to 10C show delivery efficiencies in $CD11b^{high}$ macrophages compared to dendritic cells (FIG. 10A), delivery efficiencies in $CD11b^{med}$ macrophages compared to dendritic cells (FIG. 10B), and delivery efficiencies in neutrophils compared to dendritic cells (FIG. 10C).

As shown in FIGS. 10A to 10C, the delivery efficiencies of the C10 cell penetrating peptide in macrophages were significantly high compared to those of dNP2 and TAT. However, the delivery efficiency of the C10 cell penetrating peptide in neutrophils was not significantly different from those of dNP2 and TAT.

These results indicate that the inventive C10 cell penetrating peptide has a preference for macrophages, unlike the conventional cell penetrating peptides.

Experimental Example 6. In Vivo Distribution of the C10 Cell Penetrating Peptide Experimental Animals 7- to 8-week-old male or female C57BL/6 mice were housed and bred in a specific pathogen-free animal facility at Hanyang University. The mice were acclimatized for two weeks before the experiment. The mice were housed in the facility maintained at a temperature of $21\pm2°$ C. and a humidity of 40-60% on a 12-h light/dark cycle and were given water and food ad libitum over the entire experimental period. All animal experiments were conducted in accordance with the Animal Care and Use Protocol approved by the Institutional Animal Care and Use Committee of Hanyang University.

Sample Administration and Sampling

Figure 11:
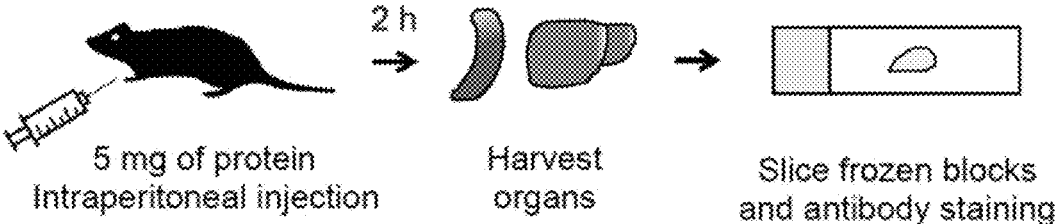
FIG. 11 is a schematic experimental design for determining the in vivo distribution of a C10 cell penetrating peptide.

5 μg of C10-dTomato, TAT-dTomato or dTomato was intraperitoneally injected into each mouse. 2 h later, the mouse was sacrificed. The blood vessels were perfused with 10 ml of PBS to remove residual blood from the tissues. The tissues were harvested, washed, and fixed with 4% paraformaldehyde. The fixed tissues were frozen using an optimal cutting temperature compound. Slice the frozen tissues were sliced to a thickness of 7-10 μm and stained with α-F4/80 or α-CD3 rat monoclonal antibody (Abcam, diluted 1:200) and α-rat IgG ALEXA FLUOR© 488 antibody (Invitrogen, 1:200 diluted). Nuclei were stained with PBS containing 0.01% Hoechst 33342 for 10 min. Fluorescence signals in the cytoplasm and nucleus were analyzed using a C2si confocal microscope (Nikon) or fluorescence microscope (Leica DMi8) (FIG. 11). Scale bars indicate 100 μm.

Figure 13:
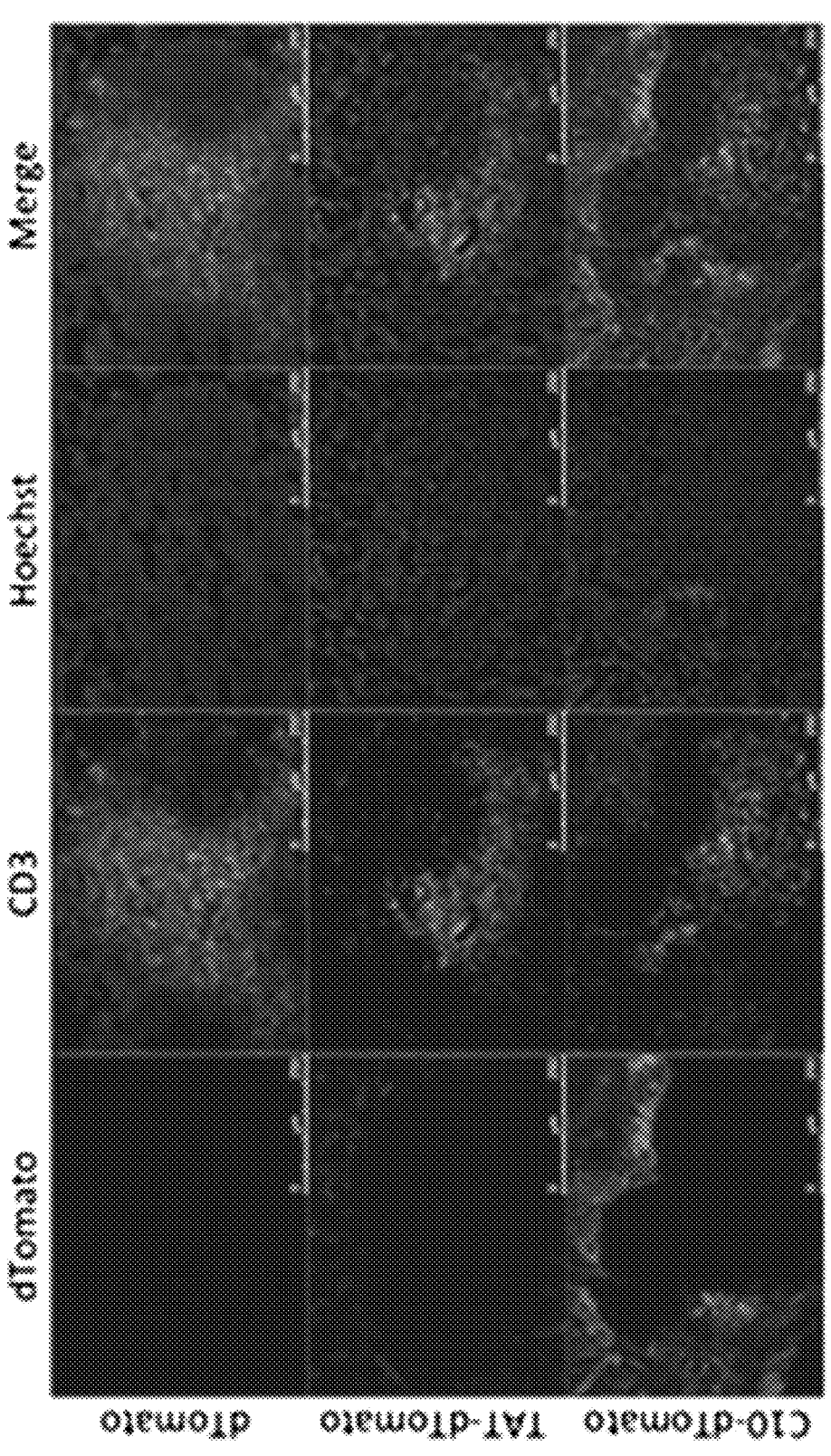
FIG. 13 shows confocal microscopy images of tissues isolated from mice after intraperitoneal injection of C10-dTomato, TAT-dTomato, and dTomato and staining with α-CD3 antibody 2 hours after the injection.

FIG. 12 shows confocal microscopy images of tissues isolated from mice after intraperitoneal injection of C10-dTomato, TAT-dTomato, and dTomato and staining with α-F4/80 antibody 2 hours after the injection. FIG. 13 shows confocal microscopy images of tissues isolated from mice after intraperitoneal injection of C10-dTomato, TAT-dTomato, and dTomato and staining with α-CD3 antibody 2 hours after the injection.

As shown in FIG. 12, most C10-dTomato signals were co-located with F4/80⁺ macrophages in various tissues. As a result, fluorescence signals from the tissues treated with C10-dTomato were stronger than those from the tissues treated with TAT-dTomato. These results indicate that the C10 cell penetrating peptide can deliver cargo molecules to macrophages with higher efficiency than the conventional cell penetrating peptide.

As shown in FIG. 13, C10-dTomato signals were not co-located with CD3+ T cells, indicating that C10-dTomato was delivered very specifically to macrophages, but not to T cells.

In conclusion, the C10 cell penetrating peptide is considered a new cell penetrating peptide that can deliver cargo molecules specifically to macrophages. This specific delivery could not be achieved by conventional cell penetrating peptides.

Experimental Example 7. Design, Production and Purification of C10-LRR Fusion Protein Public Single-Cell RNA Sequencing (scRNA-Seq)

Public scRNA-seq data can be downloaded from the Broad Institute Single Cell Portal using the identifier SCP548 (subject PBMCs) (M. Reyes, M. R. Filbin, R. P. Bhattacharyya, K. Billman, T. Eisenhaure, D. T. Hung, B. D. Levy, R. M. Baron, P. C. Blainey, M. B. Goldberg, N. Hacohen, An immune-cell signature of bacterial sepsis, Nat Med 26(3) (2020) 333-340.) PBMC samples were analyzed using three cohorts (healthy control, n=19; sepsis, n=4; sepsis-ICU, n=8).

Figure 14:
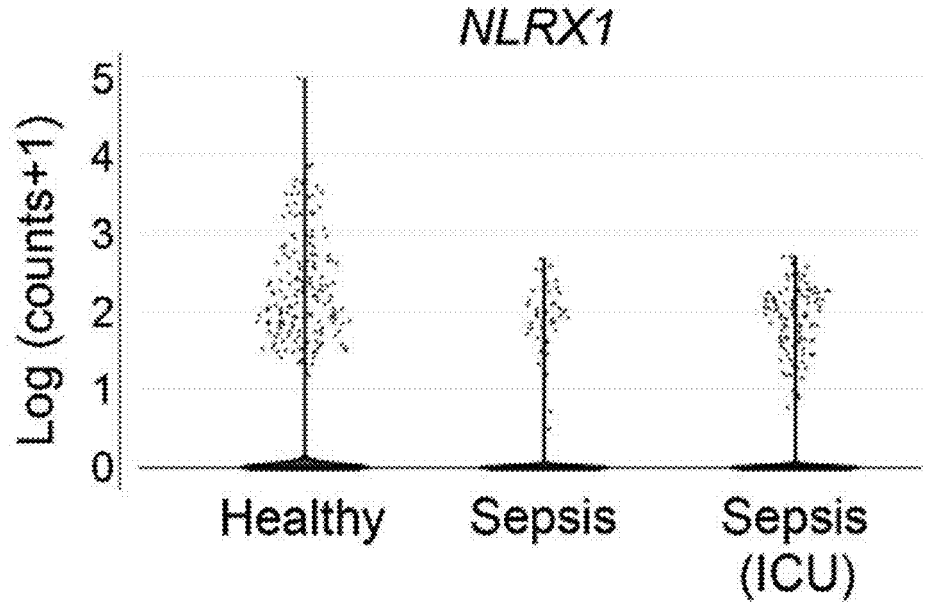
FIG. 14 shows the expression levels of NLRX1 in PBMC samples from healthy subjects and sepsis patients.

FIG. 14 shows the expression levels of NLRX1 in PBMC samples from healthy subjects and sepsis patients. The expression of NLRX1 was analyzed based on public single-cell RNA sequencing data (Reyes et al., 2020, Single Cell Portal (https://singlecell.broadinstitute.org/single_cell).

Based on public single-cell RNA sequencing (scRNA-seq) data (PBMC samples were analyzed using three cohorts (healthy control, n=19; sepsis, n=4; sepsis-ICU, n=8)), NLRX1 was reduced in sepsis patients compared to healthy controls, as shown in FIG. 14. That is, NLRX1 functions as a negative regulator for NF-κB signaling and inflammasome activation.

Figure 16:
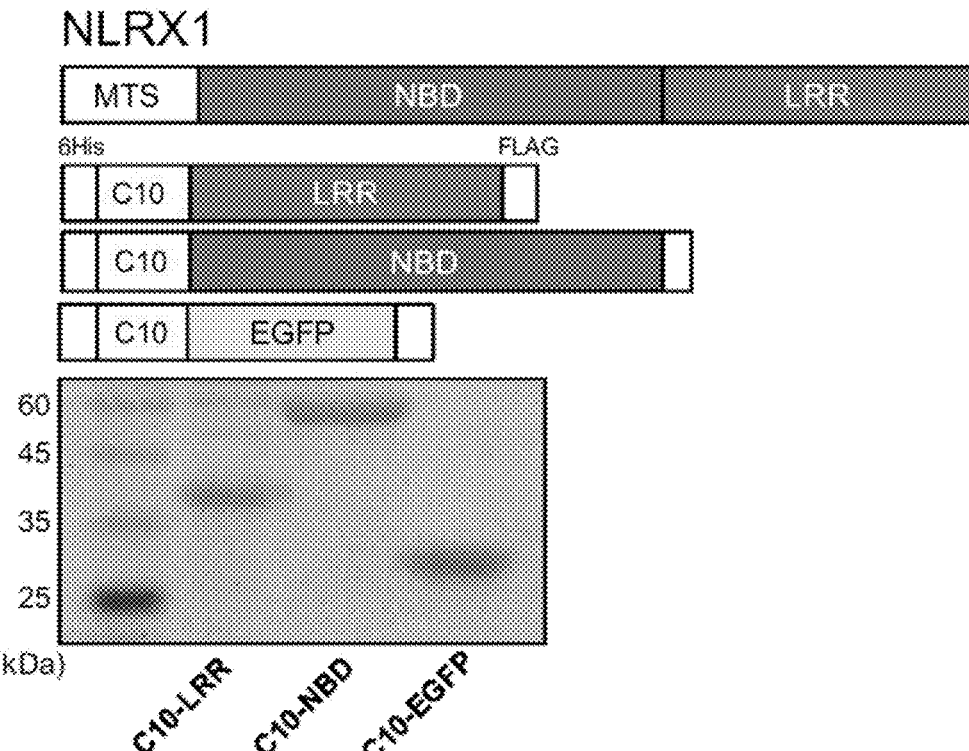
FIG. 16 shows DNA structures encoding C10-LRR, C10-NBD, and C10-EGFP recombinant proteins and the results of 12% SDS-PAGE for the recombinant proteins.

The inventors of the present invention predicted that effective delivery of NLRX1 into cells would allow NLRX1 to regulate NF-κB and inflammasome signaling in cells, enabling effective control over NLRX1 sepsis-related inflammatory responses. Thus, the inventors of the present invention have prepared a fusion product (recombinant protein) of the inventive C10 cell penetrating peptide and NLRX1 to determine whether the inventive C10 cell penetrating peptide effectively delivers NLRX1 cargo molecules into cells in vitro or in vitro and the delivered cargo molecules actually exhibit their effects. To this end, DNAs encoding C10-LRR and C10-NBD recombinant proteins in which C10 was bound to two domains of NLRX1 (LRR-NBD), respectively, and a DNA encoding C10-EGFP recombinant protein were designed (FIG. 16). EGFP was used as a control.

FIG. 16 shows the DNA structures encoding C10-LRR, C10-NBD, and C10-EGFP recombinant proteins and the results of 12% SDS-PAGE for the recombinant proteins. As shown in FIG. 16, all C10-LRR, C10-NBD, and C10-EGFP recombinant proteins were successfully produced.

Figure 15:
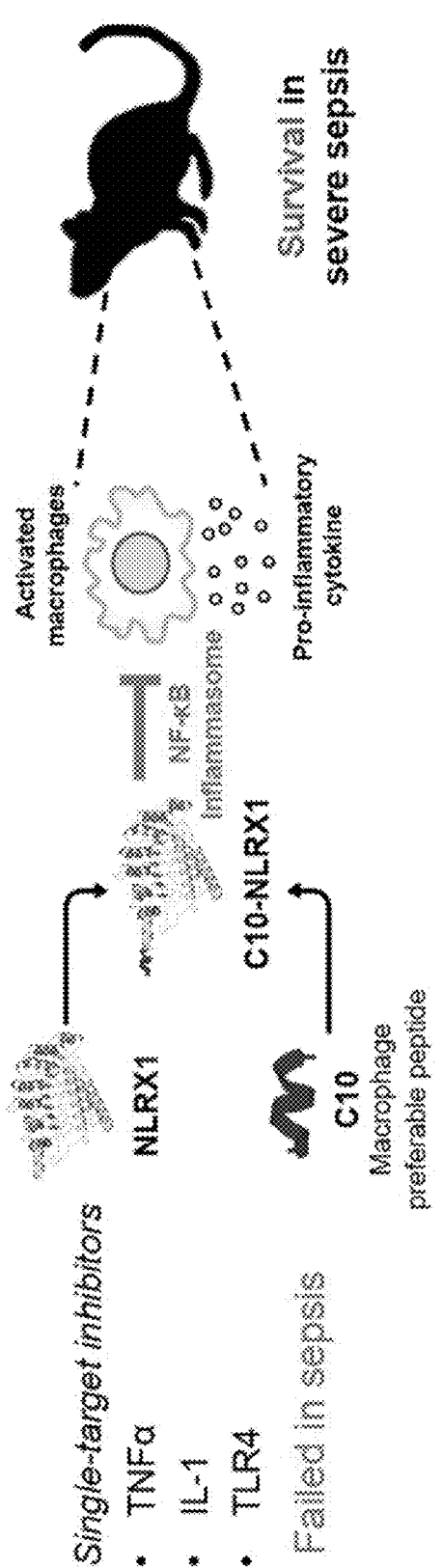
FIG. 15 schematically shows the pharmacological mechanism of C10-LRR, C10-NBD, and C10-EGFP recombinant proteins.

FIG. 15 schematically shows the pharmacological mechanism of the C10-LRR, C10-NBD, and C10-EGFP recombinant proteins designed and prepared as fusion products of the inventive C10 cell penetrating peptide and NLRX1 protein.

Experimental Example 8. Analysis of Delivery Efficiency of C10-LRR Fusion Protein-1

Experimental Animals 7- to 8-week-old male or female C57BL/6 mice were housed and bred in a specific pathogen-free animal facility at Hanyang University. The mice were acclimatized for two weeks before the experiment. The mice were housed in the facility maintained at a temperature of 21±2° C. and a humidity of 40-60% on a 12-h light/dark cycle and were given water and food ad libitum over the entire experimental period. All animal experiments were conducted in accordance with the Animal Care and Use Protocol approved by the Institutional Animal Care and Use Committee of Hanyang University.

Sample Administration and Sampling

Peritoneal macrophages were isolated from the mouse. To this end, 5 ml of PBS was intraperitoneally administered to the mouse. The obtained intraperitoneal fluid was dispensed into a culture plate and incubated in a 5% $CO_2$ incubator at 37° C. for 2 h. After completion of the incubation, the supernatant was removed, cells were washed with PBS, and non-adherent cells were counted. Adherent cells were primary peritoneal macrophages.

The obtained primary peritoneal macrophages were seeded into a 96- or 12-well plate at a density of $2×10^5$ cells/well. The C10-LRR or TAT-LRR recombinant protein, LRR or PBS (control) (2 μM) was added to the wells, followed by culture in a 5% $CO_2$ incubator at 37° C. for 1 h. After completion of the culture, cells were harvested by centrifugation and washed twice with PBS buffer. Cells were treated with trypsin at 37° C. for 10 min to eliminate proteins attached to the cell membrane. The trypsin was neutralized in a DMEM culture medium supplemented with 10% FBS at 37° C. After cells were washed with PBS, flow cytometry (FACS Canto II, BD Bioscience) was performed. Data were analyzed using FLOWJO™ software (Tree Star).

Statistics

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

Figure 17:
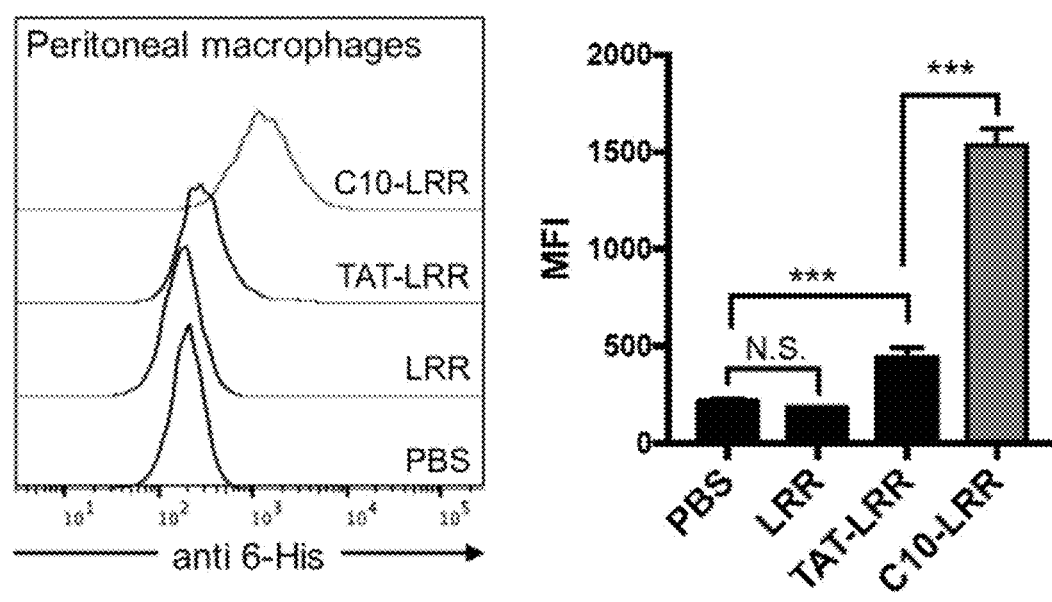
FIG. 17 shows the results of flow cytometry for primary peritoneal macrophages after treatment with C10-LRR, TAT-LRR, LRR, and PBS (control) and culture for 1 hour.

FIG. 17 shows the results of flow cytometry for primary peritoneal macrophages after treatment with C10-LRR, TAT-LRR, LRR, and PBS (control) and culture for 1 hour.

As shown in FIG. 17, the LRR protein was effectively delivered into mouse peritoneal macrophages by the C10 cell penetrating peptide. In contrast, when the TAT cell penetrating peptide was used, the LRR protein was not substantially delivered. From these experimental results, it can be seen that the C10 cell penetrating peptide enables significant macrophage-specific delivery.

Experimental Example 9. Analysis of Delivery Efficiency of C10-LRR Fusion Protein-2

Cell Lines and Culture

HeLa cells were purchased from ATCC and stored in DMEM or RPMI (Corning) media. Culture media supplemented with 10% fetal bovine serum and 1% penicillin/ streptomycin were used. Cells were cultured in a 5% $CO_2$ incubator at 37° C.

Fluorescence Microscopy

Hela cells were seeded into 6-well plates at a density of $2 \times 10^5$ cells/well. 2 μM C10-LRR was added to the wells and cultured in a 5% $CO_2$ incubator at 37° C. for 1 h. Thereafter, cells were washed three times with PBS and fixed with 4% paraformaldehyde phosphate buffer solution (Wako) for 10 min. Nuclei were stained with PBS containing 0.01% Hoechst 33342 for 10 min and cells were washed twice with PBS. Fluorescence signals in the cytoplasm and nucleus were analyzed using a C2si confocal microscope (Nikon). Scale bars indicate 100 μm.

Figure 18:
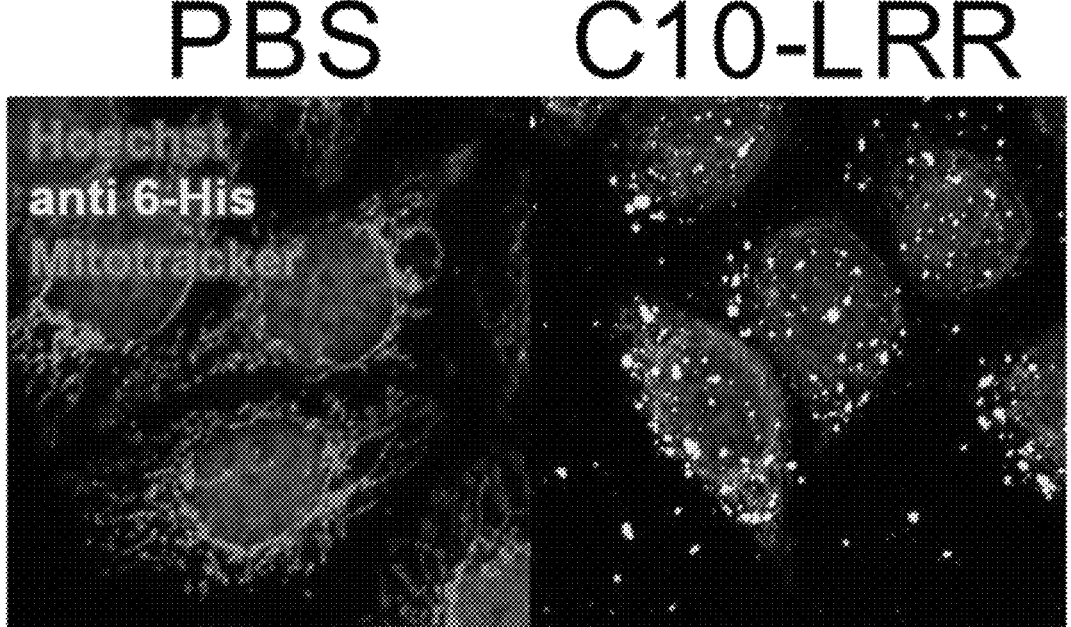
FIG. 18 shows a confocal microscopy image revealing the distribution of C10-LRR in HeLA cells after treatment of the cells with C10-LRR.

FIG. 18 shows a confocal microscopy image revealing the distribution of C10-LRR in HeLA cells after treatment of the cells with C10-LRR. Red is MITOTRACKER™ and represents fluorescence signals in the mitochondria (cytoplasm), Blue is Hoechst and represents fluorescence signals in the nucleus, and green is anti 6His and represents fluorescence signals from C10-LRR.

As shown in FIG. 18, C10-LRR was distributed in both the cytoplasm and nucleus. It is believed that C10-LRR enters the cells through endocytosis and diffuses in the cells.

Experimental Examples 7 and 8 revealed that binding of the C10 cell penetrating peptide to a cargo material such as NLRX1 protein is effective in selectively delivering the cargo material into primary macrophages.

Experimental Example 10. Analysis of C10 Variants

Various variants for comparative analysis were generated to investigate the roles of the amino acids constituting C10.

Cell Lines and Culture

HeLa and Jurkat cells were purchased from ATCC and stored in DMEM or RPMI (Corning) media. Culture media supplemented with 10% fetal bovine serum and 1% penicillin/streptomycin were used. Cells were cultured in a 5% $CO_2$ incubator at 37° C.

Flow Cytometry

Jurkat or HeLa cells were seeded into 96-well or 12-well plates at a density of $2 \times 10^5$ cells/well. The recombinant proteins of Examples 5-10 (each 5 NM) were added to the wells and cultured in a 5% $CO_2$ incubator at 37° C. for 1 h. After completion of the culture, cells were harvested by centrifugation and washed twice with PBS buffer. The washed cells were treated with trypsin at 37° C. for 10 min to eliminate proteins attached to the cell membrane. Next, DMEM culture media supplemented with 10% FBS were added to the cells to neutralize the trypsin. Cells were harvested, washed with PBS, and subjected to flow cytometry (FACS Canto II, BD Bioscience). Data were analyzed using FLOWJO™ software (Tree Star).

Statistics

For statistical analysis of the experimental data, significant differences in mean values between groups were determined using two-tailed Student's t-test and one- or two-way ANOVA. * indicates a significant difference at $p < 0.05$,  indicates a significant difference at $p < 0.01$, * indicates a significant difference at $p < 0.001$, and N.S indicates no significant difference. MFI indicates median fluorescence intensity. Error bars indicate S.D.

Figure 19:
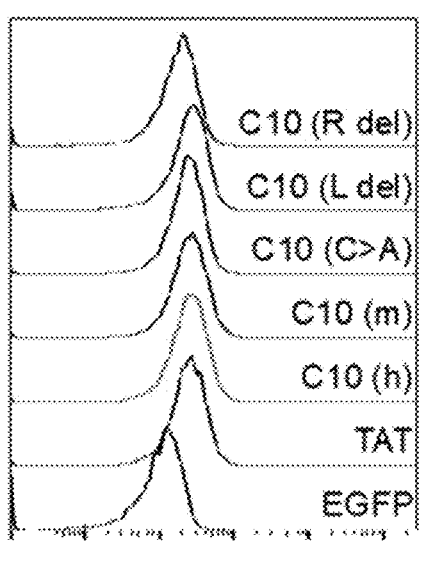
FIGS. 19 and 20 show the results of flow cytometry for Jurkat cells after treatment with recombinant proteins of Examples 5-10, TAT-EGFP, and EGFP (control) and culture for 1 hour.
Figure 19:
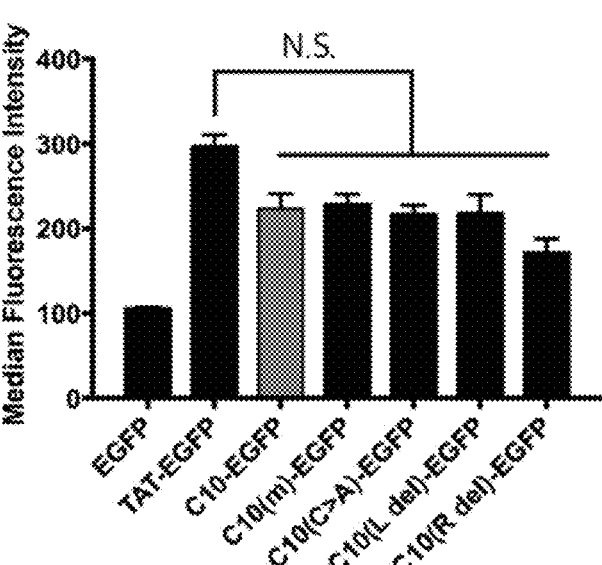
Figure 20:
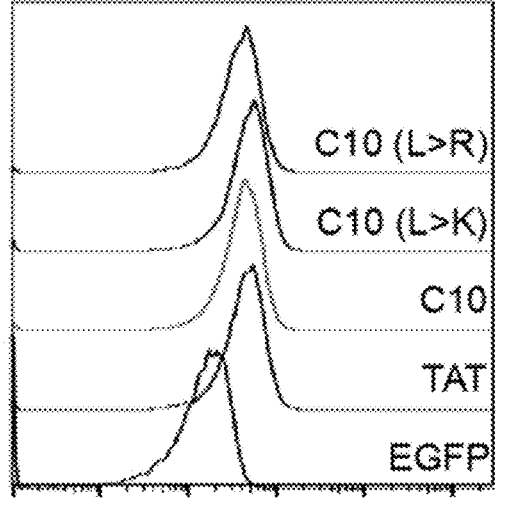
Figure 20:
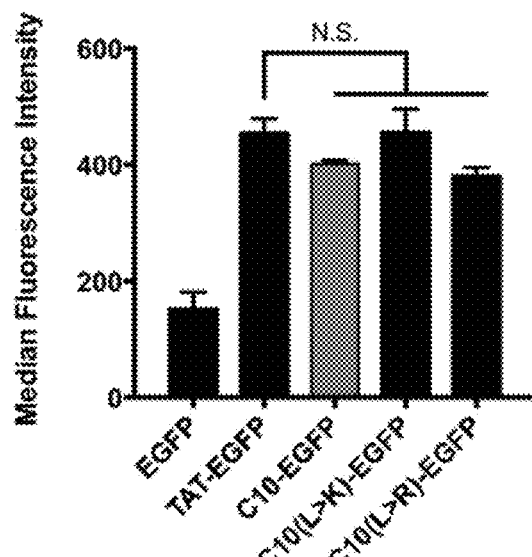
Figure 21:
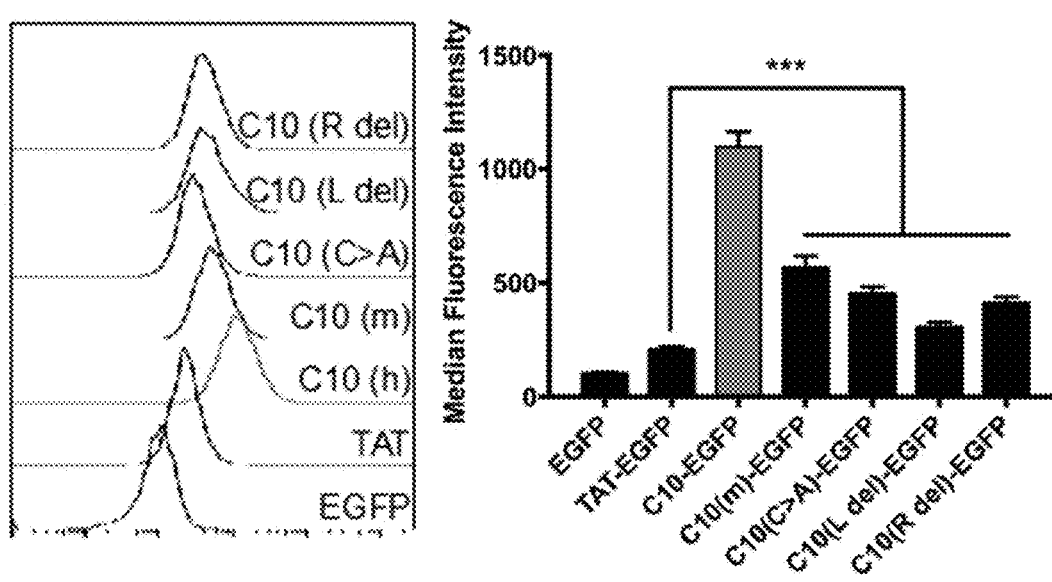
FIGS. 21 and 22 show the results of flow cytometry for Hela cells after treatment with recombinant proteins of Examples 5-10, TAT-EGFP, and EGFP (control) and culture for 1 hour.
Figure 22:
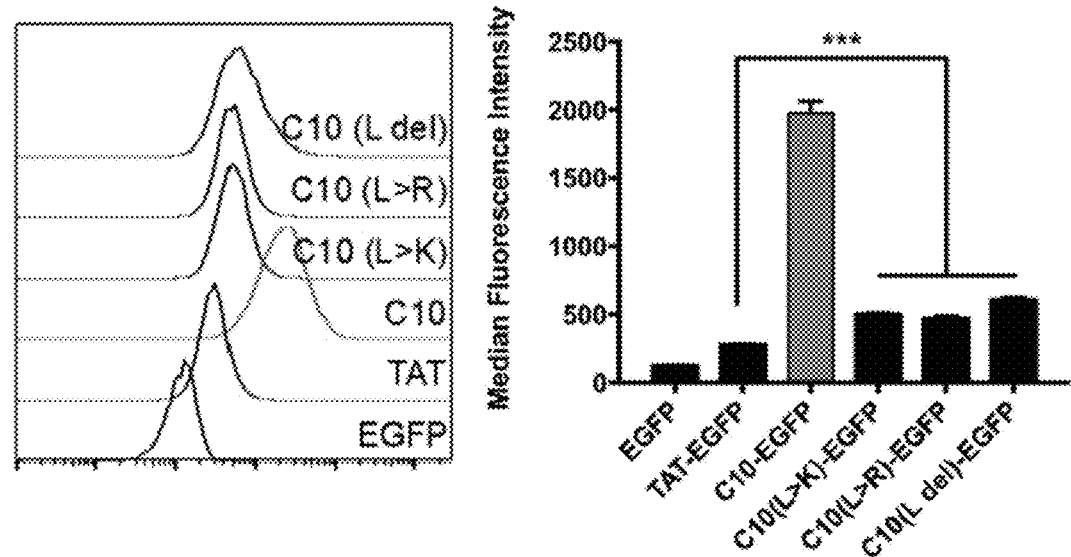

FIGS. 19 and 20 show the results of flow cytometry for Jurkat cells after treatment with the recombinant proteins of Examples 5-10, TAT-EGFP, and EGFP (control) and culture for 1 hour. FIGS. 21 and 22 show the results of flow cytometry for Hela cells after treatment with the recombinant proteins of Examples 5-10, TAT-EGFP, and EGFP (control) and culture for 1 hour.

As shown in FIGS. 19 to 22, the recombinant proteins of Examples 5-10 had general cell penetration efficiencies in Jurkat cells with no significant differences. Further, the cell penetration efficiencies of the recombinant proteins of Examples 5-10 in Jurkat cells were not significantly different from that of the conventional cell penetrating peptide (TAT). In contrast, the recombinant proteins of Examples 5-10 showed significantly higher cell penetration efficiencies in Hela cells than the TAT cell penetrating peptide.

Particularly, the C10 cell penetrating peptide (SEQ ID NO: 1) showed significantly increased cell penetration efficiency compared to its variants. The cell penetration efficiencies of the recombinant proteins of Examples 5-10 were specifically compared. The largest reduction in efficiency occurred when the leucine residue at position 1 was deleted compared to when C10 was unmodified, demonstrating that leucine is preferable as an amino acid residue at position 1 in the role of AP in intracellular protein delivery.

The variant produced by substituting the amino acid residue at position 1 with arginine (R) and the variant produced by substituting the amino acid residue at position 1 with lysine (K) were excellent in delivery efficiency over the TAT cell penetrating peptide but had significantly lower cell penetration efficiencies than the C10 cell penetrating peptide (SEQ ID NO: 1), demonstrating that leucine plays a very important function and role in C10. Arginine (R) and lysine (K) are mainly used in cell penetrating peptides.

Next, the variant (SEQ ID NO: 9) produced by deleting the arginine residue at position 10 and the variant (SEQ ID NO: 5) produced by substituting the cysteine residue at position 8 with alanine were excellent in cell penetration efficiency over the TAT cell penetrating peptide and the variants of SEQ ID NOS: 7, 11, and 13 but had significantly lower cell penetration efficiencies than the C10 cell penetrating peptide of SEQ ID NO: 1, indicating that arginine at position 10 and cysteine at position 8 play the second most important function and role in C10.

The variant (SEQ ID NO: 3) produced by substituting the leucine residue at position 3 with methionine showed a higher cell penetration efficiency than the TAT cell penetrating peptide and other variants of C10 but had a significantly lower cell penetration efficiency than the C10 cell penetrating peptide of SEQ ID NO: 1, indicating that the leucine residue at position 3 is less important in C10 than the leucine residue at position 1 but still plays an important function and role in delivery efficiency to cells.

Experimental Example 11. Analysis of Function of the C10 Cell Penetrating Peptide in Sepsis Animal Models An investigation was made as to whether the inventive C10 cell penetrating peptide has the function of delivering biologically active substances even in vivo. To this end, the C10 cell penetrating peptide was fused with each of the LRR and NBD domains of NLRX1 protein to produce C10-LRR and C10-NBD recombinant proteins, respectively, as described above. The fusion products were intraperitoneally injected into sepsis animals to determine their effects on the disease. PBS and C10-EGFP were used as controls.

Experimental Animals 7- to 8-week-old male or female C57BL/6 mice were housed and bred in a specific pathogen-free animal facility at Hanyang University. The mice were acclimatized for two weeks before the experiment. The mice were housed in the facility maintained at a temperature of 21±2° C. and a humidity of 40-60% on a 12-h light/dark cycle and were given water and food ad libitum over the entire experimental period. All animal experiments were conducted in accordance with the Animal Care and Use Protocol approved by the Institutional Animal Care and Use Committee of Hanyang University.

Sample Administration and Sampling

For sample administration, mice were randomly divided into four groups, 24 animals per group. LPS (2 mg/kg) and PBS (1 mg/kg) were intraperitoneally injected (I.P injection) at 0 h and LPS (5 mg/kg) and PBS (1 mg/kg) were intraperitoneally injected at 5 h ("PBS", negative control). LPS (2 mg/kg) and the C10-EGFP recombinant protein (1 mg/kg) were intraperitoneally injected (I.P injection) at 0 h and LPS (5 mg/kg) and the C10-EGFP recombinant protein (1 mg/kg) were intraperitoneally injected at 5 h ("C10-EGFP-administered group"). LPS (2 mg/kg) and the C10-LRR recombinant protein (1 mg/kg) were intraperitoneally injected (I.P injection) at 0 h and LPS (5 mg/kg) and the C10-LRR recombinant protein (1 mg/kg) were intraperitoneally injected at 5 h ("C10-LRR-administered group"). LPS (2 mg/kg) and the C10-NBD recombinant protein (1 mg/kg) were intraperitoneally injected (I.P injection) at 0 h and LPS (5 mg/kg) and the C10-NBD recombinant protein (1 mg/kg) were intraperitoneally injected at 5 h ("C10-NBD-administered group"). The dose of the C10-LRR recombinant protein was changed from 1 mg/kg to 0.2 mg/kg to prepare another C10-LRR-administered group. These groups were measured for changes in survival and weight every 24 h for a total of 7 days. 2 h or 24 h after sample injection at 5 h, blood was harvested and analyzed for cytokine level and AST activity. The Sham group is a normal group without any treatment.

5 Groups of Animal Models

Group 1 (PBS): LPS (2 mg/kg) and PBS (1 mg/kg) were intraperitoneally administered at 0 h and LPS (5 mg/kg) and PBS (1 mg/kg) were intraperitoneally administered at 5 h.

Group 2 (C10-EGFP): LPS (2 mg/kg) and the C10-EGFP recombinant protein (1 mg/kg) were intraperitoneally administered at 0 h and LPS (5 mg/kg) and the C10-EGFP recombinant protein (1 mg/kg) were intraperitoneally administered at 5 h.

Group 3 (C10-NBD): LPS (2 mg/kg) and the C10-NBD recombinant protein (1 mg/kg) were intraperitoneally administered at 0 h and LPS (5 mg/kg) and the C10-NBD recombinant protein (1 mg/kg) were intraperitoneally administered at 5 h.

Group 4 (C10-LRR): LPS (2 mg/kg) and the C10-LRR recombinant protein (1 mg/kg) were intraperitoneally administered at 0 h and LPS (5 mg/kg) and the C10-LRR recombinant protein (1 mg/kg) were intraperitoneally administered at 5 h.

Group 5 (C10-LRR): LPS (2 mg/kg) and the C10-LRR recombinant protein (0.2 mg/kg) were intraperitoneally administered at 0 h and LPS (5 mg/kg) and the C10-LRR recombination protein (0.2 mg/kg) were intraperitoneally administered at 5 h.

ELISA

Blood was sampled from the animal models through eye bleeding 2 h or 24 h after injection. Each blood sample was centrifuged to separate serum, which was analyzed by ELISA. The levels of IL-6, TNFα, and IL-1β in the serum were measured using an ELISA kit (BioLegend) according to the manufacturer's protocol.

Statistics

For statistical analysis of the experimental data, significant differences in mean values between groups were determined using two-tailed Student's t-test and one- or two-way ANOVA. * indicates a significant difference at p<0.05,  indicates a significant difference at p<0.01, * indicates a significant difference at p<0.001, and N.S indicates no significant difference. MFI indicates median fluorescence intensity. Error bars indicate S.D.

Figure 23:
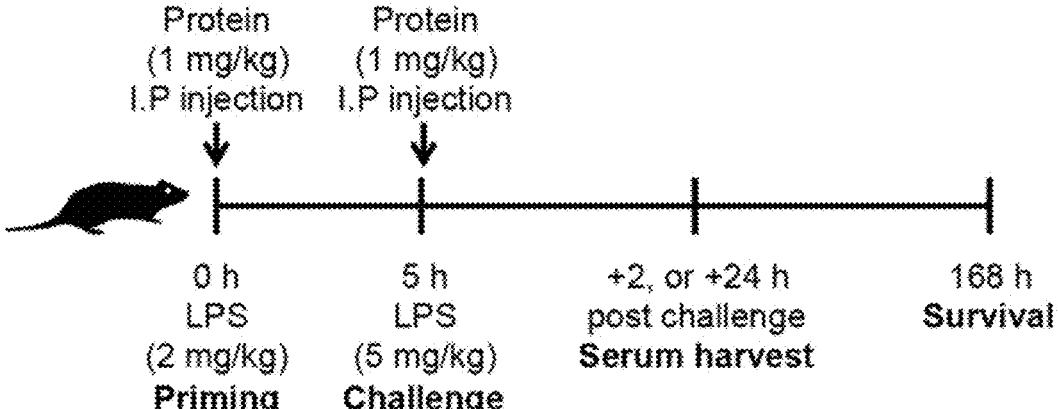
FIG. 23 schematically shows an experimental design for a sepsis animal model.

FIG. 23 schematically shows an experimental design for a sepsis animal model. As shown in FIG. 23, an animal model with lethal sepsis induced by LPS is established and C10-LRR is injected in vivo into the animal model to determine its effect. Inflammasome signaling and pyroptosis are known to play very important roles in the early stages of sepsis and sepsis-related mortality. Thus, LPS was injected using a prime/challenge model to establish animal models with lethal sepsis in which Caspase-11- and Caspase-1-mediated inflammasome signaling was induced. Specifically, 2 mg/kg of LPS was first administered intraperitoneally (prime). 5 h later, 5 mg/kg of LPS was administered intraperitoneally (challenge). As a result, the induction of sepsis was confirmed by taking into comprehensive consideration the increased activity of macrophages compared to monocytes in the spleen, liver, kidney, lung, and peritoneum and the appearance of external symptoms. The C10-LRR, C10-NBD, and C10-EGFP recombinant proteins (each 1 mg/kg) and PBS were administered at the same times as LPS. The survivals and weights of the animal models were monitored.

Figure 24:
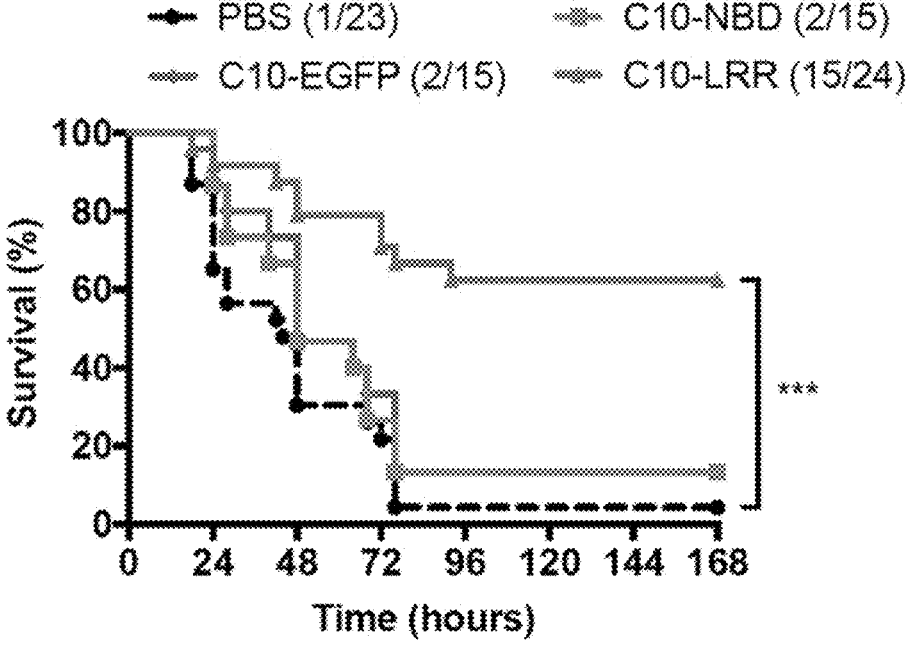
FIG. 24 shows the survivals of animal models in Group 1 (PBS), Group 2 (C10-EGFP), Group 3 (C10-NBD), and Group 4 (C10-LRR), which were measured for 7 days.
Figure 25:
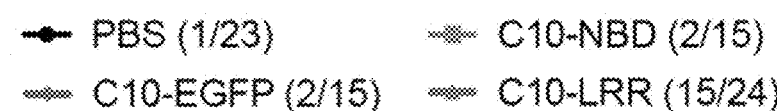
FIG. 25 shows the weights of animal models in Group 1 (PBS), Group 2 (C10-EGFP), Group 3 (C10-NBD), and Group 4 (C10-LRR), which were measured for 7 days.
Figure 25:
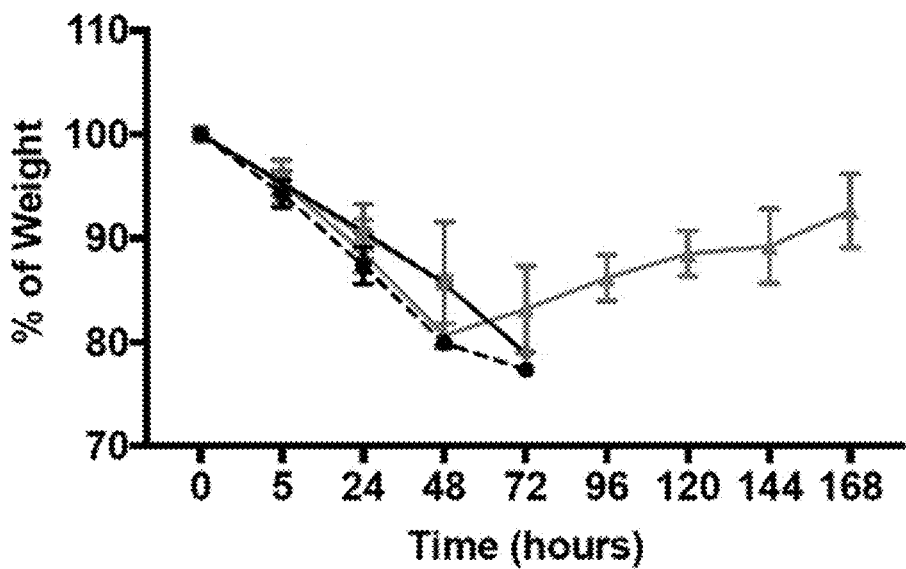

FIG. 24 shows the survivals of the animal models in Group 1 (PBS), Group 2 (C10-EGFP), Group 3 (C10-NBD), and Group 4 (C10-LRR), which were measured for 7 days. FIG. 25 shows the weights of the animal models in Group 1 (PBS), Group 2 (C10-EGFP), Group 3 (C10-NBD), and Group 4 (C10-LRR), which were measured for 7 days.

As shown in FIG. 24, the survival of Group 4 treated with C10-LRR was significantly improved compared to those of the groups treated with C10-EGFP and C10-NBD.

As shown in FIG. 25, the weight of Group 4 treated with C10-LRR was significantly restored from 48 h, unlike those of the groups treated with C10-EGFP and C10-NBD. The inventive C10-LRR was confirmed to allow the animal models to recover from severe inflammatory response and abnormal physiological function of LPS-induced sepsis.

Figure 26:
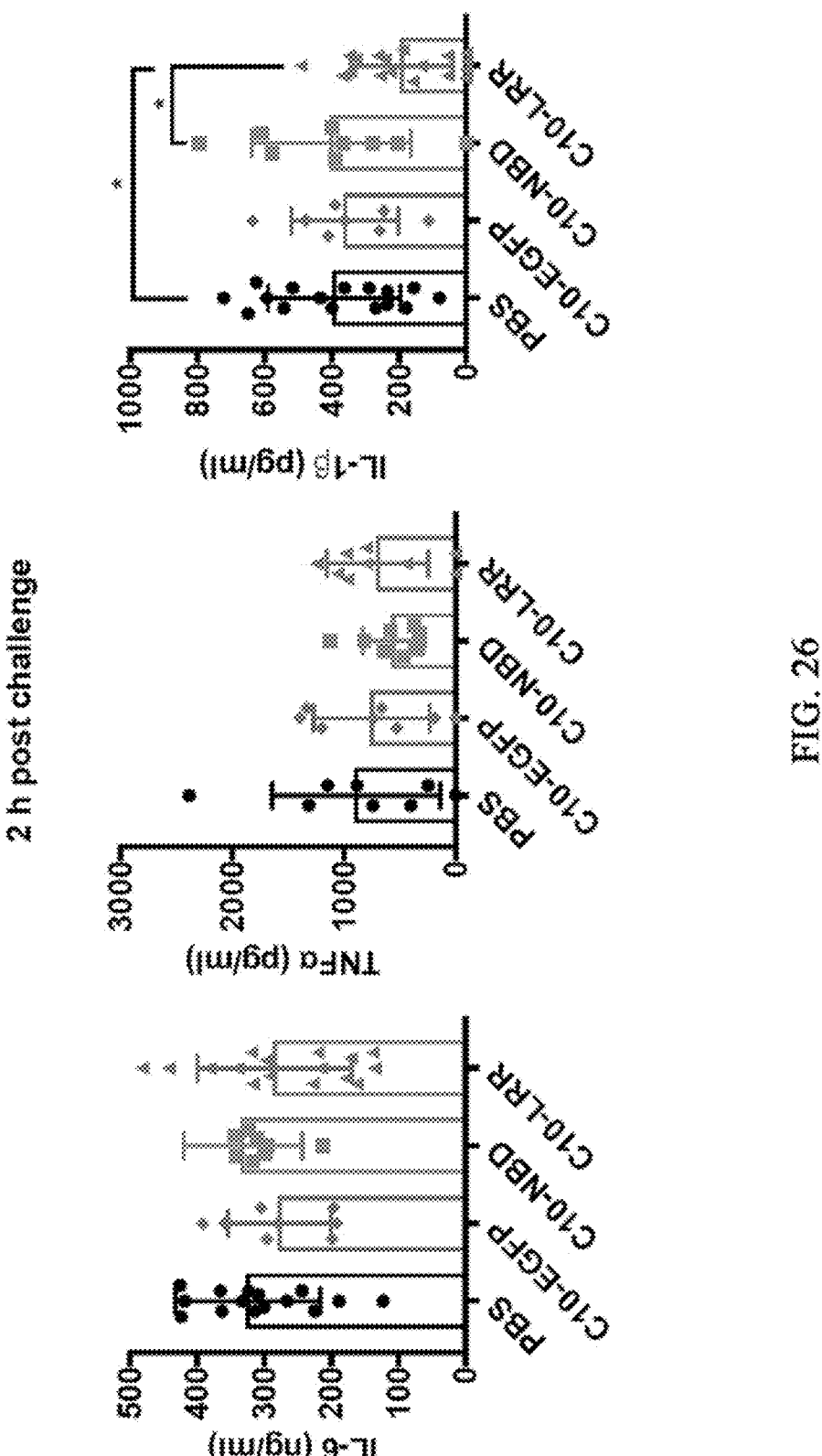
FIG. 26 shows the expression levels of IL-6, TNF-$\alpha$, and IL-1$\beta$ in animal models in Group 1 (PBS), Group 2 (C10-EGFP), Group 3 (C10-NBD), and Group 4 (C10-LRR) 2 h post challenge, which were measured by ELISA.
Figure 27:
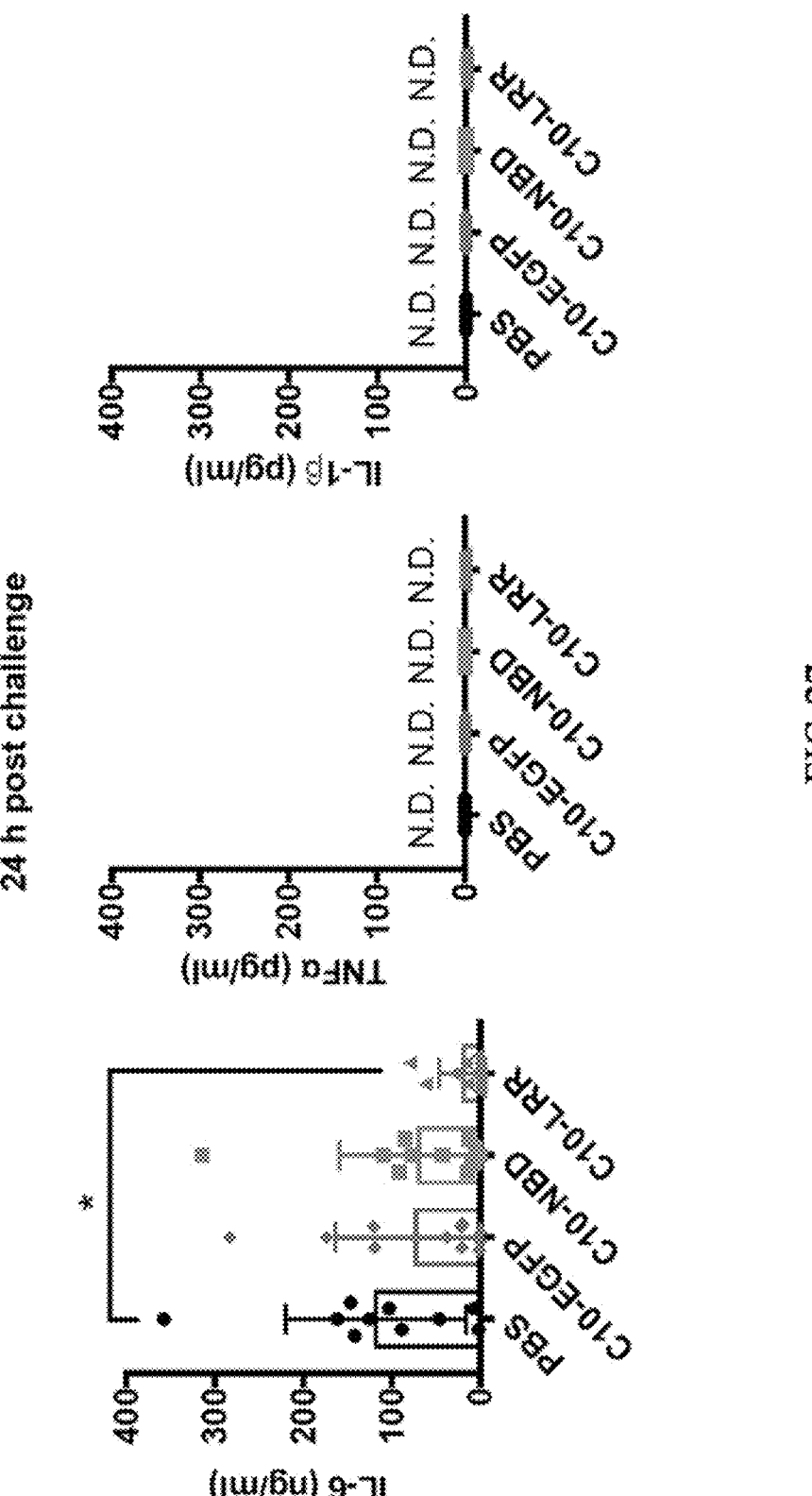
FIG. 27 shows the expression levels of IL-6, TNF-$\alpha$, and IL-1$\beta$ in animal models in Group 1 (PBS), Group 2 (C10-EGFP), Group 3 (C10-NBD), and Group 4 (C10-LRR) 24 h post challenge, which were measured by ELISA.

FIG. 26 shows the expression levels of IL-6, TNF-α, and IL-1β in the animal models in Group 1 (PBS), Group 2 (C10-EGFP), Group 3 (C10-NBD), and Group 4 (C10-LRR) 2 h post challenge, which were measured by ELISA. FIG. 27 shows the expression levels of IL-6, TNF-α, and IL-1β in the animal models in Group 1 (PBS), Group 2 (C10-EGFP), Group 3 (C10-NBD), and Group 4 (C10-LRR) 24 h post challenge, which were measured by ELISA.

As shown in FIG. 26, the serum IL-1β level of Group 4 treated with C10-LRR 2 h after LPS (5 mg/kg) injection (challenge) was significantly low compared to those of the other groups.

As shown in FIG. 27, the serum IL-6 level of Group 4 treated with C10-LRR 24 h after LPS (5 mg/kg) injection (challenge) was significantly low compared to those of the other groups. These results concluded that the inventive C10-LRR recombinant protein would be effective in preventing or treating sepsis due to its ability to reduce IL-1β and IL-6 levels in vivo.

Figure 28:
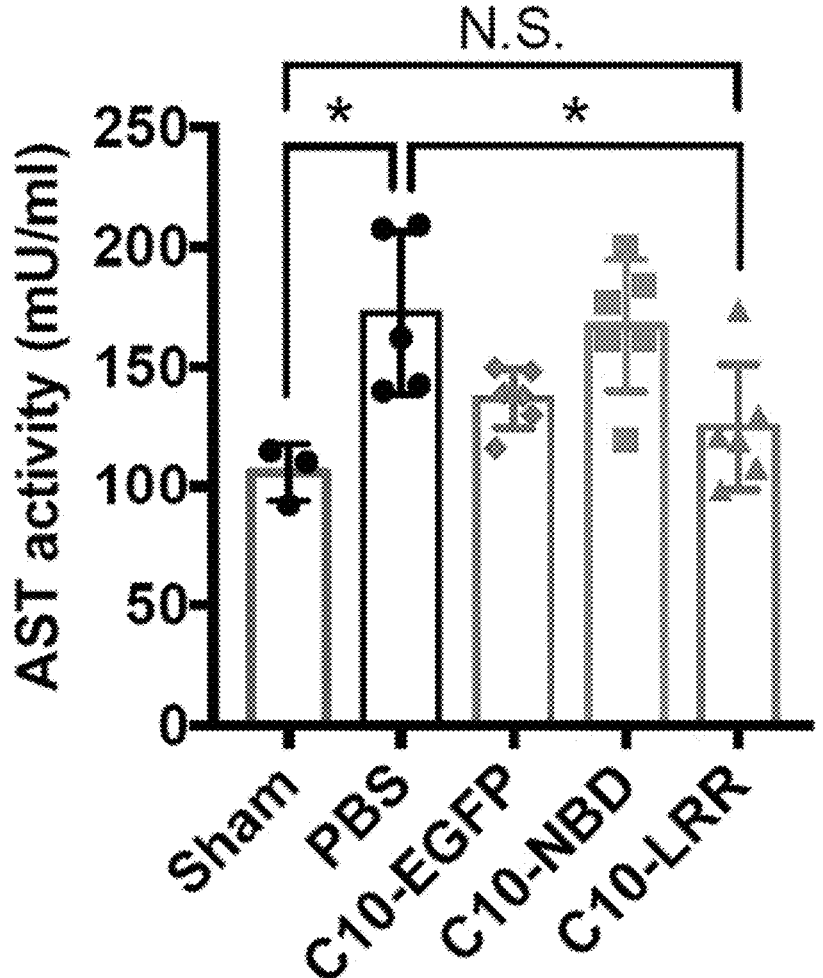
FIG. 28 shows AST activities in animal models in Group 1 (PBS), Group 2 (C10-EGFP), Group 3 (C10-NBD), and Group 4 (C10-LRR) 2 h post challenge.

FIG. 28 shows AST activities in the animal models in Group 1 (PBS), Group 2 (C10-EGFP), Group 3 (C10-NBD), and Group 4 (C10-LRR) 2 h post challenge.

As shown in FIG. 28, the injection of 5 mg/kg of LPS increased the level of AST in the blood due to hepatotoxicity of LPS. However, the AST value of Group 4 treated with C10-LRR was maintained at a level similar to that of the Sham group (normal group). The AST levels of the other groups were significantly high compared to that of the Sham group (normal group).

Figure 29:
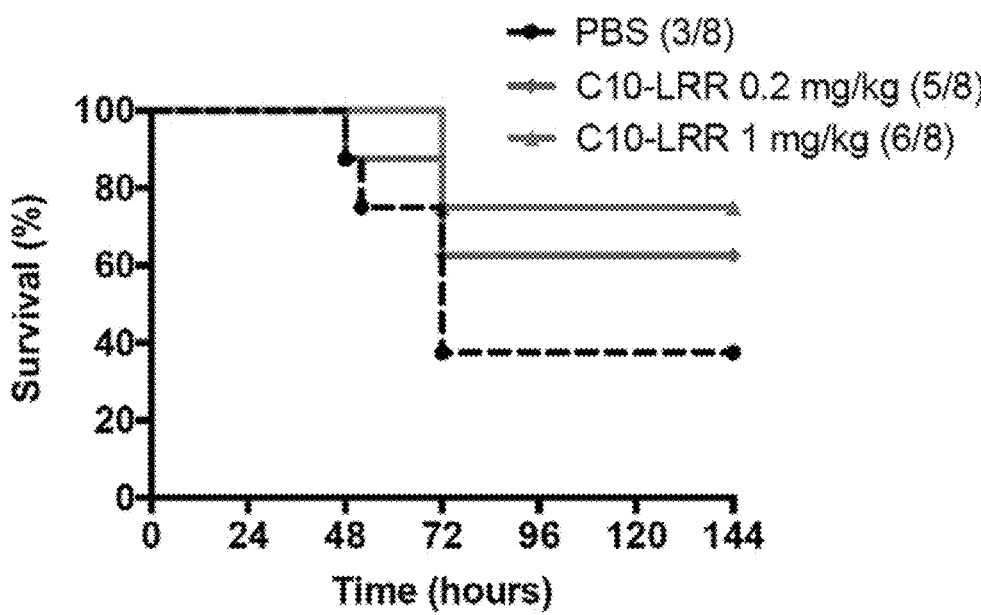
FIG. 29 shows the survivals of animal models in Group (C10-LRR) and Group 5 (C10-LRR, 0.2 mg/kg), which were measured for 6 days.

FIG. 29 shows the survivals of the animal models in Group (C10-LRR) and Group 5 (C10-LRR, 0.2 mg/kg), which were measured for 6 days; As shown in FIG. 29, when the animal models with LPS-induced sepsis were treated with different doses of C10-LRR, the effect of C10-LRR in the animal models was increased in a dose-dependent manner.

Experimental Example 12. Inhibitory Effects of C10-LRR on NF-κB Activation and IL-6 Production in Macrophages

ELISA

Peritoneal macrophages were seeded into 96- or 12-well plates and cultured in a 5% $CO_2$ incubator at 37° C. until adherence. Floating cells were removed with PBS. For inflammasome activation in the adherent macrophages, the macrophages were cultured with 1 mg/ml LPS for 4 h. At this time, the culture was treated with various concentrations (0.2 μM, 0.5 μM, and 1 μM) of each of the recombinant proteins (C10-LRR, C10-NBD, and C10-EGFP) together with LPS for stimulation. Thereafter, each culture supernatant was collected for ELISA. The levels of IL-6, TNFα, and IL-1β in the culture supernatant were measured using an ELISA kit (BioLegend) according to the manufacturer's protocol.

Cytotoxicity Assay

Peritoneal macrophages were seeded into 96-well plates at a density of $1 \times 10^5$ cells/well, added with various concentrations (0.2 μM, 0.5 μM, 1 μM) of each of the recombinant proteins (C10-LRR, C10-NBD, and C10-EGFP) and 1 mg/ml LPS (055:B5, Sigma L2880), and cultured for 24 h. Thereafter, 10 μl of cell counting kit-8 (CCK-8) solvent (Dojindo) was added to each well. The absorbance at 450 nm was monitored using a microplate reader (iMark, Bio-Rad) every 30 min for 4 h to determine the number of viable cells. The peritoneal macrophages used were obtained in the same manner as in Experimental Example 8.

Statistics

For statistical analysis of the experimental data, significant differences in mean values between groups were determined using two-tailed Student's t-test and one- or two-way ANOVA. * indicates a significant difference at $p < 0.05$,  indicates a significant difference at $p < 0.01$, * indicates a significant difference at $p < 0.001$, and N.S indicates no significant difference. MFI indicates median fluorescence intensity. Error bars indicate S.D.

The treatment of the LPS-induced sepsis animal models with C10-LRR led to a reduction in IL-6 level. Based on this, the in vitro function of macrophages was assessed.

Peritoneal macrophages were isolated, added with LPS and each of the recombinant proteins (C10-LRR, C10-NBD, and C10-EGFP), and cultured for 4 h. The levels of IL-6 and TNF-α in each culture supernatant were measured.

Figure 30:
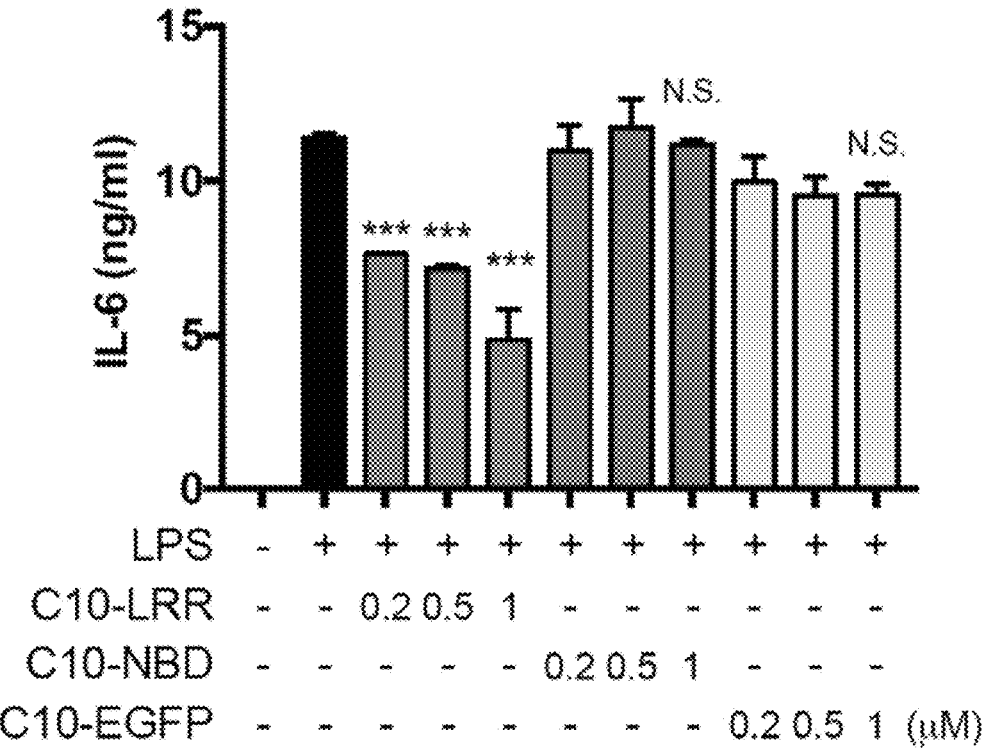
FIGS. 30 and 31 show the levels of IL-6 and TNF-$\alpha$ in peritoneal macrophages after treatment with LPS and recombinant proteins, respectively, which were measured by ELISA.
Figure 31:
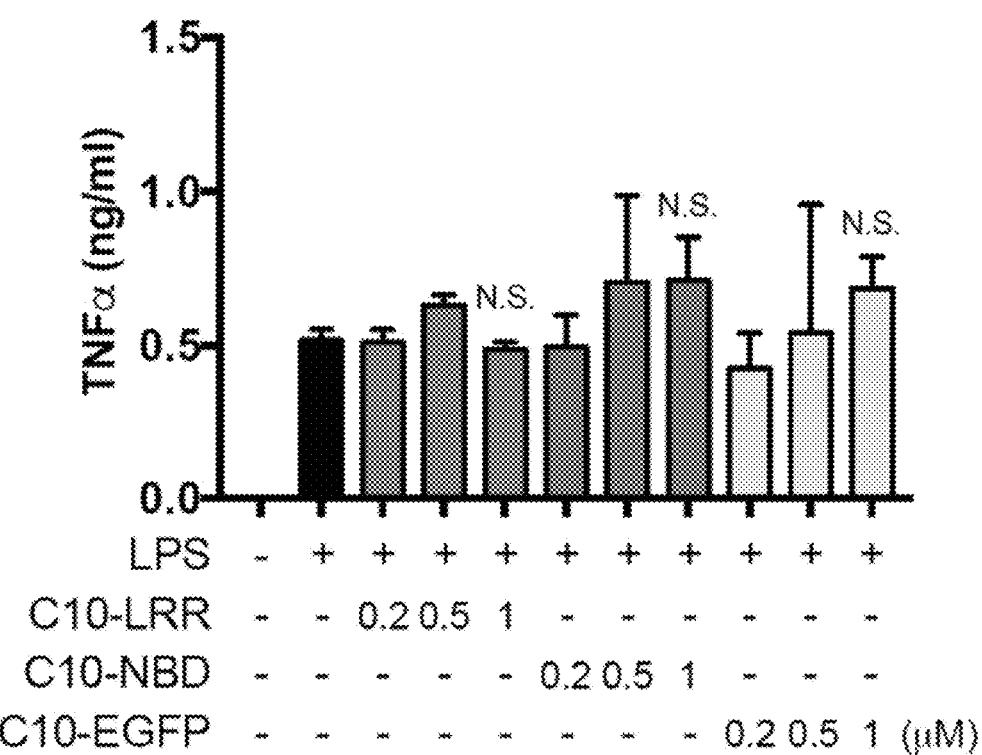

FIGS. 30 and 31 show the levels of IL-6 and TNF-α in the peritoneal macrophages after treatment with LPS and the recombinant proteins, respectively, which were measured by ELISA. The treatment with C10-LRR led to a significant reduction in the level of IL-6 compared to the treatment with the other recombinant proteins.

No significant difference in TNF-α level was observed between the treatment with C10-LRR and the treatment with the other recombinant proteins.

Figure 32:
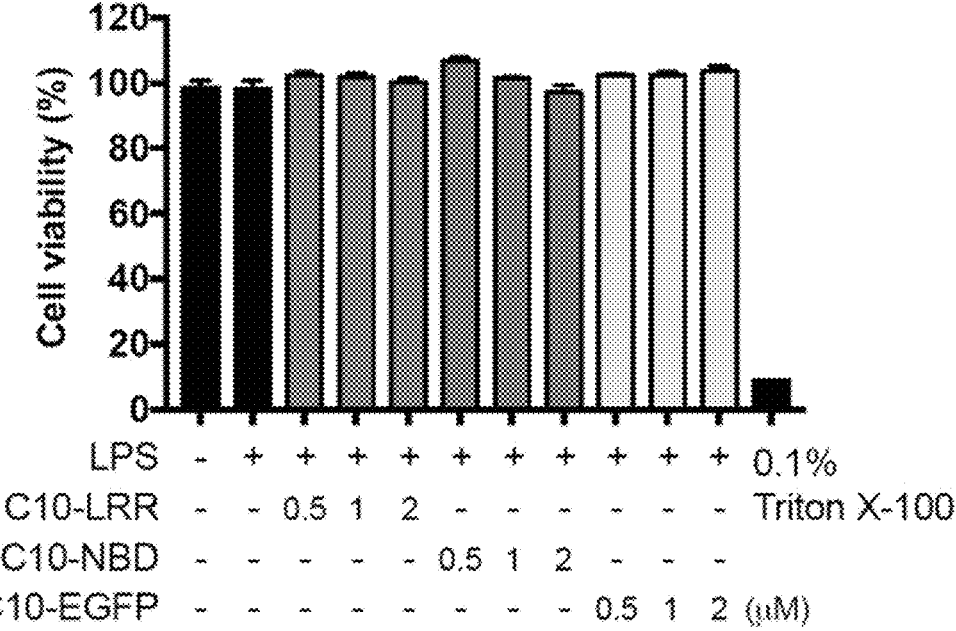
FIG. 32 shows the viabilities of peritoneal macrophages after treatment with LPS and recombinant proteins.

FIG. 32 shows the viabilities of the peritoneal macrophages after treatment with LPS and the recombinant proteins. As shown in FIG. 32, none of C10-LRR, C10-EGFP, and C10-NBD showed toxicity to cells.

Experimental Example 13. Time-Dependent Inhibitory Effects of C10-LRR on NF-κB Activation and IL-6 Production in THP-1

Western Blot-1

Peritoneal macrophages were obtained in the same manner as in Experimental Example 8. The peritoneal macrophages were seeded into 96- or 12-well plates and cultured in a 5% $CO_2$ incubator at 37° C. until adherence. Floating cells were removed with PBS. For inflammasome activation in the adherent macrophages, the macrophages were cultured with 1 mg/ml LPS for 4 h. At this time, the culture was treated with various concentrations (0.2 μM, 0.5 μM, and 1 μM) of each of the recombinant proteins (C10-LRR, C10-NBD, and C10-EGFP) together with LPS for stimulation. Thereafter, cells were lysed in RIPA buffer (Cell Signaling Technology) at 4° C. for 30 min and the protein amount of the lysate was analyzed using a Pierce BCA protein assay kit (Thermo Fisher Scientific) according to the manufacturer's protocol. After SDS-PAGE, proteins were transferred to a PVDF membrane (Bio-Rad), which was then treated with Tris-buffered saline (TBS-T) containing 5% skim milk and 0.1% Tween-20. The membrane was incubated with a primary antibody at 4° C. overnight. IκBα antibody (Cell Signaling, 1:1000 diluted) was used as the primary antibody. The membrane was washed with TBS-T and incubated with a secondary antibody at room temperature for 1 h. The membrane was washed with TBS-T, treated with EZ-Western Lumi Pico or Femto reagent (DoGen), and analyzed using Fusion-Solo software (Vilber) according to the manufacturer's protocol to determine band intensities.

Western Blot-2

THP-1 cells were purchased from ATCC and stored in DMEM or RPMI (Corning) media. Culture media supplemented with 10% fetal bovine serum and 1% penicillin/streptomycin were used. Cells were cultured in a 5% $CO_2$ incubator at 37° C.

The THP-1 cells were activated from 15 min to 5 h with 1 mg/ml LPS (055:B5, Sigma L2880). At this time, the activated cells were treated with various concentrations (0.2 μM, 0.5 μM, and 1 μM) of each of the recombinant proteins (C10-LRR, C10-NBD, and C10-EGFP) together with LPS for stimulation. Thereafter, cells were lysed in RIPA buffer (Cell Signaling Technology) at 4° C. for 30 min and the protein amount of the lysate was analyzed using a Pierce BCA protein assay kit (Thermo Fisher Scientific) according to the manufacturer's protocol. After SDS-PAGE, proteins were transferred to a PVDF membrane (Bio-Rad), which was then treated with Tris-buffered saline (TBS-T) containing 5% skim milk and 0.1% Tween-20. The membrane was incubated with a primary antibody at 4° C. overnight. IκBα (Cell Signaling, 1:1000 diluted), pIκBα Ser32 (Cell Signaling, 1:1000 diluted), p65 (Cell Signaling, 1:1000 diluted), p65 Ser536 (Cell Signaling, 1:1000 diluted), PI3K p110β (Cell Signaling, 1:1000 diluted), pAKT Ser473, caspase (Adipogen, 1:1000 diluted), MAVS (Cell Signaling, 1:1000 diluted), NLRP3 (Adipogen, 1:1000 diluted) or VDAC (Cell Signaling, 1:1000 diluted) antibody was used as the primary antibody. The membrane was washed with TBS-T and incubated with a secondary antibody at room temperature for 1 h. The membrane was washed with TBS-T, treated with EZ-Western Lumi Pico or Femto reagent (DoGen), and analyzed using Fusion-Solo software (Vilber) according to the manufacturer's protocol to determine band intensities.

ELISA

Peritoneal macrophages were obtained in the same manner as in Experimental Example 8. The peritoneal macrophages were seeded into 96- or 12-well plates and cultured in a 5% $CO_2$ incubator at 37° C. until adherence. Floating cells were removed with PBS. For inflammasome activation in the adherent macrophages, the macrophages were cultured with 1 mg/ml LPS for 4 h. At this time, the culture was treated with various concentrations (0.2 μM, 0.5 μM, and 1 μM) of each of the recombinant proteins (C10-LRR, C10-NBD, and C10-EGFP) together with LPS for stimulation. Thereafter, each culture supernatant was collected for ELISA. The levels of IL-6, TNFα, and IL-1β in the culture supernatant were measured using an ELISA kit (BioLegend) according to the manufacturer's protocol.

Statistics

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

Figure 33:
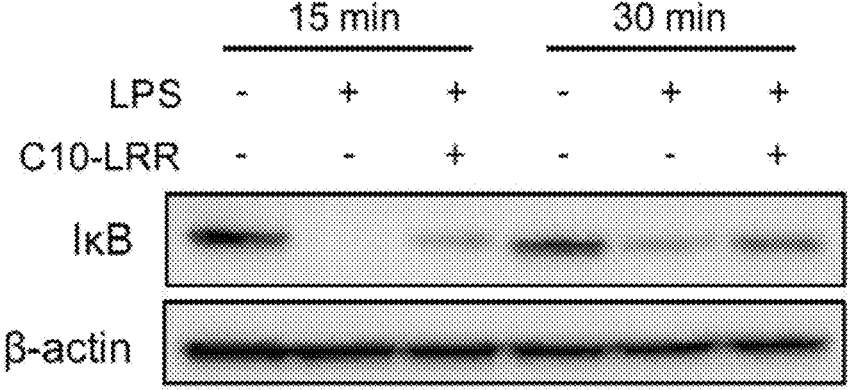
FIG. 33 shows the results of Western blot for peritoneal macrophages after treatment with 1 $\mu$M C10-LRR and 1 mg/ml LPS and culture for 15 minutes and 30 minutes.

FIG. 33 shows the results of Western blot for the peritoneal macrophages after treatment with 1 μM C10-LRR and 1 mg/ml LPS and culture for 15 min and 30 min.

As shown in FIG. 33, the treatment with C10-LRR significantly inhibited IκB degradation regardless of the culture time. This was also observed in human macrophages, that is, THP-1 cells stimulated with phorbol 12-myristate 13-acetate (PMA).

Figure 34:
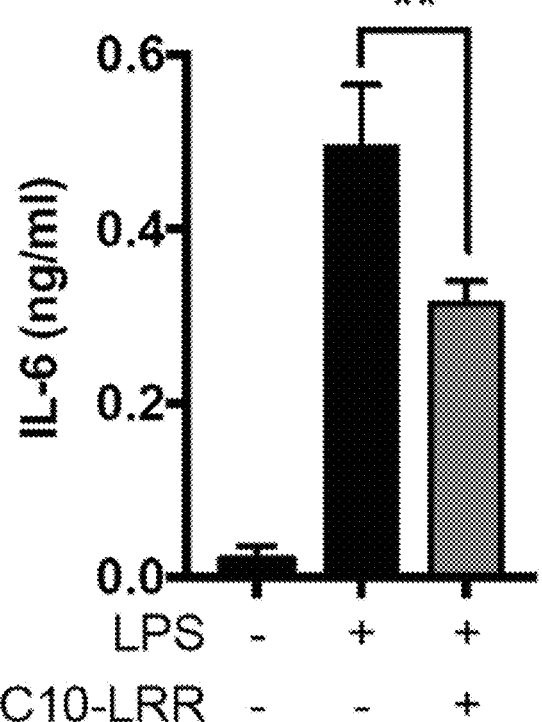
FIGS. 34 and 35 show the levels of IL-6 and TNF-$\alpha$ in PMA-stimulated THP-1 cells after treatment with C10-LRR and LPS, respectively, which were analyzed by ELISA.
Figure 35:
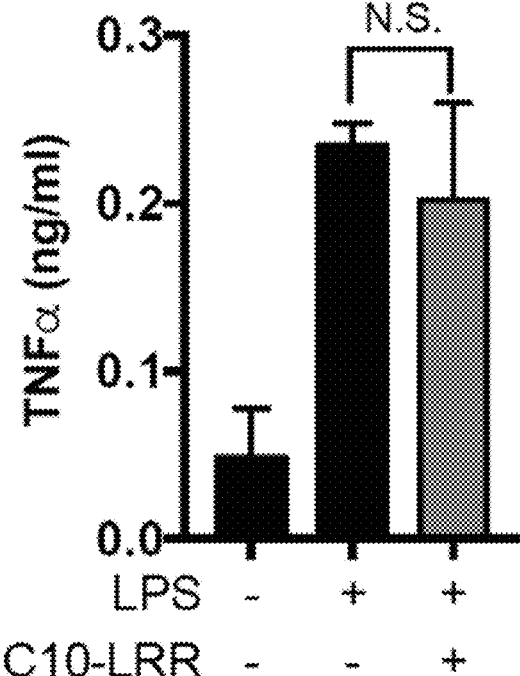

FIGS. 34 and 35 show the levels of IL-6 and TNF-α in the PMA-stimulated THP-1 cells after treatment with C10-LRR and LPS, respectively, which were analyzed by ELISA.

As shown in FIG. 34, the treatment with C10-LRR significantly inhibited IL-6 production. In contrast, no significant difference in TNF-α production was observed.

Figure 36:
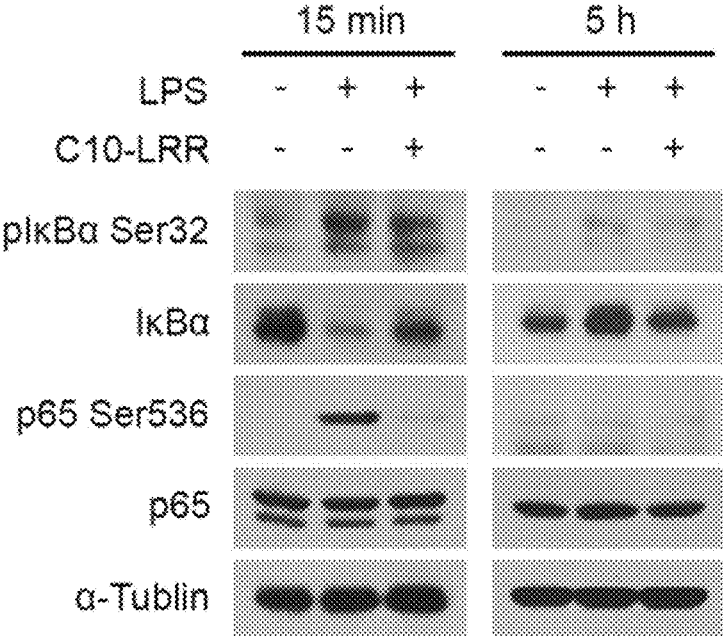
FIG. 36 shows the expression levels of PI$\kappa$B$\alpha$ Ser32, I$\kappa$B$\alpha$, p65 Ser536, and p65 in THP-1 cells after treatment with 1 $\mu$M C10-LRR and 1 mg/ml LPS for 30 minutes, which were measured by Western blot.

FIG. 36 shows the expression levels of PIκBα Ser32, IκBα, p65 Ser536, and p65 in the THP-1 cells after treatment with 1 μM C10-LRR and 1 mg/ml LPS for 30 min, which were measured by Western blot.

As shown in FIG. 36, the treatment with C10-LRR significantly reduced the activation of NF-κB signaling, including phosphorylation of IκBα Ser32, degradation of IκBα, and phosphorylation of p65 Ser536, in the THP-1 cells.

The above experimental results demonstrate that C10-LRR plays a role in inhibiting IL-6 production in LPS-treated macrophages and negatively regulating NF-κB signaling.

Experimental Example 14. Inhibitory Effect of C10-LRR on IL-1β Change in Macrophages Peritoneal macrophages were obtained in the same manner as in Experimental Example 8. The peritoneal macrophages were seeded into 96- or 12-well plates and cultured in a 5% $CO_2$ incubator at 37° C. until adherence. Floating cells were removed with PBS. The adherent cells were treated with various concentrations (0.2 μM, 0.5 μM, and 1 μM) of each of the recombinant proteins (C10-LRR, C10-

NBD, and C10-EGFP) and stimulated for 4 h. Thereafter, each culture supernatant was collected for ELISA. The seeded macrophages were primarily cultured with 1 mg/ml LPS for 4 h for inflammasome activation. The primarily cultured cells were activated with 5 μM nigericin for 2 h. The culture supernatant was collected for ELISA. The levels of IL-6, TNFα, and IL-1β in the culture supernatant were measured using an ELISA kit (BioLegend) according to the manufacturer's protocol.

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

Figure 37:
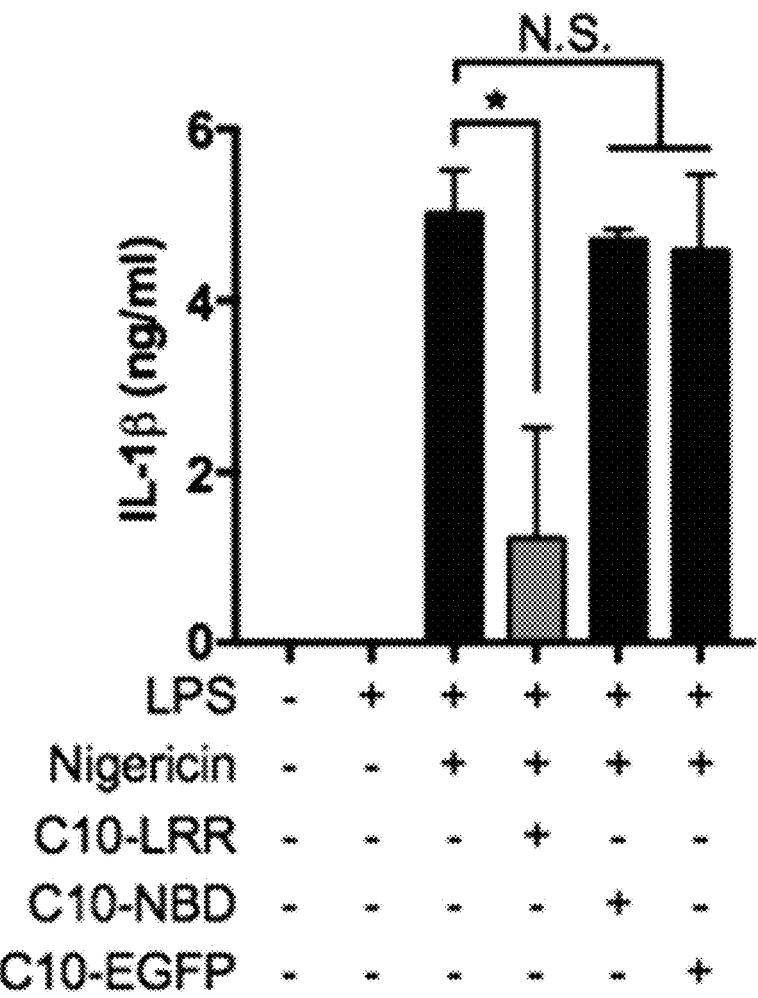
FIG. 37 shows the levels of IL-1$\beta$ in peritoneal macrophages after culture of the cells with LPS, recombinant proteins (C10-LRR, C10-NBD, and C10-EGFP), and nigericin, which were measured by ELISA.

FIG. 37 shows the levels of IL-1β in the peritoneal macrophages after culture of the cells with LPS, the recombinant proteins (C10-LRR, C10-NBD, and C10-EGFP), and nigericin, which were measured by ELISA.

In this experiment, an investigation was made as to whether the decreased IL-1β in the sepsis animal models was associated with the regulation of inflammasome activation by C10-LRR. To this end, after priming with LPS and subsequent treatment with nigericin, an IL-1β change in the macrophages was observed. As a result, the treatment with LPS only did not induce a significant difference in IL-1β change but the co-treatment with LPS and nigericin led to a significant increase in IL-1β change, as shown in FIG. 37.

The C10-LRR treatment was found to significantly inhibit IL-1β.

Experimental Example 15. Inhibitory Effect of C10-LRR on NLRP3-Inflammaseom in Macrophages-11

Sample Administration

For sample administration, mice were divided into nine divided groups.

Peritoneal macrophages or murine embryonic fibroblasts (MEFs) were seeded into 96- or 12-well plates and cultured in a 5% $CO_2$ incubator at 37° C. until adherence.

Figure 38:
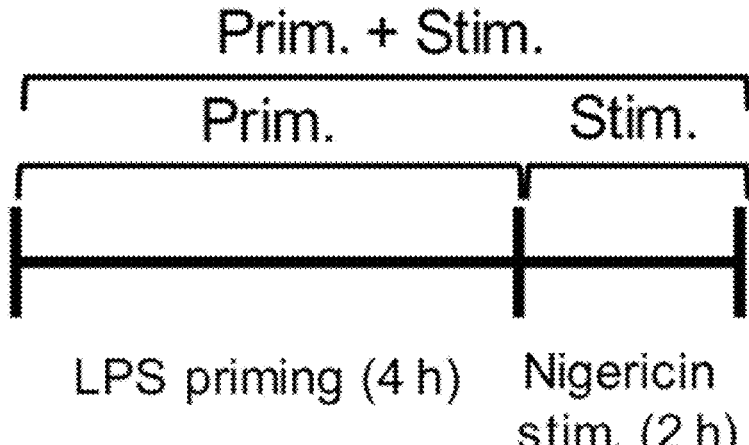
FIG. 38 shows an experimental design for determining the inhibitory effect of C10-LRR on inflammasome activation in peritoneal macrophages.

This experiment was conducted through two steps: priming (intraperitoneal administration of 1 mg/ml LPS, 4 h) and stimulation (intraperitoneal administration of 5 μM nigericin, 2 h) (FIG. 38). In the Prim+Stim group, cells were treated with the same concentration of each of the recombinant proteins (C10-LRR and C10-EGFP) in both priming and stimulation steps, followed by culture. The concentrations (0.2 μM, 0.5 μM, and 1 μM) are indicated on the graph. Each recombinant protein was administered once in each of the prim and stim steps (a total of twice).

In the Prim group, cells were treated with the corresponding concentrations (0.2 μM, 0.5 μM, and 1 μM) of the recombinant proteins (C10-LRR and C10-EGFP) only in the priming step. In the Stim group, cells were treated with the corresponding concentrations (0.2 μM, 0.5 μM, and 1 μM) of the recombinant proteins (C10-LRR and C10-EGFP) only in the stimulation step.

The signs "−" and "+" on the graph indicate non-treatment and treatment of the samples, respectively.

ELISA

The culture supernatants were collected from the sample-administered groups for ELISA. The levels of IL-6, TNFα, and IL-1β in each culture supernatant were measured using an ELISA kit (BioLegend) according to the manufacturer's protocol.

Statistics

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

FIG. 38 shows an experimental design for determining the inhibitory effect of C10-LRR on inflammasome activation in peritoneal macrophages. The experiment was conducted through two steps: priming (intraperitoneal administration of 1 mg/ml LPS, 4 h) and stimulation (intraperitoneal administration of 5 μM nigericin, 2 h). A total of three groups were designed for the experiment. In the Prim+Stim group, cells were treated with each of the recombinant proteins in both priming and stimulation steps. In the Prim group, cells were treated with the recombinant proteins only in the priming step. In the Stim group, cells were treated with the recombinant proteins only in the stimulation step. At this time, LPS was used together with the recombinant proteins (C10-LRR, C10-NBD, and C10-EGFP) for cell treatment. NF-κB activation and inflammasome activation are believed to occur in the priming and stimulation steps, respectively.

Figure 39:
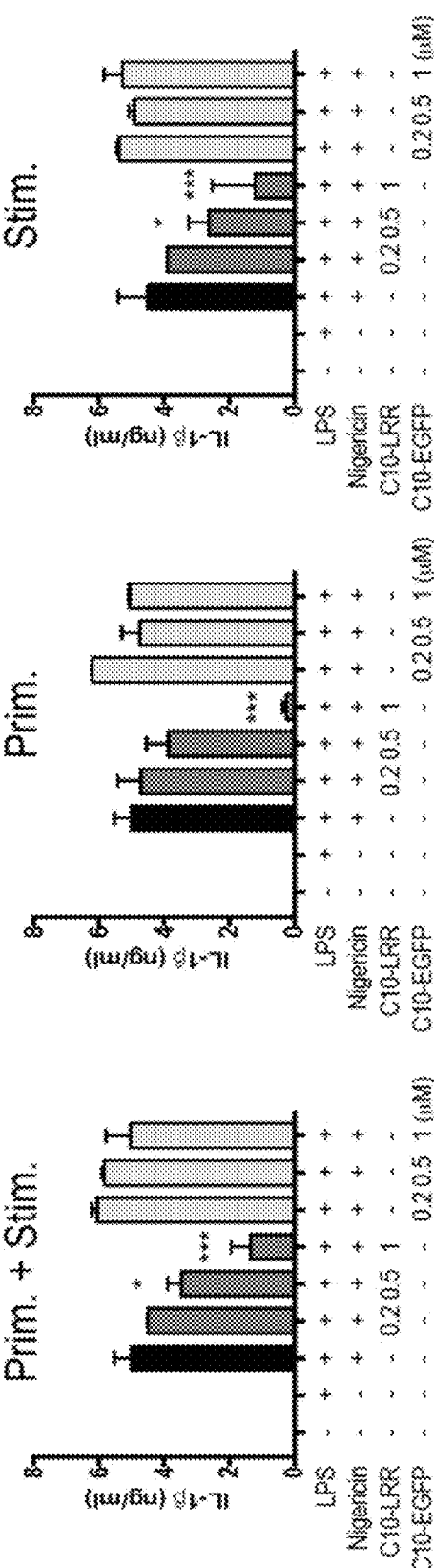
FIG. 39 shows the levels of IL-1$\beta$ in Prim+Stim, Prim, and Stim groups where various concentrations (0.2 $\mu$M, 0.5 $\mu$M, and 1 $\mu$M) of recombinant proteins (C10-LRR and C10-EGFP) were administered to peritoneal macrophages, which were analyzed by ELISA.
Figure 40:
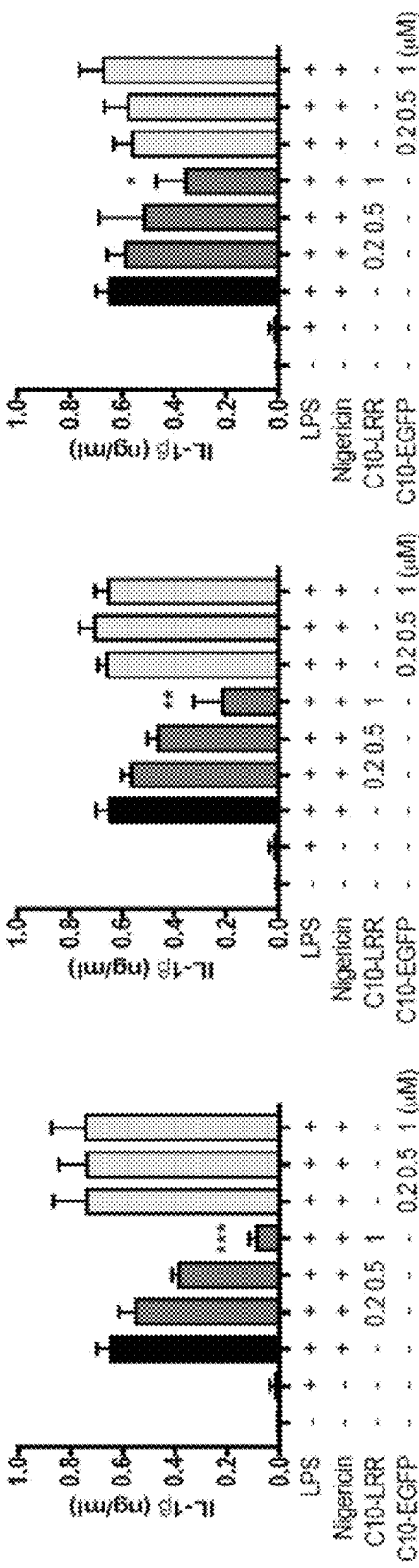
FIG. 40 shows the levels of IL-1$\beta$ in Prim+Stim, Prim, and Stim groups where various concentrations (0.2 $\mu$M, 0.5 $\mu$M, and 1 $\mu$M) of recombinant proteins (C10-LRR and C10-EGFP) were administered to murine embryonic fibroblasts (MEFs), which were analyzed by ELISA.

FIG. 39 shows the levels of IL-1β in the Prim+Stim, Prim, and Stim groups where various concentrations (0.2 μM, 0.5 μM, and 1 μM) of the recombinant proteins (C10-LRR and C10-EGFP) were administered to the peritoneal macrophages, which were analyzed by ELISA. FIG. 40 shows the levels of IL-1β in the Prim+Stim, Prim, and Stim groups where various concentrations (0.2 μM, 0.5 μM, and 1 μM) of the recombinant proteins (C10-LRR and C10-EGFP) were administered to the murine embryonic fibroblasts (MEFs), which were analyzed by ELISA.

As shown in FIGS. 39 and 40, the production of IL-1β was induced by treatment with LPS and nigericin. The C10-LRR treatment was found to significantly reduce IL-1β production in a dose-dependent manner.

From the above results, it can be seen that C10-LRR has an inhibitory effect on both inflammasome signaling and NF-κB signaling. In contrast, the C10-EGFP treatment did not induce a significant difference in IL-1β change.

Experimental Example 16. Inhibitory Effect of C10-LRR on NLRP3-Inflammaseom in Macrophages-12

Isolation of Mitochondrial Fraction

A mitochondrial fraction was isolated using a QPRO-TEOME™ mitochondrial isolation kit (Qiagen) according to the manufacturer's protocol. Briefly, peritoneal macrophages were recovered from lysis buffer and centrifuged at 4° C. and 1,000 g for 10 min. The supernatant was discarded. The pellets were disrupted by repeated (10 times) passage through a 23-gauge needle, followed by centrifugation at 4° C. and 1,000 g for 10 min. The supernatant was centrifuged at 4° C. and 8,000 g for 15 min and the pellets were washed to obtain a mitochondrial fraction. For comparison, whole cell lysate was separately collected and stored.

Western Blot

Peritoneal macrophages, mitochondrial fraction or whole cell lysate was seeded into 96- or 12-well plates and cultured in a 5% $CO_2$ incubator at 37° C. until adherence. Floating cells were removed with PBS. For inflammasome activation in the adherent cells, the macrophages were cultured with 1 mg/ml LPS for 4 h. At this time, the culture was treated with various concentrations (0.2 μM, 0.5 μM, and 1 μM) of each of the recombinant proteins (C10-LRR, C10-NBD, and C10-EGFP) together with LPS for stimulation. Thereafter, the cells were treated with 5 μM nigericin and cultured for 2 h. Thereafter, cells were lysed in RIPA buffer (Cell Signaling Technology) at 4° C. for 30 min and the protein amount of the lysate was analyzed using a PIERCE™ BCA protein assay kit (Thermo Fisher Scientific) according to the manufacturer's protocol. After SDS-PAGE, proteins were transferred to a PVDF membrane (Bio-Rad), which was then treated with Tris-buffered saline (TBS-T) containing 5% skim milk and 0.1% TWEEN™-20. The membrane was incubated with a primary antibody at 4° C. overnight. pro-Casp1 (Adipogen, 1:1000 diluted), casp1P20 (Adipogen, 1:1000 diluted), MAVS (Cell Signaling, 1:1000 diluted), NLRP3 (Adipogen, diluted) 1:1000 diluted) or VDAC (Cell Signaling, 1:1000 diluted) antibody was used as the primary antibody. The membrane was washed with TBS-T and incubated with a secondary antibody at room temperature for 1 h. The membrane was washed with TBS-T, treated with EZ-Western Lumi Pico or Femto reagent (DoGen), and analyzed using Fusion-Solo software (Vilber) according to the manufacturer's protocol to determine band intensities. The peritoneal macrophages used were obtained in the same manner as in Experimental Example 8.

Statistics

For statistical analysis of the experimental data, significant differences in mean values between groups were determined using two-tailed Student's t-test and one- or two-way ANOVA. * indicates a significant difference at $p<0.05$,  indicates a significant difference at $p<0.01$, * indicates a significant difference at $p<0.001$, and N.S indicates no significant difference. MFI indicates median fluorescence intensity. Error bars indicate S.D.

Figure 41:
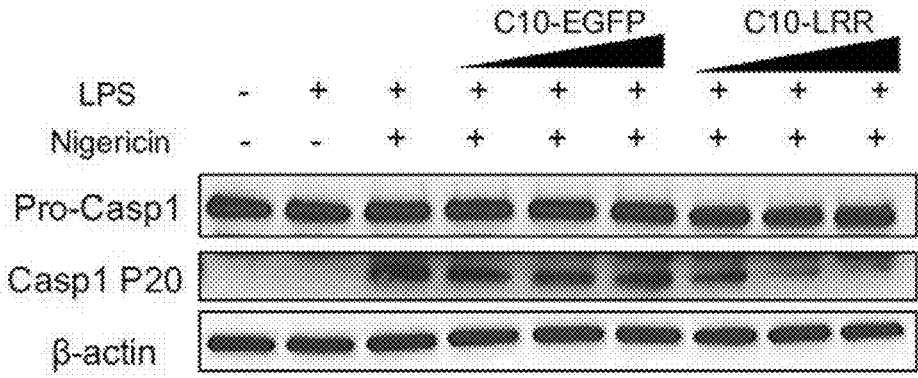
FIG. 41 shows the expression levels of Pro-Casp1 and Casp1 P20 in peritoneal macrophages in which inflammation was induced by LPS and nigericin, after culture with various concentrations (0.2 $\mu$M, 0.5 $\mu$M, and 1 $\mu$M) of recombinant proteins (C10-LRR and C10-EGFP), which were measured by Western blot.

FIG. 41 shows the expression levels of Pro-Casp1 and Casp1 P20 in the peritoneal macrophages in which inflammation was induced by LPS and nigericin, after culture with various concentrations (0.2 μM, 0.5 μM, and 1 μM) of the recombinant proteins (C10-LRR and C10-EGFP), which were measured by Western blot.

It is known that caspase-1 p20 cleaves the N-terminus of Pro-IL-1β to produce a secretable form of mature IL-1β. Thus, the relevance between C10-LRR and caspase-1 p20 was analyzed.

As shown in FIG. 41, the treatment with LPS and nigericin led to a significant increase in the expression level of caspase-1 p20 compared to the normal group. In contrast, the treatment with C10-LRR was found to significantly reduce the expression level of caspase-1 p20, which had been increased by LPS and nigericin. No significant difference was observed between the comparative group (C10-EGFP) and the LPS/nigericin treated group.

Figure 42:
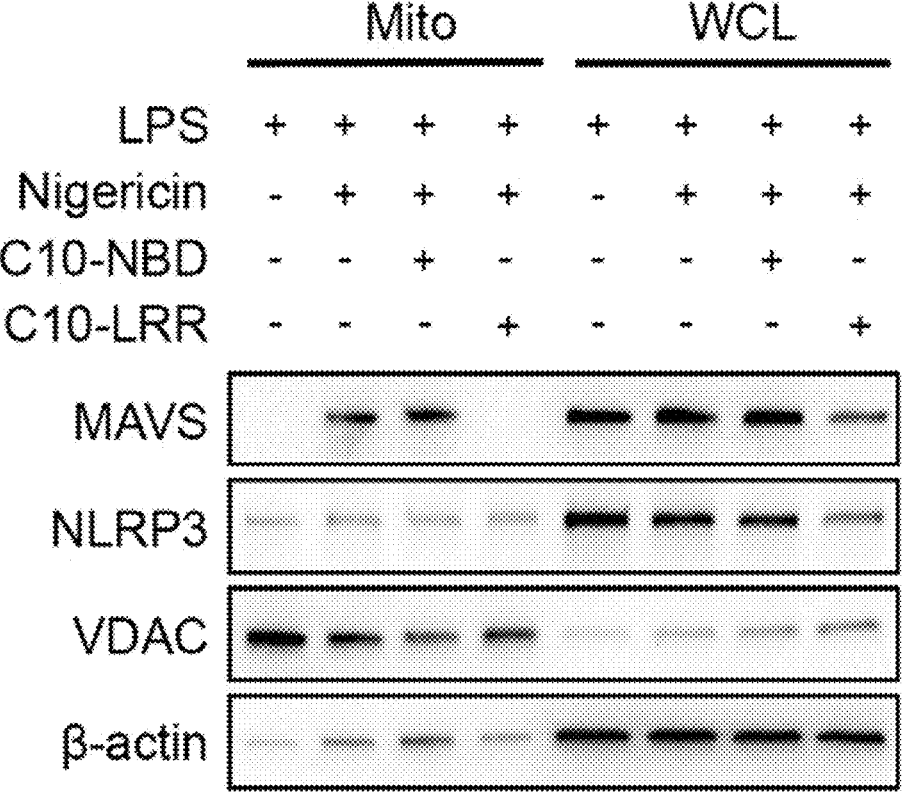
FIG. 42 shows the expression levels of Pro-Casp1 and Casp1 P20 in mitochondrial fractions and whole cell lysates in which inflammation was induced by LPS and nigericin, after culture with various concentrations (0.2 $\mu$M, 0.5 $\mu$M, and 1 $\mu$M) of recombinant proteins (C10-LRR and C10-EGFP), which were measured by Western blot.

FIG. 42 shows the expression levels of Pro-Casp1 and Casp1 P20 in mitochondrial fractions and whole cell lysates in which inflammation was induced by LPS and nigericin, after culture with the recombinant proteins (C10-LRR and C10-EGFP), which were measured by Western blot. In FIG. 42, "Mito" is the mitochondrial fraction and "WCL" is the whole cell lysate.

MAVS is widely known to play a role in regulating NLRP3-inflammasome in the mitochondrial outer membrane. Thus, the levels of NLRP3 and MAVS in the mitochondria and cytoplasm after treatment with C10-LRR were investigated.

As shown in FIG. 42, the stimulation with nigericin and LPS led to a significant increase in the level of MAVS in mitochondria, with no difference in the level of MAVS in WCL.

The treatment with C10-LRR was found to completely inhibit the expression of MAVS in mitochondria and significantly reduce the levels of MAVS and NLRP3 in WCL. From the above results, it can be concluded that C10-LRR negatively regulates inflammasome signaling and IL-1β production.

Experimental Example 17. Analysis of Effect of Combination of Conventional Drug and C10-LRR on Ameliorating Sepsis when the Combination was Administered Twice Experimental Animals 7- to 8-week-old male or female C57BL/6 mice were housed and bred in a specific pathogen-free animal facility at Hanyang University. The mice were acclimatized for two weeks before the experiment. The mice were housed in the facility maintained at a temperature of 21±2° C. and a humidity of 40-60% on a 12-h light/dark cycle and were given water and food ad libitum over the entire experimental period. All animal experiments were conducted in accordance with the Animal Care and Use Protocol approved by the Institutional Animal Care and Use Committee of Hanyang University.

Sample Administration and Sampling

For sample administration, mice were randomly divided into four groups, 5 animals per group. LPS (2 mg/kg) and PBS (1 mg/kg) were intraperitoneally injected (I.P injection) at 0 h and LPS (5 mg/kg) and PBS (1 mg/kg) were intraperitoneally injected at 5 h ("PBS", negative control). LPS (2 mg/kg) and the C10-LRR recombinant protein (1 mg/kg) were intraperitoneally injected (I.P injection) at 0 h and LPS (5 mg/kg) and the C10-LRR recombinant protein (1 mg/kg) were intraperitoneally injected at 5 h ("C10-LRR-administered group"). LPS (2 mg/kg) and αTNFαAb (1 mg/kg) were intraperitoneally injected (I.P injection) at 0 h and LPS (5 mg/kg) and αTNFαAb (1 mg/kg) were intraperitoneally injected at 5 h ("αTNFαAb-administered group"). LPS (2 mg/kg), the C10-LRR recombinant protein (1 mg/kg), and αTNFαAb (1 mg/kg) were intraperitoneally injected (I.P injection) at 0 h and LPS (5 mg/kg), the C10-LRR recombinant protein (1 mg/kg), and αTNFαAb (1 mg/kg) were intraperitoneally injected at 5 h ("C10-LRR+ αTNFαAb-administered group"). These groups were measured for changes in survival and weight every 24 h for a total of 7 days. αTNFαAb indicates a TNFα neutralizing antibody.

4 Groups of Animal Models

Group 1 (PBS): LPS (2 mg/kg) and PBS (1 mg/kg) were intraperitoneally administered at 0 h and LPS (5 mg/kg) and PBS (1 mg/kg) were intraperitoneally administered at 5 h.

Group 2 (C10-LRR): LPS (2 mg/kg) and the C10-LRR recombinant protein (1 mg/kg) were intraperitoneally administered at 0 h and LPS (5 mg/kg) and the C10-LRR recombinant protein (1 mg/kg) were intraperitoneally administered at 5 h.

Group 3 (αTNFαAb): LPS (2 mg/kg) and αTNFαAb (1 mg/kg) were intraperitoneally administered at 0 h and LPS (5 mg/kg) and αTNFαAb (1 mg/kg) were intraperitoneally administered at 5 h.

Group 4 (C10-LRR+αTNFαAb): LPS (2 mg/kg), the C10-LRR recombinant protein (1 mg/kg), and αTNFαAb (1 mg/kg) were intraperitoneally administered at 0 h and LPS (5 mg/kg), the C10-LRR recombinant protein (1 mg/kg), and αTNFαAb (1 mg/kg) were intraperitoneally administered at 5 h.

The above experimental results demonstrate that C10-LRR is effective in negatively regulating IL-6 and IL-1β. Furthermore, it is believed that the co-administration of C10-LRR and the conventional drug induces a synergistic effect. Thus, the following experiment was conducted.

Figure 43:
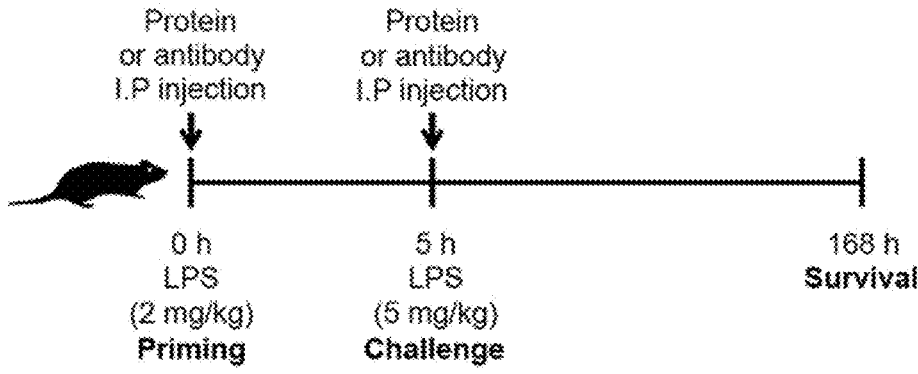
FIG. 43 schematically shows an experimental design for determining the therapeutic effect of a combination of C10-LRR recombinant protein and $\alpha$TNF$\alpha$Ab on sepsis.
Figure 44:
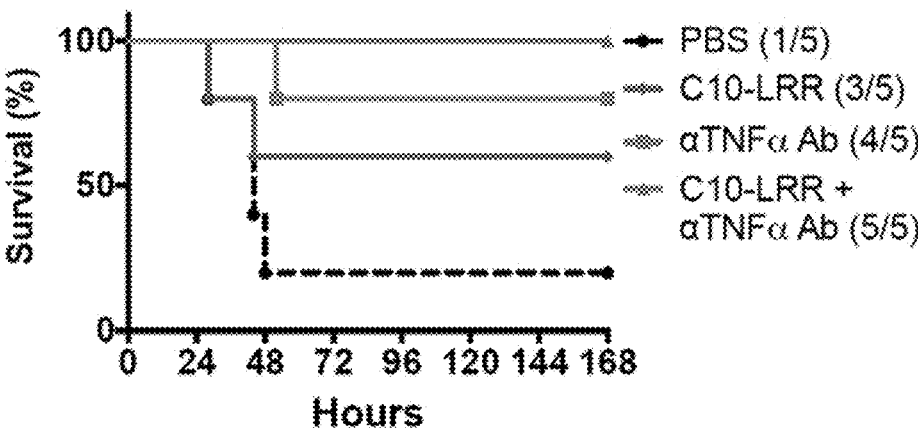
FIG. 44 shows the survivals of animal models in Group 1 (PBS), Group 2 (C10-LRR), Group 3 ($\alpha$TNF$\alpha$Ab), and Group 4 (C10-LRR+$\alpha$TNF$\alpha$Ab), which were measured for 7 days.
Figures 45, 46:
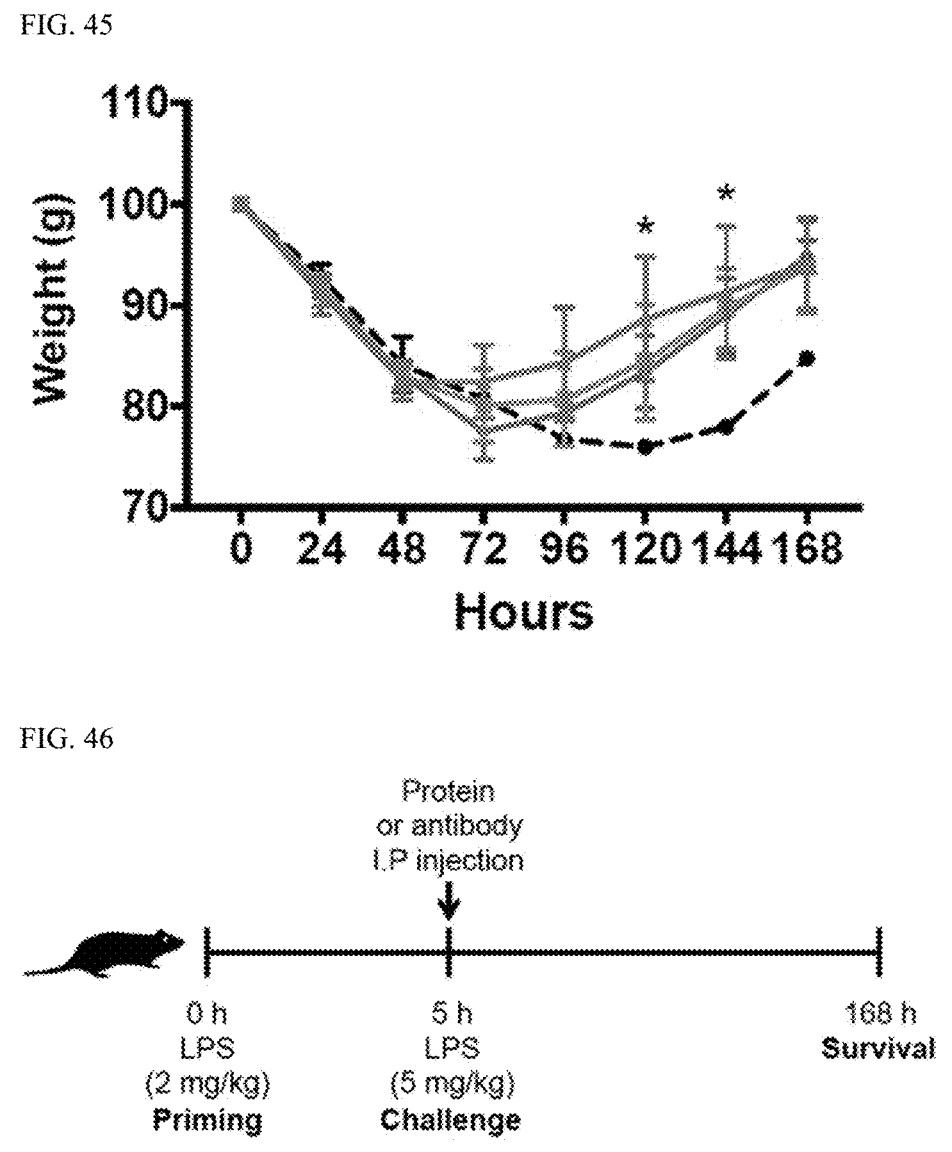

FIG. 43 schematically shows an experimental design for determining the therapeutic effect of the combination of the C10-LRR recombinant protein and αTNFαAb on sepsis. FIG. 44 shows the survivals of the animal models in Group 1 (PBS), Group 2 (C10-LRR), Group 3 (αTNFαAb), and Group 4 (C10-LRR+αTNFαAb), which were measured for 7 days. FIG. 45 shows the weights of the animal models in Group 1 (PBS), Group 2 (C10-LRR), Group 3 (αTNFαAb), and Group 4 (C10-LRR+αTNFαAb), which were measured for 7 days.

As shown in FIGS. 43 and 44, the treatment with C10-LRR or αTNFαAb greatly improved the survival of the animal models. In addition, the animal models in the group treated with C10-LRR or αTNFαAb (72 h) recovered their weight significantly faster than the animal models in the PBS-treated group (120 h). Furthermore, when both C10-LRR and αTNFαAb was used, the survival was restored to 100% and the weight was recovered in the fastest time (48 h).

From these results, it can be concluded that C10-LRR exhibits a significantly superior effect even when used alone and has a remarkable synergistic effect when administered in combination with the conventional drug.

Experimental Example 18. Analysis of Effect of Combination of Conventional Drug and C10-LRR on Ameliorating Sepsis when the Combination was Administered Once Experimental Animals 7- to 8-week-old male or female C57BL/6 mice were housed and bred in a specific pathogen-free animal facility at Hanyang University. The mice were acclimatized for two weeks before the experiment. The mice were housed in the facility maintained at a temperature of 21±2° C. and a humidity of 40-60% on a 12-h light/dark cycle and were given water and food ad libitum over the entire experimental period. All animal experiments were conducted in accordance with the Animal Care and Use Protocol approved by the Institutional Animal Care and Use Committee of Hanyang University.

Sample Administration and Sampling

For sample administration, mice were randomly divided into four groups, 5 animals per group. LPS (2 mg/kg) was intraperitoneally injected (I.P injection) at 0 h and LPS (5 mg/kg) and PBS (1 mg/kg) were intraperitoneally injected at 5 h ("PBS", negative control). LPS (2 mg/kg) was intraperitoneally injected (I.P injection) at 0 h and LPS (5 mg/kg) and the C10-LRR recombinant protein (1 mg/kg) were intraperitoneally injected at 5 h ("C10-LRR-administered group"). LPS (2 mg/kg) was intraperitoneally injected (I.P injection) at 0 h and LPS (5 mg/kg) and αTNFαAb (1 mg/kg) were intraperitoneally injected at 5 h ("αTNFαAb-administered group"). LPS (2 mg/kg) was intraperitoneally injected (I.P injection) at 0 h and LPS (5 mg/kg), the C10-LRR recombinant protein (1 mg/kg), and αTNFαAb (1 mg/kg) were intraperitoneally injected at 5 h ("C10-LRR+ αTNFαAb-administered group"). These groups were measured for changes in survival and weight every 24 h for a total of 7 days. αTNFαAb indicates a TNFα neutralizing antibody.

4 Groups of Animal Models

Group 1 (PBS): LPS (2 mg/kg) was intraperitoneally administered at 0 h and LPS (5 mg/kg) and PBS (1 mg/kg) were intraperitoneally administered at 5 h.

Group 2 (C10-LRR): LPS (2 mg/kg) was intraperitoneally administered at 0 h and LPS (5 mg/kg) and the C10-LRR recombinant protein (1 mg/kg) were intraperitoneally administered at 5 h.

Group 3 (αTNFαAb): LPS (2 mg/kg) was intraperitoneally administered at 0 h and LPS (5 mg/kg) and αTNFαAb (1 mg/kg) were intraperitoneally administered at 5 h.

Group 4 (C10-LRR+αTNFαAb): LPS (2 mg/kg) was intraperitoneally administered at 0 h and LPS (5 mg/kg), the C10-LRR recombinant protein (1 mg/kg), and αTNFαAb (1 mg/kg) were intraperitoneally administered at 5 h.

Figure 47:
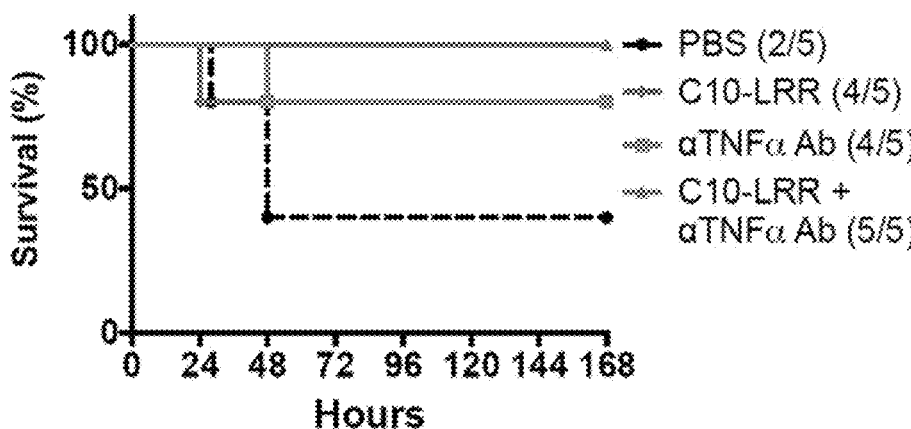
FIG. 47 shows the survivals of animal models in Group 1 (PBS), Group 2 (C10-LRR), Group 3 ($\alpha$TNF$\alpha$Ab), and Group 4 (C10-LRR+$\alpha$TNF$\alpha$Ab), which were measured for 7 days.

An analysis was conducted to determine the effect of co-administration of C10-LRR and the conventional drug when the combination was administered once. FIG. 46 schematically shows an experimental design for determining the therapeutic effect of the combination of the C10-LRR recombinant protein and αTNFαAb on sepsis when the combination was administered once. FIG. 47 shows the survivals of the animal models in Group 1 (PBS), Group 2

Figure 48:
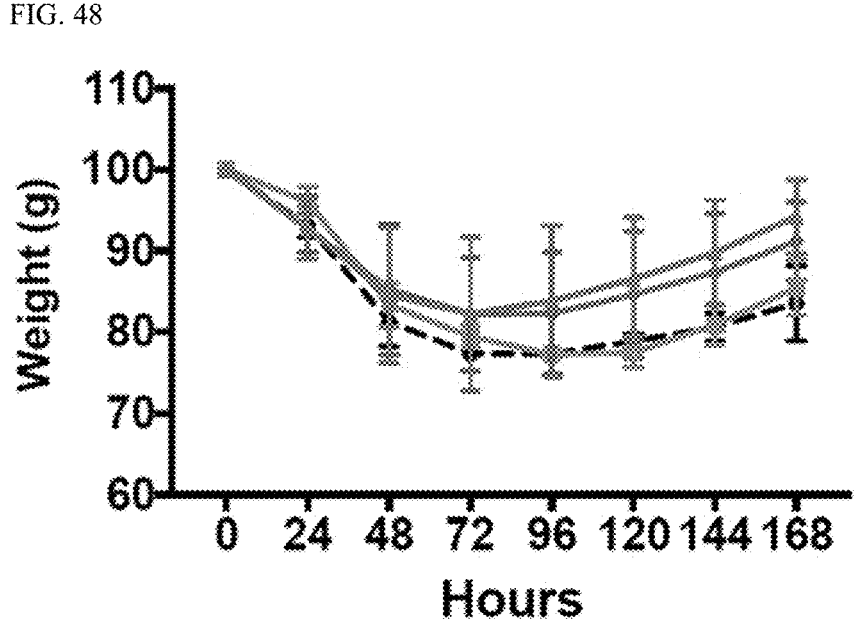
FIG. 48 shows the weights of animal models in Group 1 (PBS), Group 2 (C10-LRR), Group 3 ($\alpha$TNF$\alpha$Ab), and Group 4 (C10-LRR+$\alpha$TNF$\alpha$Ab), which were measured for 7 days.

(C10-LRR), Group 3 (αTNFαAb), and Group 4 (C10-LRR+ αTNFαAb), which were measured for 7 days. FIG. 48 shows the weights of the animal models in Group 1 (PBS), Group 2 (C10-LRR), Group 3 (αTNFαAb), and Group 4 (C10-LRR+αTNFαAb), which were measured for 7 days.

As shown in FIGS. 47 and 48, the survival of the animal models in Group 4 administered both C10-LRR and αTNFαAb was significantly increased compared to those in Group 2 administered C10-LRR alone and in Group 3 administered αTNFαAb alone. The animal models in Group 4 recovered their weight significantly faster than the animal models in Groups 2 and 3. The above results indicate that co-administration of C10-LRR and the conventional drug (TNF-α antibody) is very effective in preventing or treating LPS-induced sepsis.

In summary, it was found that the inventive C10 cell penetrating peptide enables selective delivery to macrophages and LRR can be efficiently delivered to macrophages when fused with C10. It was also found that C10-LRR selectively acts on macrophages to regulate NF-κB and inflammatory signaling, enabling the inhibition of IL-1β and IL-6 production. Therefore, C10-LRR successfully exerted a therapeutic or prophylactic effect on systemic diseases (e.g., sepsis) caused by continuous inflammatory response. Furthermore, the inventive C10-LRR was found to induce a synergistic therapeutic effect on sepsis when co-administered with the conventional drug (αTNFαAb) unbound with the C10 cell penetrating peptide.

---

What is claimed is:

1. A fusion product consisting of:

a cell penetrating peptide, a biologically active substance, and a fusing moiety linking the cell penetrating peptide and the biologically active substance, wherein the cell penetrating peptide consists of an amino acid sequence represented by the following formula 1:

(SEQ ID NO: 77)

$$(Xaa1)_a\text{-Arg-Xaa2-Arg-Leu-Arg-Arg-Xaa3-His-}(Xaa4)_b$$
(1)

wherein each Xaa1 is independently an amino acid selected from the group consisting of leucine, arginine, and lysine, Xaa2 is an amino acid selected from the group consisting of alanine, glycine, proline, leucine, and methionine, Xaa3 is an amino acid selected from the group consisting of alanine, and cysteine, each Xaa4 is arginine, a is an integer from 0 to 2, and b is an integer from 0 to 2, wherein the cell penetrating peptide is composed of 8 to 12 amino acid residues, and the biologically active substance is an LRR (leucine rich repeat) domain derived from NLRX1 protein, consisting of the sequence set forth in SEQ ID NO: 25.

2. The fusion product according to claim 1, wherein the cell penetrating peptide is composed of 9 to 10 amino acid residues.

3. The fusion product according to claim 2, wherein a is an integer 1 or 2, and each Xaa1 is independently leucine.

4. The fusion product according to claim 2, wherein Xaa3 is cysteine.

5. The fusion product according to claim 2, wherein Xaa2 is leucine.

6. The fusion product according to claim 1, wherein the cell penetrating peptide consists of one selected from the group of the amino acid sequences set forth in SEQ ID NOS: 1, 3, 5, 7, 9, 11, and 13.

7. The fusion product according to claim 1, wherein the fusion product targets one or more types of immune cells selected from the group consisting of macrophages, B lymphocytes, T lymphocytes, mast cells, monocytes, dendritic cells, eosinophils, natural killer cells, basophils, and neutrophils.

8. The fusion product according to claim 1, wherein the cell penetrating peptide allows the fusion product to act specifically on macrophages such that the biologically active substance is delivered into macrophages.

9. The fusion product according to claim 1, wherein the fusing moiety is an indirect or direct linking group.

10. The fusion product according to claim 9, wherein the indirect linking group is a recombinant protein.

11. The fusion product according to claim 9, wherein the direct linking group is a covalent or non-covalent bond.

12. A composition consisting of:

the fusion product according to claim 1 and a pharmaceutically acceptable carrier.

13. A method for delivering a biologically active substance, the method comprising injecting the fusion product according to claim 1 into a living body or cells of a non-human mammal.

14. A method for gene therapy, comprising injecting the fusion product according to claim 1 into a living body or cells of a non-human mammal.

* * * * *